US009498538B2

United States Patent
Liao et al.

(10) Patent No.: US 9,498,538 B2
(45) Date of Patent: Nov. 22, 2016

(54) TRANSLOCATION OF NON-NATURAL CHEMICAL ENTITIES THROUGH ANTHRAX PROTECTIVE ANTIGEN PORE

(71) Applicants: Xiaoli Liao, Cambridge, MA (US); Amy E. Rabideau, Cambridge, MA (US); Bradley L. Pentelute, Cambridge, MA (US); Jingjing Ling, Cambridge, MA (US); Gizem Akçay, Medford, MA (US); John Collier, Wellesley, MA (US)

(72) Inventors: Xiaoli Liao, Cambridge, MA (US); Amy E. Rabideau, Cambridge, MA (US); Bradley L. Pentelute, Cambridge, MA (US); Jingjing Ling, Cambridge, MA (US); Gizem Akçay, Medford, MA (US); John Collier, Wellesley, MA (US)

(73) Assignees: Massachusetts Institute of Technology, Cambridge, MA (US); President and Fellows of Harvard College, Cambridge, MA (US)

(*) Notice: Subject to any disclaimer, the term of this patent is extended or adjusted under 35 U.S.C. 154(b) by 88 days.

(21) Appl. No.: 14/402,856

(22) PCT Filed: May 21, 2013

(86) PCT No.: PCT/US2013/042118
§ 371 (c)(1),
(2) Date: Nov. 21, 2014

(87) PCT Pub. No.: WO2013/177231
PCT Pub. Date: Nov. 28, 2013

(65) Prior Publication Data
US 2015/0165062 A1 Jun. 18, 2015

Related U.S. Application Data

(60) Provisional application No. 61/649,866, filed on May 21, 2012, provisional application No. 61/649,421, filed on May 21, 2012.

(51) Int. Cl.
| | |
|---|---|
| A61K 47/48 | (2006.01) |
| C07K 1/107 | (2006.01) |
| C07K 1/04 | (2006.01) |
| C07K 2/00 | (2006.01) |
| C12P 21/06 | (2006.01) |
| A61K 31/7056 | (2006.01) |
| A61K 39/395 | (2006.01) |

(52) U.S. Cl.
CPC ..... *A61K 47/48346* (2013.01); *A61K 31/7056* (2013.01); *A61K 39/395* (2013.01); *A61K 47/48246* (2013.01); *A61K 47/48261* (2013.01); *C07K 1/047* (2013.01); *C07K 1/107* (2013.01); *C07K 2/00* (2013.01); *C12P 21/06* (2013.01)

(58) Field of Classification Search
CPC ............................................. A61K 47/48346
See application file for complete search history.

(56) References Cited

U.S. PATENT DOCUMENTS 5,908,626 A 6/1999 Chang et al.

FOREIGN PATENT DOCUMENTS

| WO | WO 03/074554 A2 | 9/2003 |
|---|---|---|
| WO | WO 2007/083175 A1 | 7/2007 |
| WO | WO 2011/133704 A2 | 10/2011 |
| WO | WO 2012/142659 A1 | 10/2012 |

OTHER PUBLICATIONS

Arora et al., 1992, The Journal of Biological Chemistry, 267(22): 15542-15548.*
Duesbery et al., Proteolytic inactivation of MAP-kinase-kinase by anthrax lethal factor. Science. May 1, 1998;280(5364):734-7.
Falnes et al., Toxins that are activated by HIV type-1 protease through removal of a signal for degradation by the N-end-rule pathway. Biochem J. Oct. 1, 1999;343 Pt 1:199-207.
Feld et al., Structural basis for the unfolding of anthrax lethal factor by protective antigen oligomers. Nat Struct Mol Biol. Nov. 2010;17(11):1383-90. doi: 10.1038/nsmb.1923. Epub Oct. 31, 2010.
Finkelstein, Proton-coupled protein transport through the anthrax toxin channel. Philos Trans R Soc Lond B Biol Sci. Jan. 27, 2009;364(1514):209-15. doi:10.1098/rstb.2008.0126.
Guo et al., Sortase-catalyzed peptide-glycosylphosphatidylinositol analogue ligation. J Am Chem Soc. Jul. 29, 2009;131(29):9878-9. doi: 10.1021/ja903231v.
Hackel et al., Epidermal growth factor receptor downregulation by small heterodimeric binding proteins. Protein Eng Des Sel. Feb. 2012;25(2):47-57. doi: 10.1093/protein/gzr056. Epub Dec. 9, 2011.
Jonsson et al., Generation of tumour-necrosis-factor-alpha-specific affibody molecules capable of blocking receptor binding in vitro. Biotechnol Appl Biochem. Aug. 17, 2009;54(2):93-103. doi: 10.1042/BA20090085.
Katayama et al., GroEL as a molecular scaffold for structural analysis of the anthrax toxin pore. Nat Struct Mol Biol. Jul. 2008;15(7):754-60. doi:10.1038/nsmb.1442. Epub Jun. 22, 2008.
Kintzer et al., The protective antigen component of anthrax toxin forms functional octameric complexes. J Mol Biol. Sep. 25, 2009;392(3):614-29. doi: 10.1016/j.jmb.2009.07.037. Epub Jul. 20, 2009.

(Continued)

*Primary Examiner* — Amber D Steele
(74) *Attorney, Agent, or Firm* — Wolf, Greenfield & Sacks, P.C.

(57) ABSTRACT

Disclosed is a new approach for delivering compounds and drugs to the cytosol of living cells through the use of engineered protein transporters. The engineered protein transporters include a pore and a pore specific delivery protein, wherein a reagent such as a drug is attached to one or more of the engineered protein transporters.

22 Claims, 19 Drawing Sheets

(56) References Cited

OTHER PUBLICATIONS

Klimpel et al., Anthrax toxin protective antigen is activated by a cell surface protease with the sequence specificity and catalytic properties of furin. Proc Natl Acad Sci U S A. Nov. 1, 1992;89(21):10277-81.
Kmiecik et al., Folding pathway of the b1 domain of protein G explored by multiscale modeling. Biophys J. Feb. 1, 2008;94(3):726-36. Epub Sep. 21, 2007.
Koide et al., The fibronectin type III domain as a scaffold for novel binding proteins. J Mol Biol. Dec. 11, 1998;284(4):1141-51.
Krantz et al., A phenylalanine clamp catalyzes protein translocation through the anthrax toxin pore. Science. Jul. 29, 2005;309(5735):777-81.
Krantz et al., Protein translocation through the anthrax toxin transmembrane pore is driven by a proton gradient. J Mol Biol. Feb. 3, 2006;355(5):968-79. Epub Dec. 1, 2005.
Leppla, Anthrax toxin edema factor: a bacterial adenylate cyclase that increases cyclic AMP concentrations of eukaryotic cells. Proc Natl Acad Sci U S A. May 1982;79(10):3162-6.
Lillich et al., Hsp90 and Cyclophilin A facilitate the translocation of the anthrax fusion toxin LFN-DTA across endosomal membrane. Naunyn-Schmiedberg's Archives of Pharmacology. 2011;383(1):9. V34.
Lipovsek, Adnectins: engineered target-binding protein therapeutics. Protein Eng Des Sel. Jan. 2011;24(1-2):3-9. doi: 10.1093/protein/gzq097. Epub Nov. 10, 2010.
Liu et al., Tumor cell-selective cytotoxicity of matrix metalloproteinase-activated anthrax toxin. Cancer Res. Nov. 1, 2000;60(21):6061-7.
Lundberg et al., Selection and characterization of Affibody ligands to the transcription factor c-Jun. Biotechnol Appl Biochem. Jan. 2009;52(Pt 1):17-27. doi: 10.1042/BA20070178.
Mamluk et al., Anti-tumor effect of CT-322 as an adnectin inhibitor of vascular endothelial growth factor receptor-2. MAbs. Mar.-Apr. 2010;2(2):199-208.
Mao et al., Sortase-mediated protein ligation: a new method for protein engineering. J Am Chem Soc. Mar. 10, 2004;126(9):2670-1.
Mazmanian et al., *Staphylococcus aureus* sortase, an enzyme that anchors surface proteins to the cell wall. Science. Jul. 30, 1999;285(5428):760-3.
Milne et al., Anthrax protective antigen forms oligomers during intoxication of mammalian cells. J Biol Chem. Aug. 12, 1994;269(32):20607-12.
Milne et al., Protective antigen-binding domain of anthrax lethal factor mediates translocation of a heterologous protein fused to its amino- or carboxy-terminus. Mol Microbiol. Feb. 1995;15(4):661-6.
Molloy et al., Human furin is a calcium-dependent serine endoprotease that recognizes the sequence Arg-X-X-Arg and efficiently cleaves anthrax toxin protective antigen. J Biol Chem. Aug. 15, 1992;267(23):16396-402.
Nord et al., Binding proteins selected from combinatorial libraries of an alpha-helical bacterial receptor domain. Nat Biotechnol. Aug. 1997;15(8):772-7.
Nygren, Alternative binding proteins: affibody binding proteins developed from a small three-helix bundle scaffold. FEBS J. Jun. 2008;275(11):2668-76. doi: JONSSON10.1111/j.1742-4658.2008.06438.x. Epub Apr. 24, 2008.
Orlova et al., Tumor imaging using a picomolar affinity HER2 binding affibody molecule. Cancer Res. Apr. 15, 2006;66(8):4339-48.
Pallen et al., An embarrassment of sortases—a richness of substrates? Trends Microbiol. Mar. 2001;9(3):97-102.
Pentelute et al., Chemical dissection of protein translocation through the anthrax toxin pore. Angew Chem Int Ed Engl. Mar. 1, 2011;50(10):2294-6. doi: 10.1002/anie.201006460. Epub Feb. 3, 2011.

Popp et al., Making and breaking peptide bonds: protein engineering using sortase. Angew Chem Int Ed Engl. May 23, 2011;50(22):5024-32. doi:10.1002/anie.201008267. Epub Apr. 27, 2011.
Popp et al., Sortagging: a versatile method for protein labeling. Nat Chem Biol. Nov. 2007;3(11):707-8. Epub Sep. 23, 2007.
Samantaray et al., Peptide-sugar ligation catalyzed by transpeptidase sortase: a facile approach to neoglycoconjugate synthesis. J Am Chem Soc. Feb. 20, 2008;130(7):2132-3. doi: 10.1021/ja077358g. Epub Jan. 30, 2008.
Scobie et al., Human capillary morphogenesis protein 2 functions as an anthrax toxin receptor. Proc Natl Acad Sci U S A. Apr. 29, 2003;100(9):5170-4. Epub Apr. 16, 2003.
Thoren et al., Lethal factor unfolding is the most force-dependent step of anthrax toxin translocation. Proc Natl Acad Sci U S A. Dec. 22, 2009;106(51):21555-60. doi: 10.1073/pnas.0905880106. Epub Nov. 19, 2009.
Vitale et al., Anthrax lethal factor cleaves the N-terminus of MAPKKs and induces tyrosine/threonine phosphorylation of MAPKs in cultured macrophages. Biochem Biophys Res Commun Jul. 30, 1998;248(3):706-11.
Wojcik et al., A potent and highly specific FN3 monobody inhibitor of the Abl SH2 domain. Nat Struct Mol Biol. Apr. 2010;17(4):519-27. doi:10.1038/nsmb.1793. Epub Mar. 28, 2010.
Young et al., Anthrax toxin: receptor binding, internalization, pore formation, and translocation. Annu Rev Biochem. 2007;76:243-65.
Zhang et al., Evidence that translocation of anthrax toxin's lethal factor is initiated by entry of its N terminus into the protective antigen channel. Proc Natl Acad Sci U S A. Nov. 30, 2004;101(48):16756-61. Epub Nov. 17, 2004.
Zimm et al., Theory of the Phase Transition between Helix and Random Coil in Polypeptide Chains. J Chem Physics. 1959;31(2):526.
Kurschus et al., Delivery and therapeutic potential of human granzyme B. Immunol Rev. May 2010;235(1):159-71. doi: 10.1111/j.0105-2896.2010.00894.x.
Ling et al., Protein thioester synthesis enabled by sortase. J Am Chem Soc. Jul. 4, 2012;134(26):10749-52. doi:10.1021/ja302354v. Epub Jun. 19, 2012.
Abi-Habib et al., A urokinase-activated recombinant anthrax toxin is selectively cytotoxic to many human tumor cell types. Mol Cancer Ther. Oct. 2006;5(10):2556-62.
Arora et al., Fusions of anthrax toxin lethal factor to the ADP-ribosylation domain of Pseudomonas exotoxin A are potent cytotoxins which are translocated to the cytosol of mammalian cells. J Biol Chem. Aug. 5, 1992;267(22):15542-8.
Arora et al., Fusions of anthrax toxin lethal factor with shiga toxin and diphtheria toxin enzymatic domains are toxic to mammalian cells. Infect Immun. Nov. 1994;62(11):4955-61.
Barth, Exploring the role of host cell chaperones/PPIases during cellular up-take of bacterial ADP-ribosylating toxins as basis for novel pharmacological strategies to protect mammalian cells against these virulence factors. Naunyn Schmiedebergs Arch Pharmacol. Mar. 2011;383(3):237-45. doi:10.1007/s00210-010-0581-y. Epub Dec. 1, 2010.
Basilio et al., Evidence for a proton-protein symport mechanism in the anthrax toxin channel. J Gen Physiol. Mar. 2009;133(3):307-14. doi: 10.1085/jgp.200810170. Epub Feb. 9, 2009.
Blanke et al., Fused polycationic peptide mediates delivery of diphtheria toxin A chain to the cytosol in the presence of anthrax protective antigen. Proc Natl Acad Sci U S A. Aug. 6, 1996;93(16):8437-42.
Bradley et al., Anthrax toxin receptor proteins. Biochem Pharmacol. Feb. 1, 2003;65(3):309-14.
Bradley et al., Identification of the cellular receptor for anthrax toxin. Nature. Nov. 8, 2001;414(6860):225-9.
Brockwell et al., Pulling geometry defines the mechanical resistance of a beta-sheet protein. Nat Struct Biol. Sep. 2003;10(9):731-7. Epub Aug. 17, 2003. Erratum in: Nat Struct Biol. Oct. 2003;10(10):872.

(56) References Cited

OTHER PUBLICATIONS

Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.

Collier, Membrane translocation by anthrax toxin. Mol Aspects Med. Dec. 2009;30(6):413-22. doi: 10.1016/j.mam.2009.06.003. Epub Jun. 27, 2009.

Dintzis et al., A comparison of the immunogenicity of a pair of enantiomeric proteins. Proteins. Jul. 1993;16(3):306-8.

\* cited by examiner

FIG. 3A

| | EC50 (pM) |
|---|---|
| ■ LF$_N$-DTA | 27 |
| ○ STv1 | 37 |
| ▲ STv2 | 35 |
| ▽ STv3 | 31 |
| ◄ STv4 | 31 |
| ▷ STv5 | 48 |
| ◇ STv6 | 24 |
| ○ LF$_N$-DTA, No PA | |
| ○ STv1, No PA | |

FIG. 3B

| | EC50 (pM) |
|---|---|
| ■ LF$_N$DTA | 0.5 |
| ○ STv7 | 1.7 |
| △ STv8 | 21.6 |
| ▽ STv9 | 9.6 |

FIG. 4A

| | EC50 (pM) |
|---|---|
| LF$_N$-DTA | 19 |
| STv10 | 27 |
| STv11 | 25 |
| STv12 | 56 |
| STv13 | 33 |

FIG. 4B

| | EC50 (pM) |
|---|---|
| LF$_N$DTA | 0.5 |
| STv14 | 5 |

Sortagged variant    C-terminal peptide modification

STv1

STv2

STv3

STv4

STv5

STv6

STv7

STv8      STv9

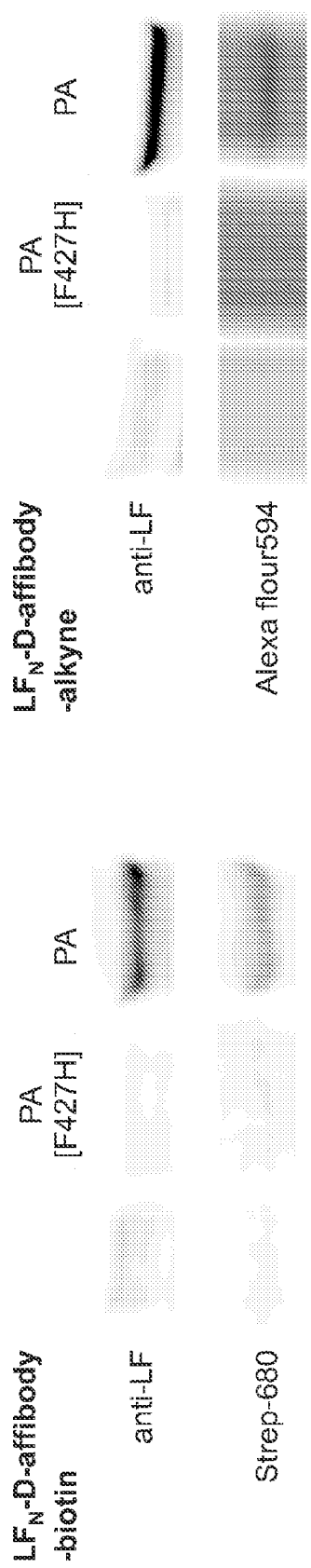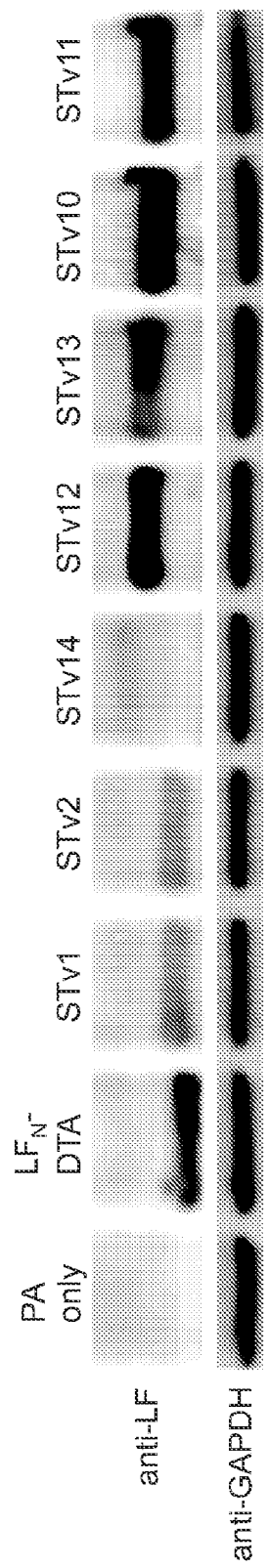
FIG. 12D
FIG. 12E

SEQUENCE LISTING

<160> NUMBER OF SEQ ID NOS: 48

<210> SEQ ID NO 1
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any amino acid

<400> SEQUENCE: 1

Gly Gly Gly Xaa
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any amino acid

<400> SEQUENCE: 2

Gly Gly Gly Gly Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any amino acid

<400> SEQUENCE: 3

Gly Gly Gly Gly Gly Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any amino acid

<400> SEQUENCE: 4

Gly Gly Gly Gly Gly Gly Xaa
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature

```
<222> LOCATION: (4)..(4)
<223> OTHER INFORMATION: Xaa is Gly, Phe, Ser or Leu

<400> SEQUENCE: 5

Gly Gly Gly Xaa
1

<210> SEQ ID NO 6
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is Gly, Phe, Ser or Leu

<400> SEQUENCE: 6

Gly Gly Gly Gly Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Gly, Phe, Ser or Leu attached to a
      thioester

<400> SEQUENCE: 7

Gly Gly Gly Gly Gly Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is 1-6 amino acids wherein each amino acid
      is any amino acid, naturally occurring or non-naturally occurring

<400> SEQUENCE: 8

Gly Gly Gly Gly Gly Gly Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Gly attached to a non-amino acid entity
      attached to a thioester

<400> SEQUENCE: 9

Gly Gly Gly Gly Xaa
1               5
```

```
<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Gly attached to a non-amino acid entity
      attached to a thioester

<400> SEQUENCE: 10

Gly Gly Gly Gly Gly Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Gly attached to a non-amino acid entity
      attached to a thioester

<400> SEQUENCE: 11

Gly Gly Gly Gly Gly Gly Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any amino acid

<400> SEQUENCE: 12

Leu Pro Xaa Thr Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(8)
<223> OTHER INFORMATION: X1, 3, 5, 7 are each any negatively charged
      amino acids, X2, 4, 6, 8 are each any positively charged amino
      acid

<400> SEQUENCE: 13

Xaa Xaa Xaa Xaa Xaa Xaa Xaa Xaa
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (1)..(8)
<223> OTHER INFORMATION: X1, 3, 5, 7 are each any positively charged
      amino acid, X2, 4, 6, 8 are each any negatively charged amino acid

<400> SEQUENCE: 14

Xaa Xaa Xaa Xaa Xaa Xaa Xaa Xaa
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 15

Leu Pro Ser Thr Gly Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to LFn-DTA

<400> SEQUENCE: 16

Xaa Pro Ser Thr Gly Gly
1               5

<210> SEQ ID NO 17
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(16)
<223> OTHER INFORMATION: all L

<400> SEQUENCE: 17

Gly Gly Gly Gly Gly Ala Lys Phe Arg Pro Asp Ser Asn Val Arg Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(16)
<223> OTHER INFORMATION: all D

<400> SEQUENCE: 18

Gly Gly Gly Gly Gly Ala Lys Phe Arg Pro Asp Ser Asn Val Arg Gly
1               5                   10                  15

<210> SEQ ID NO 19
<211> LENGTH: 16
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Wherein Xaa is beta-Ala

<400> SEQUENCE: 19

Gly Gly Gly Gly Gly Xaa Lys Phe Arg Pro Asp Ser Asn Val Arg Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Wherein Xaa is N-Me-Ala

<400> SEQUENCE: 20

Gly Gly Gly Gly Gly Xaa Lys Phe Arg Pro Asp Ser Asn Val Arg Gly
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Wherein Xaa is proparl-Gly

<400> SEQUENCE: 21

Gly Gly Gly Gly Gly Xaa Lys Phe Arg Pro Asp Ser Asn Val Arg Gly
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (8)..(8)
<223> OTHER INFORMATION: Wherein Xaa is Tri-Fluoro-F

<400> SEQUENCE: 22

Gly Gly Gly Gly Gly Ala Lys Xaa Arg Pro Asp Ser Asn Val Arg Gly
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 23

Gly Gly Gly Gly Gly Ala Lys Cys Arg Pro Asp Ser Asn Val Arg Gly
1               5                   10                  15

<210> SEQ ID NO 24
```

```
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (16)..(16)
<223> OTHER INFORMATION: Xaa is Gly attached to a thioester

<400> SEQUENCE: 24

Gly Gly Gly Gly Gly Ala Lys Cys Arg Pro Asp Ser Asn Val Arg Xaa
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (16)..(16)
<223> OTHER INFORMATION: Xaa is Gly attached to a thioester

<400> SEQUENCE: 25

Gly Gly Gly Gly Gly Ala Lys Cys Arg Pro Asp Ser Asn Val Arg Xaa
1               5                   10                  15

<210> SEQ ID NO 26
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is Gly attached to a thioester

<400> SEQUENCE: 26

Gly Gly Gly Gly Xaa
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is Gly attached to a thioester

<400> SEQUENCE: 27

Gly Gly Gly Gly Xaa
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is Gly attached to GB1

<400> SEQUENCE: 28
```

```
Gly Gly Gly Gly Xaa
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is Gly attached to GB1

<400> SEQUENCE: 29

Gly Gly Gly Gly Xaa
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is Gly attached to FN3

<400> SEQUENCE: 30

Gly Gly Gly Gly Xaa
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to LFN

<400> SEQUENCE: 31

Xaa Pro Ser Thr Gly Gly
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to LFN-DTA

<400> SEQUENCE: 32

Xaa Pro Ser Thr Gly Gly
1               5

<210> SEQ ID NO 33
<211> LENGTH: 11
<212> TYPE: PRT
<213> ORGANISM: Artificial Sequence
<220> FEATURE:
<223> OTHER INFORMATION: Synthetic Polypeptide
```

<400> SEQUENCE: 33

Gly Gly Gly Gly Gly Leu Arg Lys Ala Arg Leu
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to LFN-DTA

<400> SEQUENCE: 34

Xaa Pro Ser Thr Gly Gly His
1               5

<210> SEQ ID NO 35
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 35

Gly Gly Gly Gly Gly Leu Arg Arg Leu Arg Ala Cys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to eGFP

<400> SEQUENCE: 36

Xaa Pro Ser Thr Gly Gly His His His His His His
1               5                   10

<210> SEQ ID NO 37
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa is Gly attached to LRL-CONH2

<400> SEQUENCE: 37

Gly Gly Gly Xaa
1

<210> SEQ ID NO 38
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature

```
<222> LOCATION: (6)..(6)
<223> OTHER INFORMATION: Xaa is His attached to SrtA*

<400> SEQUENCE: 38

His His His His His Xaa
1               5

<210> SEQ ID NO 39
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to eGFP

<400> SEQUENCE: 39

Xaa Pro Ser Thr Gly Gly Gly Gly Gly Leu Arg Leu
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 40

Gly Gly Gly Gly Gly Leu Arg Leu
1               5

<210> SEQ ID NO 41
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to LFN

<400> SEQUENCE: 41

Xaa Pro Ser Thr Gly Gly His His His His His His
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to LFN
<220> FEATURE:
<221> NAME/KEY: misc_feature
<222> LOCATION: (9)..(9)
<223> OTHER INFORMATION: Xaa is Gly attached to affibody

<400> SEQUENCE: 42

Xaa Pro Ser Thr Gly Gly Gly Gly Xaa
1               5

<210> SEQ ID NO 43
<211> LENGTH: 5
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is Gly attached to fibronectin 3

<400> SEQUENCE: 43

Gly Gly Gly Gly Xaa
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to LFN
<220> FEATURE:
<221> NAME/KEY: misc_feature
<222> LOCATION: (9)..(9)
<223> OTHER INFORMATION: Xaa is Gly attached to fibronectin 3

<400> SEQUENCE: 44

Xaa Pro Ser Thr Gly Gly Gly Gly Xaa
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is Gly attached to 2Dpico

<400> SEQUENCE: 45

Gly Gly Gly Gly Xaa
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to LFN
<220> FEATURE:
<221> NAME/KEY: misc_feature
<222> LOCATION: (9)..(9)
<223> OTHER INFORMATION: Xaa is Gly attached to 2Dpico

<400> SEQUENCE: 46

Xaa Pro Ser Thr Gly Gly Gly Gly Xaa
1               5

<210> SEQ ID NO 47
<211> LENGTH: 6
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to A-F

<400> SEQUENCE: 47

Xaa Pro Ser Thr Gly Gly
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu attached to A-F
<220> FEATURE:
<221> NAME/KEY: misc_feature
<222> LOCATION: (9)..(9)
<223> OTHER INFORMATION: Xaa is Gly attached to COSR

<400> SEQUENCE: 48

Xaa Pro Ser Thr Gly Gly Gly Gly Xaa
1               5
```

TRANSLOCATION OF NON-NATURAL CHEMICAL ENTITIES THROUGH ANTHRAX PROTECTIVE ANTIGEN PORE

RELATED APPLICATIONS

This application is a national stage filing under U.S.C. §371 of PCT International Application PCT/US2013/042118, filed May 21, 2013, which claims priority under 35 U.S.C. §119(e) to U.S. Provisional Application Ser.No. 61/649,421, entitled "TRANSLOCATION OF NON-NATURAL CHEMICAL ENTITIES THROUGH ANTHRAX PROTECTIVE ANTIGEN PORE,"filed on May 21, 2012 and to U.S. Provisional Application Ser. No. 61/649,866, entitled "PROTEIN RETROSPLICING ENABLED BY A DOUBLE LIGATION REACTION," filed on May 21, 2012, which are herein incorporated by reference in their entirety.

FIELD OF THE INVENTION

A versatile platform for delivery of biomolecules to the cytosol of cells is provided according to the invention.

BACKGROUND OF INVENTION

The delivery of proteins to the cytosol has been difficult to achieve due to the barrier of the plasma membrane or the inefficiency of endosomal release, while many bacterial toxins have evolved the machineries to transport their catalytic components to the cytosol of mammalian cells. Anthrax toxin is one example that uses three components[1]: the translocase protective antigen (PA) and two enzymatic factors, Lethal Factor (LF) and Edema Factor (EF)[2]. PA binds to receptors on host cells[3,4] and is cleaved by a furin-family protease[5,6]. The resulting fragment $PA_{63}$ self-assembles to the ring-shaped heptameric and octameric prepore[7,8], forming complexes with LF and EF with high affinity. The complexes are then endocytosed to the endosome, where the acidification triggers the conformational rearrangement of prepore to form an ion-conductive β-barrel transmembrane pore. The pore then translocates LF and EF to the cytosol to act on their selective target proteins[9,10] (FIG. 6). FIG. 6 is a model of anthrax toxin entry into cells.

LF binds to the surface of PA through the 263-residue N-terminal domain ($LF_N$) with nanomolar affinity. The crystal structure of PA8 ($LF_N$)4 prepore complex shows that the first α-helix and β-strand (α1β1) of $LF_N$ unfold and dock into the cleft between two adjacent PA subunits, called a clamp, providing the translocase a key handle to grip the substrate.[11] $LF_N$ is further partially unfolded under the acidic pH in the endo some and its N terminus binds to the hydrophobic heptad of F427 residues in $PA_{63}$ pore, called φ-clamp, initiating the unfolding and translocation of the protein in an N- to C-terminal direction through the narrow β-barrel channel.[12-16]

Both the α clamp and φ-clamp interact with a broad array of amino acid sequences, providing the wide chemical complexity and configurational flexibility to the $PA_{63}$ pore. $LF_N$ fusions of the A chain of diphtheria toxin (DTA), catalytic domains of *pseudomonas* exotoxin A and Shiga toxin,[17,18] and some other proteins have been recombinantly expressed and successfully translocated through $PA_{63}$ pores. A more recent study has shown the effects of incorporation of D-amino acids and cysteic acid at the N-terminus of $LF_N$ on translocation through the pore.[19] The ability of the $PA_{63}$ pore in translocating non-natural chemical entities has not been well exploited.

SUMMARY OF THE INVENTION

Current technologies in targeted small molecule drug delivery are limited. The invention provides a new and improved approach to targeted small molecule and drug delivery. The approach involves in some aspects unique chemical reactions and well-defined final structures.

In some aspects the invention is a method of disrupting a molecular interaction in a living cell, by contacting the living cell with a pore forming protein pore forming protein and a fusion molecule comprising a pore specific delivery protein linked to a reagent, wherein the reagent is delivered to the cytosol of the living cell in an effective amount for disrupting a molecular interaction in the living cell.

In other aspects the invention is a method for delivering a reagent to the cytosol of a targeted living cell, by contacting the targeted living cell with a pore forming protein, wherein the pore forming protein has a cellular target signal, wherein the cellular target signal targets the pore forming protein to the targeted living cell, and a fusion molecule comprising a pore specific delivery protein pore specific delivery protein linked to a reagent, wherein the reagent is delivered to the cytosol of the targeted living cell.

In some embodiments the reagent is a labeled compound, a halogenated compound, a morpholino, a therapeutic RNA, a protein mimic, antibody mimic, a mirror image biomolecule or a monobody, or an engineered protein scaffold.

In yet other aspects the invention is a method for delivering a reagent to the cytosol of a living cell, by contacting the living cell with a pore forming protein and a fusion molecule comprising a pore specific delivery protein pore specific delivery protein linked to a reagent, wherein the reagent is delivered to the cytosol of the living cell in an effective amount to deliver the reagent to the cytosol of the living cell, wherein the reagent is a labeled compound, a halogenated compound, a morpholino, a therapeutic RNA, a protein mimic, antibody mimic, a mirror image biomolecule or a monobody, or an engineered protein scaffold.

The labeled compound may be a peptide labeled with a biotin or a click chemistry reagent. In some embodiments the halogenated compound is a fluorinated peptide. In other embodiments the protein mimic is an antibody mimic.

The reagent in some embodiments is delivered to the cytosol of the living cell in an effective amount for disrupting a molecular interaction in the living cell. The molecular interaction in some embodiments is a protein-protein binding interaction and the reagent inhibits the protein-protein binding. In other embodiments the molecular interaction is a nucleic acid-protein binding interaction and the reagent inhibits the nucleic acid-protein binding. In yet other embodiments the molecular interaction is a protein function and the reagent inhibits the protein function. In other embodiments the molecular interaction is a nucleic acid function and the reagent inhibits the nucleic acid function.

The pore forming protein has a cellular target signal according to some embodiments. The cellular target signal may be a cell surface receptor binding peptide. In some embodiments the cell surface binding peptide is a Her2 binding peptide. In other embodiments the reagent is an antibody mimic, a mirror image biomolecule or a monobody.

A fusion molecule, of a pore specific delivery protein linked to a reagent, wherein the reagent is a labeled compound, a halogenated compound, a morpholino, a therapeutic RNA, a protein mimic, antibody mimic, a mirror image biomolecule or a monobody, or an engineered protein scaffold is provided according to other aspects of the invention. In some embodiments the labeled compound is a peptide labeled with a biotin or a click chemistry reagent. In other embodiments the halogenated compound is a fluorinated peptide.

The invention in other aspects is a method for preparing a fusion molecule, by performing a ligation reaction of a pore specific delivery protein with a peptide thioester in the presence of a SrtA enzyme to produce a pore specific delivery protein —COSR product, and reacting the pore specific delivery protein —COSR product with a C-terminal protein domain, wherein the C-terminal protein domain has a cysteine at the N-termini, to produce a modified protein having a chemical entity linking the pore specific delivery protein and the C-terminal protein domain.

A kit is provided according to other aspects. The kit includes a container housing together or in separate compartments a pore forming protein, a pore specific delivery protein, a peptide thioester and instructions for preparing a fusion protein and delivering the fusion protein to a living cell. In some embodiments the kit further includes a SrtA enzyme.

In some embodiments the peptide thioester is Gn-Xaa-COSR, wherein n is 1-6 and wherein Xaa is any amino acid (SEQ ID NOs: 1-4). In other embodiments the peptide thioester is Gn-Xaa-COSR, wherein n is 3-5 and, wherein Xaa is Gly, Phe, Ser or Leu (SEQ ID NOs: 5-7). In yet other embodiments the peptide thioester is GGGGG-Xaa-COSR, wherein Xaa is Gly, Phe, Ser or Leu (SEQ ID NO: 7). In some embodiments the peptide thioester is Gn-Xm-COSR, wherein n is 1-6, m is 1-6, and wherein X is an amino acid, naturally occurring or non-naturally occurring (SEQ ID NO: 8). X may be a D-amino acid. In yet other embodiments the peptide thioester is Gn-Y-COSR, wherein n is 1-6 and wherein Y is a non-amino acid chemical entity (SEQ ID NO: 9-11). Y may be a PEG unit.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The figures are illustrative only and are not required for enablement of the invention disclosed herein.

FIG. 3 shows translocation of STv1-9 into CHO-K1 cells. (a) Cells were incubated with STv1-6 in the presence or absence of PA for 30 minutes. (b). Cells were incubated with STv7-9 in the presence of PA for 4 hours. Each data point represents the average of three trials.

FIG. 4 shows translocation of STv10-14 into CHO-K1 cells. (a) Cells were incubated with STv10-13 in the presence or absence of PA for 30 minutes. (b). Cells were incubated with STv14 in the presence of PA for 4 hours. Each data point represents the average of three trials.

DESCRIPTION OF INVENTION

Figure 1A:
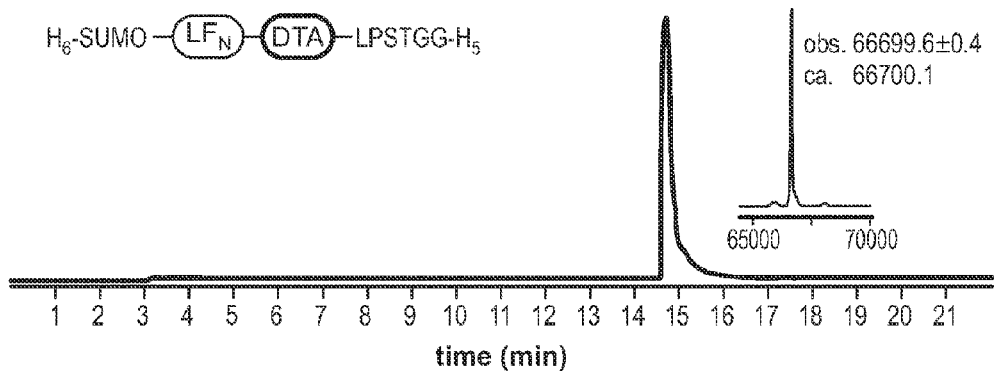
FIG. 1 shows LCMS Characterization of sortagging reactions. Total ion current and deconvoluted mass (inset) of the starting material (a), purified product STv1 (b) and STv2 (c). (d-f) represent the corresponding charge state series.
Figure 1B:
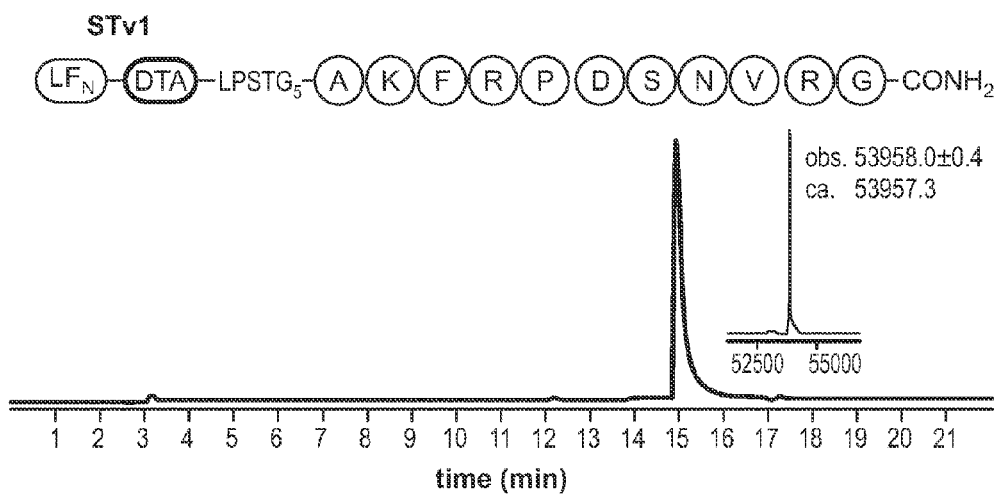
Figure 1C:
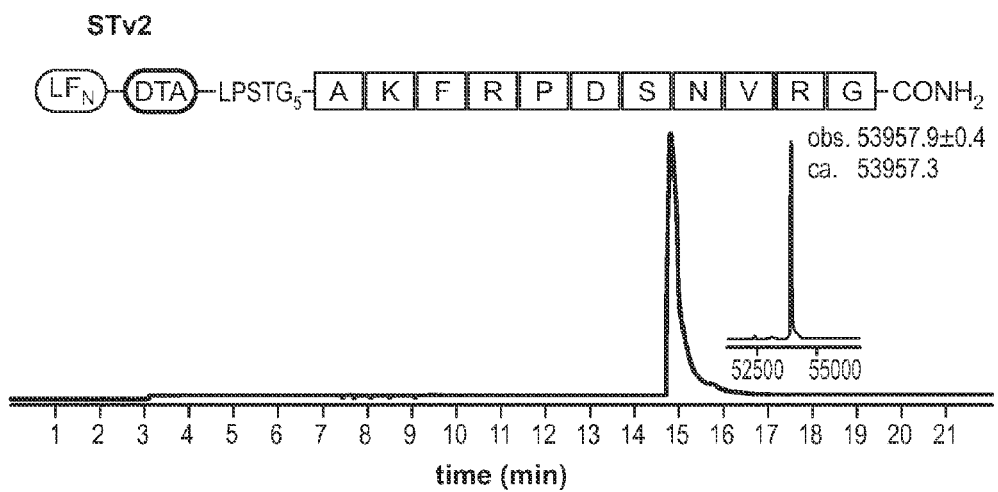
Figure 1D:
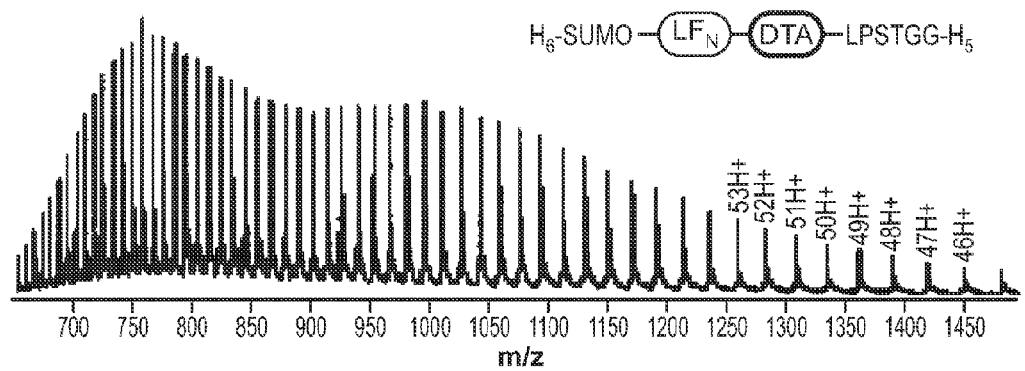
Figure 1E:
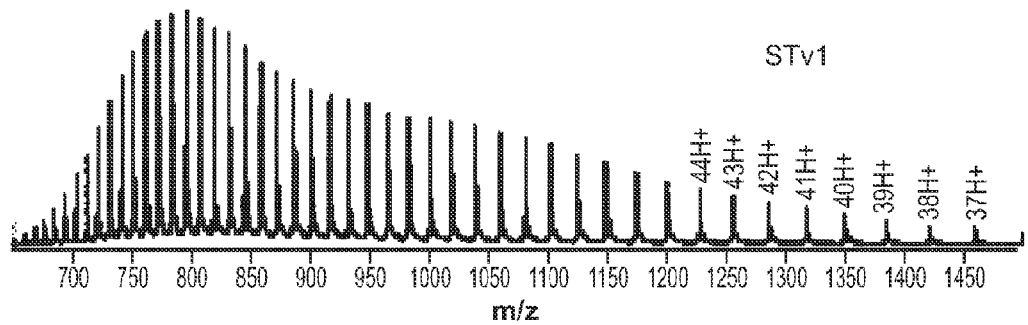
Figure 1F:
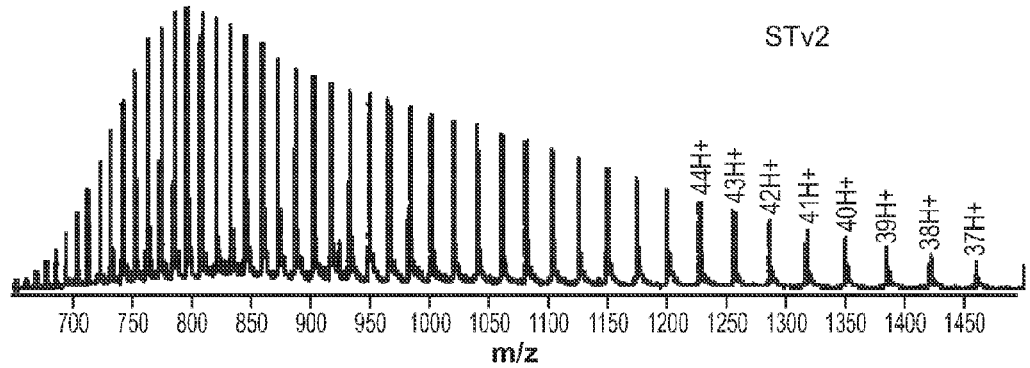
Figure 2A:
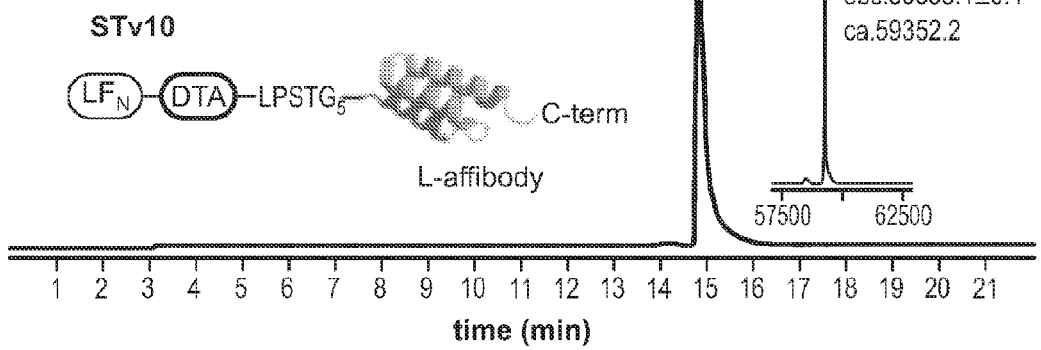
FIG. 2 shows total ion current and deconvoluted mass (inset) of STv9-13 characterized by LCMS.
Figure 2B:
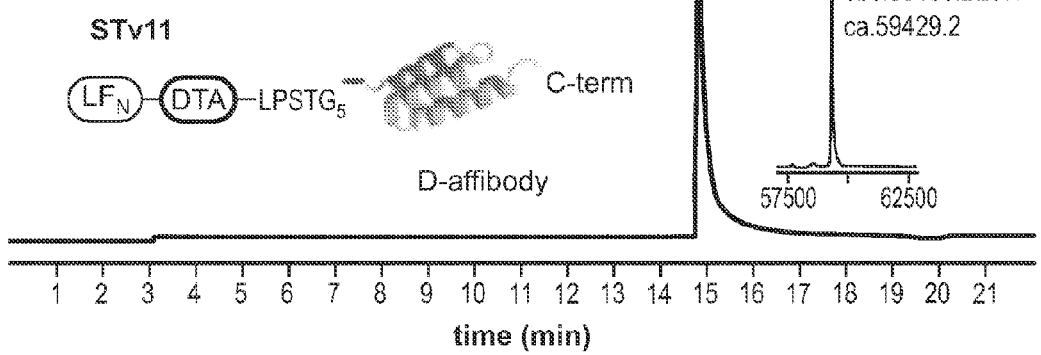
Figure 2C:
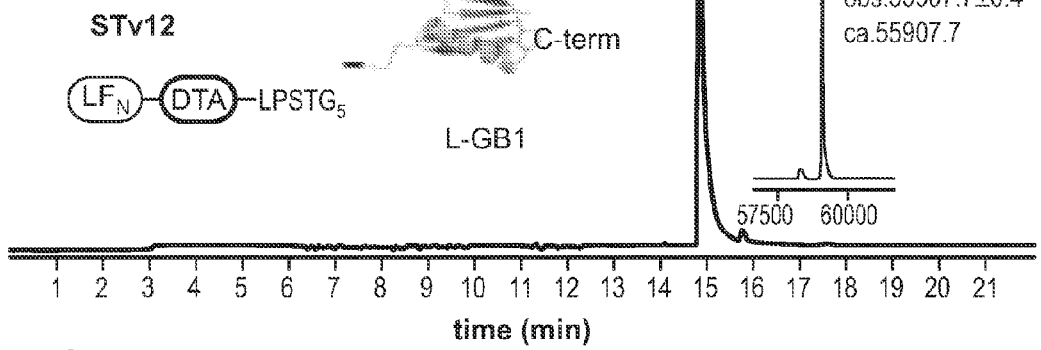
Figure 2D:
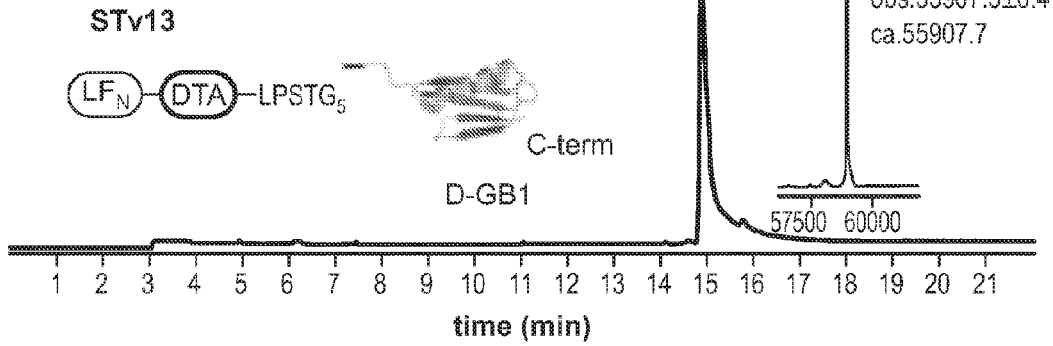

Disclosed is a new approach for delivering compounds and drugs to the cytosol of living cells through the use of engineered protein transporters. The methods involve a pair of reagents (pore forming protein and pore specific delivery protein) that, functioning together, result in the endocytosis and release of a drug or other compound into the cytosol of a cell. The powerful technique can be sued to deliver a wide variety of non-naturally occurring compounds in that cells, that previously faced serious delivery challenges. The methods provided herein provide new opportunities for research, diagnostic and therapeutic treatment. In the examples provided below, we have utilized a highly efficient chemo-enzymatic ligation strategy to load cytotoxic drugs, such as Doxorubicin and Docetaxel onto the pair of reagents, for example, $LF_N$ or PA. Homogeneous and well-defined protein-drug conjugates were obtained in these studies. As the pore forming protein binds to cognate cell surface receptors, it generates an oligomeric prepore, which then undergoes receptor-mediated endocytosis. The delivery peptide then binds to the pre-pore oligomer followed by internalization. This delivery system is advantageous as single round of endocytosis can deliver multiple copies of delivery peptide-drug conjugates. Experiments described herein showed that $LF_N$ conjugated drugs successfully translocate through the pore into the cytosol. The invention also involves the discovery that the methods can be manipulated to achieve target and cell specific delivery. This can be achieved by modifying the pore forming protein to add a targeting component such that it targets cell specific receptors. For example, it was demonstrated in the examples that by modifying the receptor-binding domain of the pore to target HER2 receptors, cytotoxic drugs may be delivered to HER2 expressing BT474 breast cancer cells.

At its most basic, the invention is simple platform to deliver biomolecules to the cell cytosol. The delivery platform is based on a non-toxic form of protein, referred to as a delivery peptide or a pore specific delivery protein, that specifically interacts with a cognate pore forming protein to achieve specific internalization. Cargos to be delivered to a living cell may be covalently linked to the delivery peptide using a transpeptidase sortase A or other chemical reaction. Once delivered to the cell that has been loaded with pore forming protein the cargo and delivery peptide are transported to the cell cytosol in the presence of protective antigen.

This versatile delivery platform opens new opportunities for research and drug delivery. In the research setting the methods enable the study of the effects of compounds on intracellular processes, where it was not previously possible because the compounds could not be delivered to the interior of the cell in an appropriate format or with a label.

Thus, the invention, in some aspects is a method for delivering a reagent to the interior of a living cell. The cell may be any type of living cell. For example living cells include eukaryotic cells and prokaryotic cells. Examples of living cells include but are not limited to cells derived from humans, primates, dogs, cats, horses, cows, pigs, turkeys, goats, fish, monkeys, chickens, rats, mice, sheep, plants, bacteria, algae, and yeast. The cells may be normal cells, cancerous cells or genetically engineered cells.

The reagent is any type of small molecule. In some embodiments the reagent is a non-naturally occurring small molecule. A non-naturally occurring small molecule as used herein refers to a molecule that is distinct from a naturally occurring molecule in that it has a sequence that is not found in nature, includes one or more non-natural species or entities, or is truncated from a naturally occurring version of a molecule that is found in nature. A molecule that has a sequence that is not found in nature may be, for instance, a peptide or nucleic acid that has a unique amino acid or nucleotide sequence. The unique amino acid or nucleotide sequence may be a sequence which is similar to a naturally occurring sequence but that differs from the naturally occurring sequence by as little as a single unit. A single unit difference may be a different amino acid or nucleotide or it may be a modified version of the naturally occurring amino acid or nucleotide or is may be a labeled version. A labeled version, for instance might be a nucleotide backbone modification, such as a phosphorothioate linkage or an additional molecule such as a methyl group or a halogen.

A non-natural species or entity, as used herein refers to a compound that is not ordinarily found in a specific position within the protein of interest. Non-natural entities, may therefore include naturally occurring amino acids, as long as it is not the amino acid normally found at that specific position within a protein. A non-natural species or entity is also referred to herein as Xaa or Xm and includes but is not limited to naturally occurring amino acids, non-naturally occurring amino acids, such as D-form amino acids, labeled probes, peptidomimetics, and PEG units. The insertion of the entity will depend on the installation of the appropriate reaction partners. In certain embodiments, the non-natural species or entity is one or more heme groups, rhodopsin molecules, vitamins, biotins, fatty acids, lipids, carbohydrates, polymers, or inorganic elements, ions, or clusters.

Small molecules include but are not limited to peptides, nucleic acids, polysaccharide, and low molecular weight organic compound, typically below 800 Daltons. Small molecules are capable of binding to a biopolymer such as a protein, nucleic acid or polysaccharide and altering the activity or function of the biopolymer.

In some instances the reagent is a peptide. A peptide or protein or polypeptide, as used herein, refers to a polymer of at least two monomers, wherein the monomers are amino acids, sometimes referred to as amino acid residues, which are joined together via an amide bond. For purposes of this invention, the terms "peptide," "polypeptide," and "protein," are largely interchangeable as all three types can be used in aspects of the methods described herein.

As used herein, the term amino refers to an amino acid having protected or unprotected side chains. Amino acids include the L and D isoforms of chiral amino acids. An amino acid sequence set forth herein, such as "LPXTG" (SEQ ID NO: 12) orders the amino acid residues from the N-terminus to the C-terminus in a left-to-right manner, unless otherwise indicated from the context. As used herein, the term "side chain" refers to the substituent at the α-carbon atom of an amino acid.

Examples of reagents of the invention include therapeutic molecules such as drugs or drug analogs, labeled compounds, therapeutic or inhibitory nucleic acids, halogenated compounds, protein mimics, antibody mimics, mirror image biomolecules, monobodies, and/or engineered protein scaffolds.

A halogenated compound is a compound that has been modified to include one or more halogen molecules. For instance, compounds which have been fluorinated or chlorinated are halogenated compounds.

Antibody mimics or mimetics are organic compounds that, like antibodies, can specifically bind antigens, but that are not structurally related to antibodies. These compounds, which maybe peptides, nucleic acids, small molecules, or combinations thereof have some advantages over antibodies, such as better solubility, tissue penetration, and stability towards heat and enzymes. Some examples of antibody mimics include but are not limited to affibody molecules (scaffold is Z domain of protein A), Affilins (scaffold is Gamma-B crystalline Ubiquitin), Affitins (scaffold is Sac7d (from *Sulfolobus acidocaldarius*)), Anticalins (scaffold is Lipocalins), Avimers (scaffold is domains of various membrane receptors), DARPins (scaffold is Ankyrin repeat motif), Fynomers (scaffold is SH3 domain of Fyn), Kunitz domain peptides (scaffold is Kunitz domains of various protease inhibitors), and monobodies (scaffold is 10th type III domain of fibronectin).

In some instances the reagent is a nucleic acid. Nucleic acids useful in the methods of the invention include, morpholinos, antisense nucleic acids, RNA interference (RNAi) and/or microRNA (miRNA) pathways including small interfering RNA (siRNA), short hairpin RNA (shRNA), double-stranded RNA (dsRNA), miRNAs, and other small interfering nucleic acid-based molecules known in the art. In one embodiment, vector-based RNAi modalities (e.g., shRNA or shRNA-mir expression constructs) are used to reduce expression of a gene (e.g., a target nucleic acid) in a cell. In some embodiments, therapeutic compositions of the invention comprise an isolated plasmid vector (e.g., any isolated plasmid vector known in the art or disclosed herein) that expresses a small interfering nucleic acid such as an shRNA. The isolated plasmid may comprise a specific promoter operably linked to a gene encoding the small interfering nucleic acid. In some cases, the isolated plasmid vector is packaged in a virus capable of infecting the individual. Exemplary viruses include adenovirus, retrovirus, lentivirus, adeno-associated virus, and others that are known in the art and disclosed herein.

A broad range of RNAi-based modalities could be employed to inhibit expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluyl nucleotides maintain gene silencing activity (Xia et al., ASC Chem. Biol. 1(3): 176-83, (2006)). siRNAs with amide-linked oligoribonucleosides have been generated that are more resistant to S1 nuclease degradation than unmodified siRNAs (Iwase R et al. 2006 Nucleic Acids Symp Ser 50: 175-176). In addition, modification of siRNAs at the 2'-sugar position and phosphodiester linkage confers improved serum stability without loss of efficacy (Choung et al., Biochem. Biophys. Res. Commun. 342(3):919-26, 2006). Other molecules that can be used to inhibit expression of a gene (e.g., a CSC-associated gene) include sense and antisense nucleic acids (single or double stranded), ribozymes, peptides, DNA-zymes, peptide nucleic acids (PNAs), triple helix forming oligonucleotides, antibodies, and aptamers and modified form(s) thereof directed to sequences in gene(s), RNA transcripts, or proteins.

Morpholinos are oligonucleotides that are used to modify gene expression. The mechanism used by morpholinos involves a blocking of small (~25 base) regions of the base-pairing surfaces of RNA typically to knock down gene function. Morpholino oligos specifically binds to a selected target site and block access of cell components to that target site. As a result this class of molecules can be used to block translation, splicing, miRNAs or their targets, and ribozyme activity. For example, by sterically blocking the translation initiation complex, morpholinos can knock down expression of many target sequences.

Other nucleic acid molecules that can be used include sense and antisense nucleic acids (single or double stranded). Antisense nucleic acids include modified or unmodified RNA, DNA, or mixed polymer nucleic acids, and primarily function by specifically binding to matching sequences resulting in modulation of peptide synthesis (Wu-Pong, November 1994, BioPharm, 20-33). Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, Crit. Rev. in Oncogenesis 7, 151-190).

As used herein, the term "antisense nucleic acid" describes a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

In some embodiments the inhibitory nucleic acid of the invention is 100% identical to the nucleic acid target. In other embodiments it is at least 99%, 95%, 90%, 85%, 80%, 75%, 70%, or 50% identical to the nucleic acid target. The term "percent identical" refers to sequence identity between two nucleotide sequences. Percent identity can be determined by comparing a position in each sequence which may be aligned for purposes of comparison. Expression as a percentage of identity refers to a function of the number of identical amino acids or nucleic acids at positions shared by the compared sequences. Various alignment algorithms and/or programs may be used, including FASTA, BLAST, or ENTREZ-FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

An inhibitory nucleic acid useful in the invention will generally be designed to have partial or complete complementarity with one or more target genes. "Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. As an example, the efficiency of inhibition may be determined by assessing the amount of gene product in the cell: mRNA may be detected with a hybridization probe having a nucleotide sequence outside the region used for the inhibitory nucleic acid, or translated polypeptide may be detected with an antibody raised against the polypeptide sequence of that region.

The reagent may also be a labeled compound. A labeled compound is any small molecule, naturally occurring or non-naturally occurring that includes a detectable label. A detectable label as used herein is a moiety, the presence of which can be ascertained directly or indirectly. In some instances, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., biotin, avidin, epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Labels include any known labels that can be used with imaging techniques, such as PET isotopes, scintigraphy, NMR, etc. Other detectable labels include radioactive isotopes such as $^{32}P$ or $^{3}H$, luminescent markers such as fluorochromes, optical or electron density markers, etc., or epitope tags such as the FLAG epitope or the HA epitope, biotin, avidin, and enzyme tags such as horseradish peroxidase, β*-galactosidase, nanoparticles, etc. There are many different labels and methods of labeling known to those of ordinary skill in the art. Examples of the types of labels that can be used in the present invention include binding partners (biotin-avidin), enzymes, radioisotopes, fluorescent compounds, colloidal metals, nanoparticles, chemiluminescent compounds, and bioluminescent compounds.

The reagent may be an L-protein or a D-protein. Additionally, the reagent may be a cyclic peptide. In some embodiments the reagent is not an D-protein or a cyclic peptide.

Since the mechanisms involved in intracellular transport using naturally occurring pore-delivery protein pairs is typically sequence specific, it was unexpected that molecules or reagents that are so distinct from the delivery peptide could be attached to the delivery peptide without disrupting the process of intracellular delivery. The data presented below establishes that widely diverse types of small molecules can be successfully delivered to the cytosol of the cell and, importantly, are functional within the cell. The system of the invention may therefore be used to introduce reagents into the cell to produce a wide variety of functions in the cell.

The methods of the invention may be used, for example, to disrupt a molecular interaction in the cell. A molecular interaction is any type of function by a molecule in a cell. The function may be based on a single molecule. For instance a molecule such as mRNA may be present within the cell. The system of the invention maybe used to deliver a therapeutic RNA, DNA, morpholino, or protein to the cell which will interact with, either directly or indirectly, and interfere with function, stability, access to or translation of that mRNA. Similarly, the system of the invention may be used to disrupt the function of a cellular protein. For instance, the protein may be an enzyme. A reagent may be delivered to the cytosol of the cell wherein the reagent is a molecule that disrupts the enzymatic activity by disrupting a component of the enzyme that maintains stability or proper folding of the enzyme. The function or intracellular interaction may also involve two or more cellular components. For example the molecular interaction may a protein-protein binding interaction. The disruption of the molecular interaction may be achieved by the cytosolic delivery of a reagent that inhibits the protein-protein binding, either directly or indirectly. Alternatively, the molecular interaction may a nucleic acid-protein binding interaction. The disruption of the molecular interaction may be achieved by the cytosolic delivery of a reagent that inhibits the nucleic acid-protein binding, either directly or indirectly.

The reagents may bind directly to a cytosolic molecule, preferably in a selective manner. As used herein, the terms "selective binding" and "specific binding" are used interchangeably with respect to reagents to refer to the ability of the reagent to bind with greater affinity to the target cytosolic molecule than to other molecules. That is, reagents that bind selectively to target cytosolic molecule will not bind to other molecules to the same extent and with the same affinity as they bind to target cytosolic molecules. In some embodiments, the reagents of the invention bind solely to target cytosolic molecules. As used herein, a binding reagent that binds selectively or specifically to target cytosolic molecule will bind with lesser affinity (if at all) to other molecules. Lesser affinity may include at least 10% less, 20% less, 30% less, 40% less, 50% less, 60% less, 70% less, 80% less, 90% less, or 95% less.

The methods may be achieved by contacting the living cell with a pore forming protein and a fusion molecule comprising a pore specific delivery protein linked to a reagent. A pore forming protein, as used herein is peptide that is capable of self-assembling into a ring-shaped oligomeric form (for example a heptameric or octameric oligomer) to form a pore in the cell membrane.

The pore forming protein is capable of binding to a pore specific delivery protein. The pore forming protein forms complexes with the pore specific delivery protein which is attached to a reagent. Once the complex is formed the pore specific delivery protein-reagent is endocytosed. Acidification of the endosome triggers a conformational rearrangement of the pore forming protein oligomer to a translocase that unfolds and passes the pore specific delivery protein-reagent to the cytosol.

Naturally occurring examples of sets of pore forming protein s and pore specific delivery protein exist. For example many bacterial toxins include a pore forming protein and a pore specific delivery protein, either together within a single protein or in separate proteins that function together. Diphtheria toxin, for example, is a single protein containing both a pore forming protein and a pore specific delivery protein. In contrast, anthrax toxin is composed of multiple peptides which make up the pore forming protein (referred to as protective antigen or PA in anthrax toxin) and a pore specific delivery protein (edema factor (EF) or lethal factor (LF) in anthrax toxin). Naturally occurring toxins that include these peptides useful in the methods of the invention include but are not limited to anthrax toxin, diphtheria toxin, pertussis toxin, cholera toxin, botulinum neurotoxin, shiga toxin, shiga like toxin, *pseudomonas* exotoxin, tetanus toxin, and exotoxin A. The pore forming protein may be a naturally occurring toxin pore forming protein or may be a modified pore forming protein, that includes one or more non-naturally occurring entities.

The pore specific binding peptide is a peptide that interacts with a pore in a manner that enables transport of the peptide and any related attached cargo through the pore. While the pore specific binding peptide interacts with the pore sequence a variety of peptide sequences that vary from the naturally occurring sequence can be used. Thus, the pore specific binding peptide may be a fragment of a naturally occurring toxin, a variant thereof or a synthetic peptide sequence. An exemplary pore specific binding peptide has an amino acid sequence comprising:

$X_1$-$Y_1$-$X_2$-$Y_2$-$X_3$-$Y_3$-$X_4$-$Y_4$ (SEQ ID NO: 13)
or
$Y_1$-$X_1$-$Y_2$-$X_2$-$Y_3$-$X_3$-$Y_4$-$X_4$ (SEQ ID NO: 14)

wherein X is a negatively charged amino acid and Y is a positively charged amino acid. In some embodiments, $X_1$, $X_2$, $X_3$, and $X_4$ are selected from E and D or D-amino acid isoforms of E and D. In other embodiments $Y_1$, $Y_2$, $Y_3$, and $Y_4$ are selected from K, R, and H, or D-amino acid isoforms of K, R, and H. In some embodiments the pore specific binding peptide is a peptide of 8-50 amino acids in length. Alternatively, the peptide may be 10-40, 15-30, or 20-25 amino acids in length. Examples of pore specific binding peptides of the invention include the following:

The various reagents can be synthesized using known recombinant and ligation techniques. Alternatively, the reagents may be prepared using a novel technique, fully described in co-pending U.S. patent application No. 61/649,866 and PCT application claiming priority to U.S. patent application No. 61/649,866, filed concurrently herewith, each of which is incorporated by reference in its entirety. The methods described therein include novel methods for ligating peptide sequences in a rapid and high-throughput manner. The products produced are multiple compounds linked together either directly or through a linker. The pore specific binding peptide may be coupled to the reagent using this methodology.

A linker may be used to connect the pore specific binding peptide and the reagent. The linker may optionally be susceptible to cleavage in the cytosolic compartment. Linker molecules ("linkers") may be peptides, which consist of one to multiple amino acids, or non-peptide molecules. Examples of peptide linker molecules useful in the invention include glycine-rich peptide linkers (see, e.g., U.S. Pat. No. 5,908,626), wherein more than half of the amino acid residues are glycine. Preferably, such glycine-rich peptide linkers consist of about 20 or fewer amino acids.

Linker molecules may also include non-peptide or partial peptide molecules. For instance the peptide may be linked to other molecules using well known cross-linking molecules such as glutaraldehyde or EDC (Pierce, Rockford, Ill.). Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage. General methods for cross-linking molecules have been reviewed (see, e.g., Means and Feeney, Bioconjugate Chem., 1: 2-12 (1990)).

Homobifunctional cross-linker molecules have two reactive sites which are chemically the same. Examples of homobifunctional cross-linker molecules include, without limitation, glutaraldehyde; N,N'-bis(3-maleimido-propionyl-2-hydroxy-1,3-propanediol (a sulfhydryl-specific homobifunctional cross-linker); certain N-succinimide esters (e.g., discuccinimyidyl suberate, dithiobis(succinimidyl propionate), and soluble bis-sulfonic acid and salt thereof (see, e.g., Pierce Chemicals, Rockford, Ill.; Sigma-Aldrich Corp., St. Louis, Mo.).

Preferably, a bifunctional cross-linker molecule is a heterobifunctional linker molecule, meaning that the linker has at least two different reactive sites, each of which can be separately linked to a peptide or other molecule. Use of such heterobifunctional linkers permits chemically separate and stepwise addition (vectorial conjunction) of each of the reactive sites to a selected peptide sequence. Heterobifunctional linker molecules useful in the invention include, without limitation, m-maleimidobenzoyl-N-hydroxysuccinimide ester (see, Green et al., Cell, 28: 477-487 (1982); Palker et al., Proc. Natl. Acad. Sci (USA), 84: 2479-2483 (1987)); m-maleimido-benzoylsulfosuccinimide ester; maleimidobutyric acid N-hydroxysuccinimide ester; and N-succinimidyl 3-(2-pyridyl-dithio)propionate (see, e.g., Carlos et al., Biochem. J., 173: 723-737 (1978); Sigma-Aldrich Corp., St. Louis, Mo.).

When it is desirable to deliver the reagent to a specific cell, the reagent may be targeted to a specific type of cell or tissue. Typically, the pore forming protein is bound to a cellular target signal. A cellular target signal as used herein is a molecule which specifically recognizes and binds to a cell surface molecule associated with a specific type of cell or tissue. For example the cellular target signal may recognize and bind to a cell surface receptor and as such is referred to as a cell surface receptor binding peptide. Cell surface binding peptides include but are not limited to peptides that bind Her2, tumor necrosis factor receptor (TNFR), cytotoxic T lymphocyte antigen 4 (CTLA4), programmed cell death protein 1 (PD1), B- and T lymphocyte attenuator (BTLA), lymphocyte activation gene 3 (LAG3), CD160, PD1 homolog (PD1H), CD28, inducible co-stimulator (ICOS), CD137 (also known as 4-1BB), CD27, OX40, glucocorticoid-induced TNFR-related protein (GITR), CD40 ligand (CD40L), B cell activation factor receptor (BAFFR), transmembrane activator, CAML interactor (TACI), B cell maturation antigen (BCMA), B7 ligand members, APRIL, a proliferation-inducing ligand; B7H1, B7 homolog 1; GITRL, GITR ligand; HVEM, herpesvirus entry mediator; ITAM, immunoreceptor tyrosine-based activation motif; ITIM, immunoreceptor tyrosine-based inhibitory motif; ITSM, immunoreceptor tyrosine-based switch motif; MHC, major histocompatibility complex; OX40L, OX40 ligand; PI3K, phosphoinositide 3-kinase; TCR, T cell receptor; TRAF, or TNFR-associated factor binding peptide.

The invention also relates to compositions that are useful according to the methods of the invention. An exemplary composition of the invention is a fusion molecule of a pore specific delivery protein linked to a reagent, wherein the reagent is a labeled compound, a halogenated compound, a morpholino, a therapeutic RNA, a protein mimic, antibody mimic, a mirror image biomolecule or a monobody, or an engineered protein scaffold.

The peptide for instance, may be linked to a PEG molecule. Such a molecule is referred to as a PEGylated peptide.

Another composition of the invention is a pore forming protein conjugated to a cellular target signal. The composition may be in the form of a peptide or a nucleic acid expressing the peptide. For instance the composition may be a nucleic acid expression vector including the elements for expressing the pore forming protein conjugated to a cellular target signal. A variety of suitable vectors are available for expressing genetic material in cells. The selection of an appropriate vector to deliver a therapeutic agent for a particular condition and the optimization of the conditions for insertion of the selected expression vector into the cell, are within the scope of the skilled artisan.

As used herein, a "vector" may be any of a number of nucleic acid molecules into which a desired sequence may be inserted by restriction and ligation for expression in a host cell. Vectors are typically composed of DNA although RNA vectors are also available. Vectors include, but are not limited to, plasmids, phagemids and virus genomes. An expression vector is one into which a desired DNA sequence may be inserted by restriction and ligation such that it is operably joined to regulatory sequences and may be expressed as an RNA transcript.

The compositions may be delivered to a subject, a tissue, or a cell in a carrier or a pharmaceutically acceptable carrier. A subject may be a human subject or a non-human subject.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The compounds may be sterile or non-sterile.

The compounds described herein may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. In general, a pharmaceutical composition comprises the compound of the invention and a pharmaceutically acceptable carrier. Pharmaceutically acceptable carriers for nucleic acids, small molecules, peptides, monoclonal antibodies, and antibody fragments are well-known to those of ordinary skill in the art. As used herein, a pharmaceutically acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants, including those designed for slow or controlled release.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

The invention also includes kits made up of the various reagents described herein assembled to accomplish the methods of the invention. A kit for instance may include one or more pore forming protein s, optionally linked to a target binding peptide and a pore specific binding peptide. The kit may further comprise assay diluents, standards, controls and/or detectable labels. The assay diluents, standards and/ or controls may be optimized for a particular sample matrix. Reagents include, for instance, antibodies, nucleic acids, labeled secondary agents, or in the alternative, if the primary reagent is labeled, enzymatic or agent binding reagents which are capable of reacting with the labeled reagent. One skilled in the art will readily recognize that reagents of the present invention can be readily incorporated into one of the established kit formats which are well known in the art.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment or characterization of a cancer.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflect approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published

EXAMPLES

A number of the methods of the invention were tested experimentally and the data is presented in the following Examples. A brief summary is provided first. A diverse set of cargo was investigated, which included peptides containing non-natural amino acids, mirror image biomolecules, and protein scaffolds engineered to behave like antibody mimics. This platform was applied to cancer cells, where p53/MDM2 was targeted with a mirror peptide, and in a separate case targeted with tandem monobody, where it disrupted the oncoprotein Bcr-Abl. All variants were delivered to the cell cytosol, providing an important tool to investigate processes in the intracellular milieu as well as diagnostic and therapeutic utilities.

Herein described, a non-toxic form of anthrax lethal toxin was repurposed for biomolecule delivery to the cytosol of cells. The developed delivery platform consists of two non-toxic proteins from anthrax lethal toxin: protective antigen (PA, 83 kDa) and the N-terminal domain of lethal factor ($LF_N$, ~30 kDa) where the C-terminal catalytic domain responsible for cell death has been removed. Cargos with an oligo-glycine N-terminus were covalently attached to LPSTGG (SEQ ID NO: 15) at the C-terminus of $LF_N$ with the transpeptidase sortase A (SrtA) to produce the sortagged variant (STv) $LF_N$-cargo. Delivery occurs when PA binds to host cell receptors and is cleaved by a furin-family protease to form $PA_{63}$. $PA_{63}$ self-assembles to ring-shaped heptameric and octameric oligomer and forms complexes with $LF_N$-cargo ($K_d$=1 nM) that are then endocytosed. Acidification of the endosome triggers a conformational rearrangement of the PA oligomer to a translocase that unfolds and passes the $LF_N$-cargo to the cytosol.

To achieve the attachment of non-natural chemical entities to the C-terminus of $LF_N$, the calcium dependent enzyme Sortase A (SrtA) from *Staphylococcus aureus* was utilized.[20] SrtA recognizes a short peptide motif, LPXTG (SEQ ID NO: 12), and cleaves the threonine-glycine bond. The thioacyl-linked enzyme-substrate intermediate can then react with the N-terminal oligoglycine motif, resulting in formation of a covalent bond at the site of cleavage.[21] Because the oligoglycine motif tolerates promiscuous decorations, SrtA has been utilized extensively to attach various molecules to a protein of interest.[22-26] A recent study reported an evolved SrtA (SrtA*) that has much higher catalytic activity compared to that of wild-type SrtA.[27]

Figure 7:
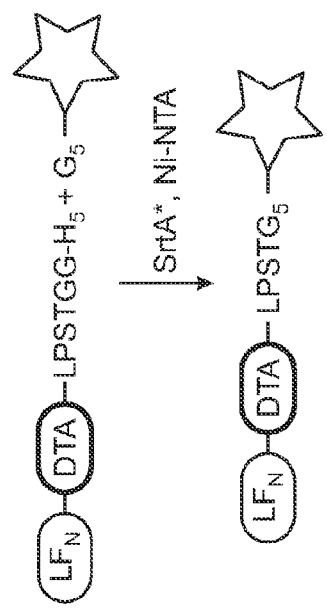
FIG. 7 shows SrtA* mediated ligation of non-natural chemical entities to $LF_N$-DTA.
Figure 6:
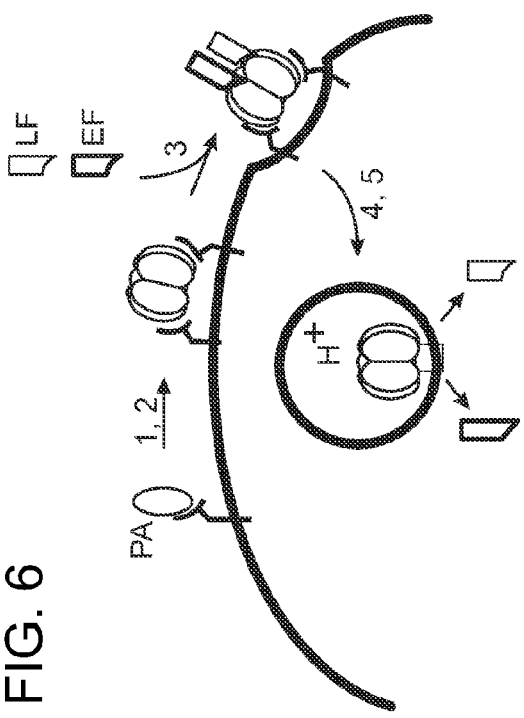
FIG. 6 shows a model of anthrax toxin entry into cells.

In the present study, SrtA* was used for the facile attachment of an array of non-natural chemical entities to $LF_N$-DTA, where DTA serves as a reporter of translocation with its ability to block protein synthesis when introduced into the cytosol (FIG. 7). FIG. 7 shows SrtA* mediated ligation of non-natural chemical entities to $LF_N$-DTA. The resulting SrtA* tagged variants (STv's) include $LF_N$-DTA conjugates of peptides modified with various non-natural amino acids, cyclic peptides, small single-domain proteins, as well as their mirror image forms. The translocation properties of these STv's were investigated, and it was found that the $PA_{63}$ pore is efficient in delivering most of the non-natural chemical entities with a few exceptions. This study provides insights into the promiscuity of the $PA_{63}$ pore, and more importantly, reveals the potential to hijack the anthrax toxin transporter for delivery of novel chemical entities into cytosol. Coupled with recent advances in PA targeting to tumor cells, our system offers an ideal platform to deliver a wide variety of biologically active chemical entities to chosen classes of cells.

The data discussed herein demonstrate that a variety of non-natural amino acid containing peptides and proteins can be delivered into cells through the anthrax toxin delivery platform. A robust and reliable method to conjugate the non-natural chemical entities to $LF_N$ is the key to explore the delivery capacity of $PA_{63}$ pore. Here SrtA mediated ligation was used and a simple one-pot method for facile preparation of STv's was developed. The sortagging reactions are conducted in aqueous buffer solution, where the proteins maintain their native structure with no further refolding required after ligation. The incorporation of a small epitope LPXTG (SEQ ID NO: 15) at C-terminal of $LF_N$-DTA has little perturbation to the protein function, as indicated by DTA activity. Although relatively high concentrations of oligoglycine peptides (≥300 μM) and oligoglycine proteins (≥100 μM) are necessary to maximize ligation efficiency and minimize LPXTG (SEQ ID NO: 15) tag hydrolysis, these peptides and proteins are easily prepared and soluble at these concentrations.

Among the STv's that were tested, all the linear peptides, regardless of the non-amino acids installed, the small affibody and GB1 protein, as well as their mirror image forms, were translocated through $PA_{63}$ pore as efficiently as $LF_N$-DTA. These results indicate that the $PA_{63}$ pore is relatively promiscuous in terms of the substrates to be translocated. Once the unfolding and translocation is initiated by $LF_N$ through interaction with a clamp and φ-clamp under acidic pH and a positive membrane potential, these two clamps are able to grip and actively unfold the trailing part, with high tolerance in chemical modification and stereochemistry.

However, the STv's with cyclic peptides and 10FN3 attached were one to two log units shifted in terms of EC50 compared to $LF_N$-DTA. The ~15 Å wide lumen of the putative 14-strand β-barrel formed by $PA_{63}$ limits the sizes of chemical structures to be translocated.[40] The cyclic peptides that were prepared contained 10 amino acids in the ring, including a proline that could restrict a more extended form of the peptides. For 10FN3, the high stability of the β-sheet scaffold contributes to a high unfolding barrier through the pore. In a force-dependent unfolding mechanism, β-sheet regions often represent the rate-limiting mechanical breakpoint, as shown in the β-sheet subdomain of $LF_N$.[41] Interestingly, STv14mut, which contains the same protein scaffold as 10FN3 but mutations in the loops, can be translocated as efficiently as $LF_N$-DTA. Although the structure and stability of the 10FN3 mutant has not yet been determined, the possible change in orientation and topology of β-sheet structure can be key determinants of lowering the unfolding forces.[42]

The immunoblotting results are consistent with the cytotoxicity results, where less amount of STv14 was translocated to the cytoplasm compared to other STvs. Due to the detection limit of the immunoblotting, STv8 and STv9, which had even higher EC50 compared to STv14, had the amount of translocation that could not be detected. On the other hand, STv's with both L- and D-form of affibody and GB1 showed higher amount of translocation than $LF_N$-DTA and the peptide conjugates. Structurally, the affibody contains all α helix and GB1 is partially α helix. It was suggested helical structure would provide significant kinetic benefit to the translocation by reducing conformational entropy relative to unstructured peptide, and also present a handle for the α clamp to grip the substrate.[11] The kinetic advantage of α helix during translocation could be attenuated during the extended treatment (overnight) of cells with STv's for immunoblotting samples.

The affibody and monobody have served as a robust scaffold for engineering to mimic antibodies engineered to bind to a large number of target proteins or peptides with high affinity. The efficient translocation of these two scaffolds into the cell through $PA_{63}$ pore provides a promising way of delivering functional antibody mimics to target intracellular proteins. More importantly, the delivery of their mirror image forms would address the stability and immunogenicity problems of these proteins.

A remaining question concerns the proper folding of these proteins after reaching the cytosol. The cytotoxicity assay indicates that the DTA fused to $LF_N$ is properly folded and functional, which implies that the L-proteins would be properly folded in the cytosol. The assays may be used to detect the functions of proteins translocated to the cell to confirm their refolding status.

With the ability to deliver a variety of non-natural and functional peptides and proteins to the cell, targeting PA to specific cells line would make this delivery platform more attractive in therapeutic applications. Targeting of PA to cells enriched in urokinase or matrix metalloprotease has been achieved by changing the proteolytic activation site.[44,45] More recently, PA was redirected to EGFR receptor by mutating its native receptor-binding function and fusing to EGF. With the advances in PA targeting, this delivery system offers more adaptability and modularity for specific applications.

The delivery platform based on PA and $LF_N$ provides a powerful tool to transport a wide array of biomolecules to the cytosol. The key players-PA, $LF_N$, and SrtA- are functional and easily expressed in E. coli to yield ~100 mgs of material. Nanomolar concentrations of PA and $LF_N$-cargo were added to cells and after a period of time nanomolar concentrations of cargo reached the cytosol. A number of controls and assays can be used in a facile manner to confirm transport into the cell. Endosomal escape was primarily dependent on $LF_N$ interacting with the PA oligomer to initiate translocation and efficiency was only altered with cyclic peptides or a thermally stable protein. For the first time, this platform enabled the delivery of mirror image proteins into the cell and the modularity of the platform allowed for the use of biotin or click reactions to confirm presence in the cytosol. Mirror image peptides and proteins appear to have altered immunogenicity and are stable to proteolysis. This allows for questions regarding their biological properties in the cytosol to be addressed. The host cell receptors that mediate assembly and entry of the delivery system into cells are found on most cell types—copy number ranges from 10,000 to 40,000. Because delivery is mediated by host cell receptors, the platform can be tuned to target specific cell-types as was shown by targeting PA to the EGF and HER2 receptors.

To further support of the utility of the platform, processes in the cytosol of cancer cells were perturbed. A potent D-peptide was delivered to the cytosol which disrupted the p53/MDM2 protein-protein interaction and in a separate case perturbed the function of the Bcr-Abl oncoprotein with an antibody mimic fusion.

The following experiments were performed in accordance with the invention. The present invention is further illustrated by these experiments, which in no way should be construed as further limiting.

Example 1

Preparation of Non-Natural Peptides and Proteins

Figure 8:
FIG. 8 shows peptide analogues used to prepare STv1-9.
Figure 8:
Figure 8:
Figure 8:
Figure 8:
Figure 8:
Figure 8:
Figure 8:
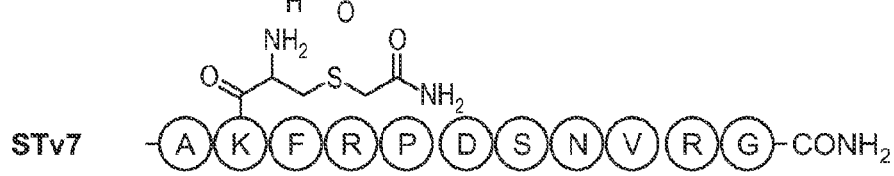
Figure 8:
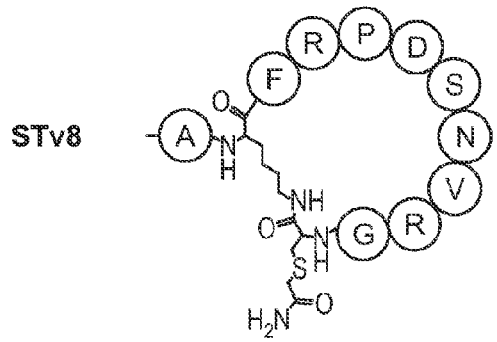
Figure 8:
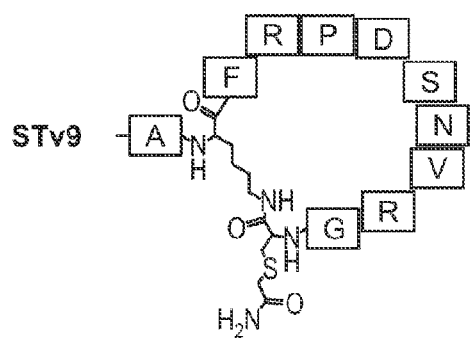

First, linear peptides were prepared by Boc (tert-butyloxycarbonyl) in situ neutralization solid-phase peptide synthesis with non-natural amino acids, including D-amino acids, β-Alanine, N-methyl-Alanine, propargyl-glycine and fluorinated phenylalanine (FIG. 8). FIG. 8 shows peptide analogues used to prepare STv1-9. L- and D- cyclic peptide analogues were also prepared, this was done by way of SPPS and intra-molecular native chemical ligation (NCL). These non-natural moieties have been shown to improve a peptide's stability against proteolytic degradation, and often time increase its biological activity or provide new sites for chemical modifications.

Figure 9:
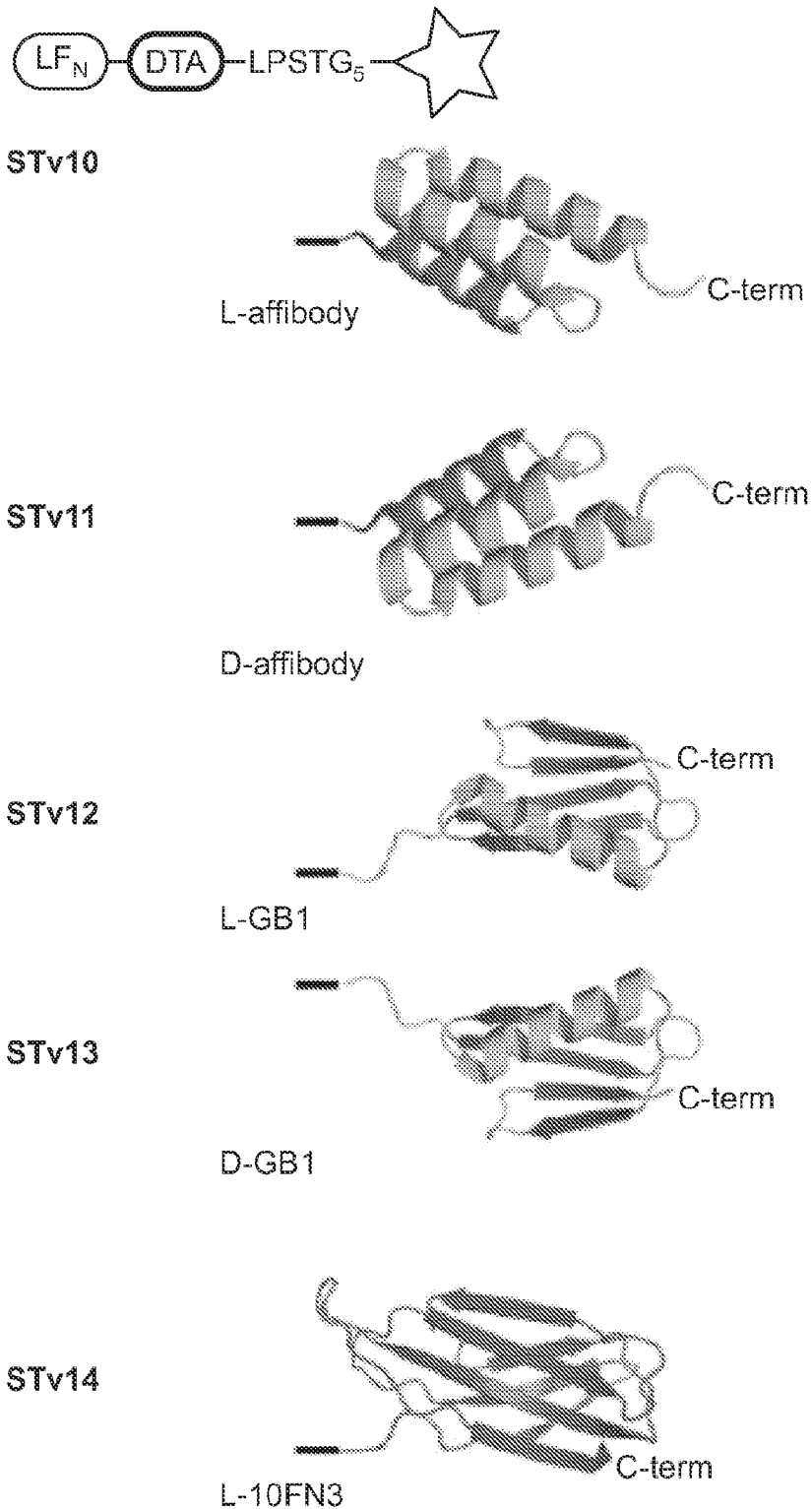
FIG. 9 shows protein analogues used to prepare STv10-14.
Figure 10A:
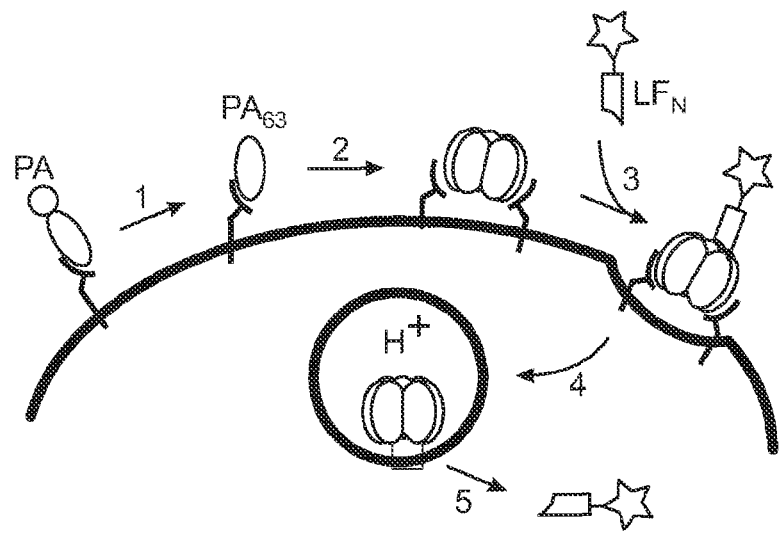
FIG. 10 sh cesses. The fusion morpholino was incubated with CHO-K1 cells for 90 minutes (14A) or 4 hours (14B) and the translocation is measured using $^3$H-Leu incorporation.
Figure 10B:
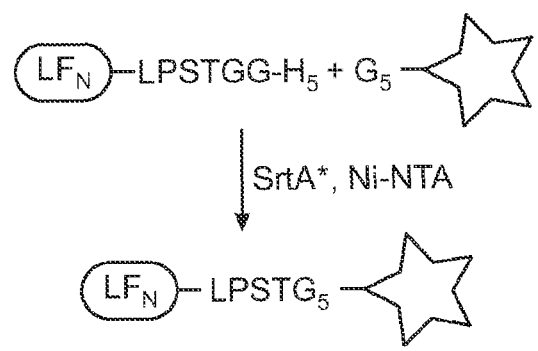
Figure 11A:
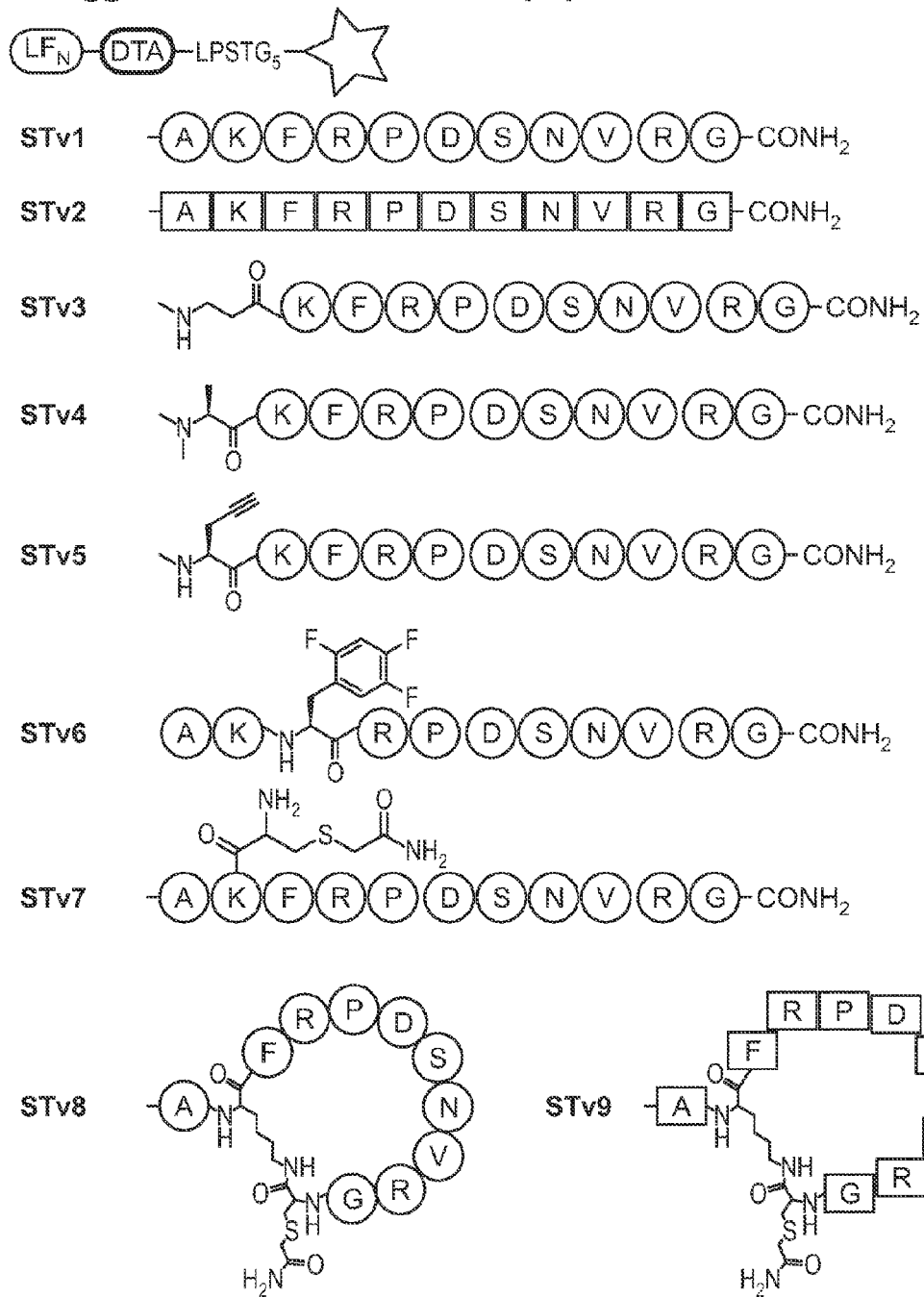
Figure 11B:
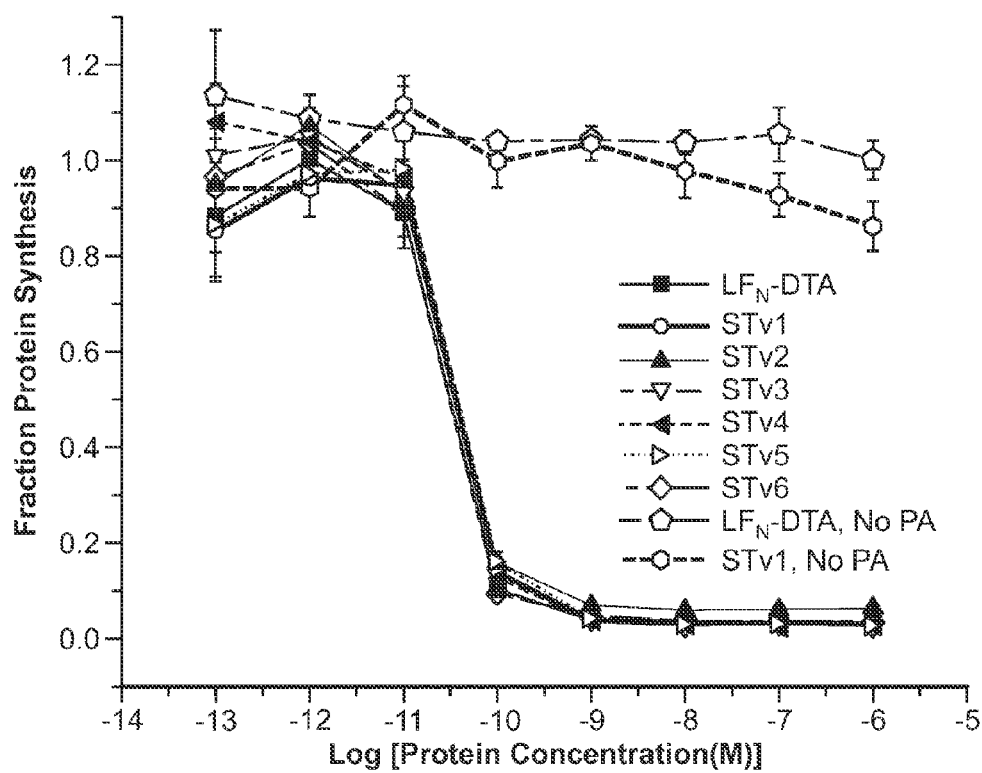
Figure 11C:
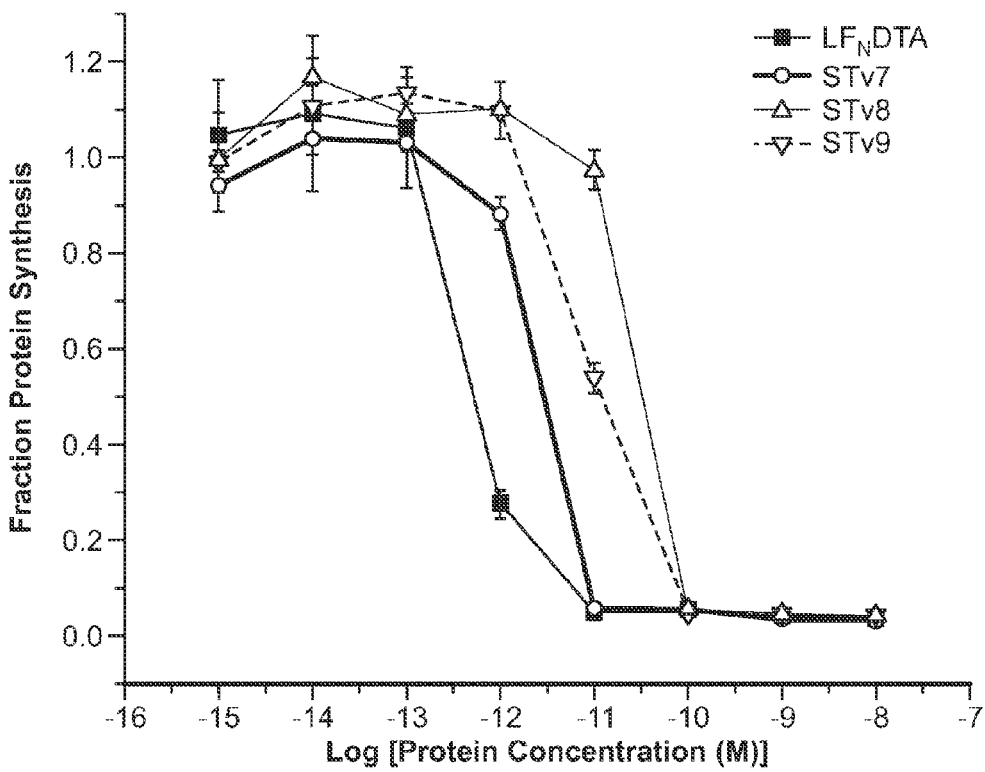

Three model proteins were chosen for working with: affibody, protein G B1 and monobody (FIG. 9). FIG. 9 shows protein analogues used to prepare STv10-14. The small, three-helix bundle domain affibody is based on the immunoglobulin G binding domain (Z domain) of protein A, and has been engineered to bind to a large number of target proteins or peptides with high affinity.[28-32] Protein G B1 domain (GB1) has well-defined secondary structural elements and has been thoroughly characterized.[33] The monomeric β-sandwich monobody is based on the tenth human fibronectin type III domain (10FN3) and has also served as a robust scaffold for engineering to mimic antibodies.[34-38] These cysteine-free proteins are small and amenable to total chemical synthesis. These proteins were prepared in L- and D-forms either recombinantly (L-AB and 10FN3) or chemically (D-AB, L-GB1, and D-GB1) using a three-segment approach, where D-affibody contained two pseudohomoglutamine from NCL sites. Mirror image proteins are of interest for potential therapeutic application because of their low immunogenicity and high proteolytic resistance in vivo.[39]

Example 2

Sortagging of Peptides/Proteins to $LF_N$-DTA

The non-natural peptides were attached to $LF_N$-DTA in a one-pot method using SrtA* (FIG. 8). $LF_N$-DTA-LPSTGG (SEQ ID NO: 16) was expressed as SUMO-protein fusions for higher expression yields and generation of the native N-terminus after removal of SUMO. The N-terminal SUMO tag was first removed by SUMO protease and subsequently incubated $LF_N$-DTA-LPSTGG (SEQ ID NO: 16) with SrtA*, Ni-NTA agarose beads, and oligoglycine peptides for 30 minutes at room temperature. By simple concentration of the supernatant of the reaction mixture, we isolated the STv products in high purity, as characterized by high resolution LCMS (FIG. 1). Sortagging of the proteins to $LF_N$-DTA followed the same method except for an extra step of gel-filtration to separate excess oligoglycine protein reactants to yield STv10-14 (FIG. 9). The highly pure $LF_N$-DTA-protein conjugates were also characterized by high resolution LC-MS (FIG. 2).

Example 3

Characterizing the Translocation Properties of STv1-14

Characterizing the translocation properties of STv1-14 into cytosol was achieved by measuring the protein synthesis inhibition in CHO-K1 cells. CHO-K1 cells were treated with STv's in the presence of PA, and then chased with Leucine-free medium supplemented with $^3$H-Leu. The amount of STv's delivered to the cytosol was indicated by the decrease of $^3$H-Leu incorporation.

The STv1-14 structures had the following sequences:

```
                                (STv1, SEQ ID NO: 17)
        G5AKFRPDSNVRG (all L)

(STv2, SEQ ID NO: 18)
        G5AKFRPDSNVRG (all D)
```

-continued

G₅(β-Ala)KFRPDSNVRG (STv3, SEQ ID NO: 19)

G₅(N-Me-Ala)KFRPDSNVRG (STv4, SEQ ID NO: 20)

G₅(proparl-Gly)KFRPDSNVRG (STv5, SEQ ID NO: 21)

G₅AK(Tri-Fluoro-F)RPDSNVRG (STv6, SEQ ID NO: 22)

G₅AK(Cys)FRPDSNVRG (all L) (STv7, SEQ ID NO: 23)

G₅AK(Cys)FRPDSNVRG(COSR) (all L) (STv8, SEQ ID NO: 24)

G₅AK(Cys)FRPDSNVRG(COSR) (all D) (STv9, SEQ ID NO: 25)

G₅-affibody (all-L) (STv10, SEQ ID NO: 26)

G₅-affibody (all-D) (STv11, SEQ ID NO: 27)

G₅-GB1 (all-L) (STv12, SEQ ID NO: 28)

G₅-GB1 (all-D) (STv13, SEQ ID NO: 29)

G₅-FN3 (STv14, SEQ ID NO: 30)

For the linear peptides with the non-natural chemical entities we included (STv2-6), the $PA_{63}$ pore was able to translocate all of them as efficiently as $LF_N$-DTA control (FIG. 3A). However, the cyclic peptides showed more than 10 times higher EC50 in protein synthesis inhibition compared to the $LF_N$-DTA control (FIG. 3B).

For protein affibody and GB1, the $PA_{63}$ pore translocated both as efficiently as $LF_N$-DTA. More interestingly, their mirror image forms were also efficiently translocated through $PA_{63}$ pore (FIG. 4A), indicating that once the translocation is initiated by $LF_N$, the $PA_{63}$ pore is capable of readily unfolding and translocating the protein regardless of the stereochemistry. In contrast, STv14 showed 10 times higher EC50 in protein synthesis inhibition compared $LF_N$-DTA (FIG. 4B), indicating the unfolding barrier imposed by the very stable structure of 10FN3.

Figure 5:
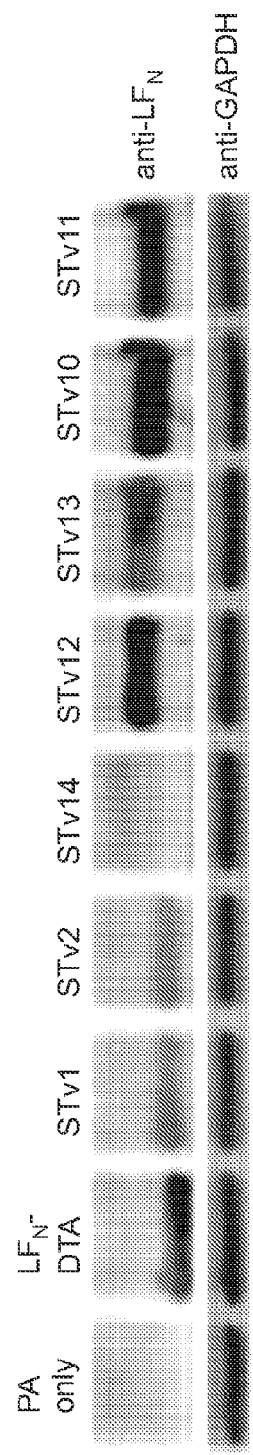
FIG. 5 shows immunoblotting analysis of cell lysates prepared from STv-treated CHO-K1 cells.

The translocation of STv's into the cytoplasm was further characterized by immunoblotting cell lysates prepared from STv-treated CHO-K1 cells. The surface bound STv's were digested by trypsin and washed away, leaving only intracellular STv's to be detected. Immunoblotting result confirmed the translocation of STv's into the cytoplasm and also showed different levels of proteins translocated to the cell, depending on the peptide or protein attached (FIG. 5). STv14 showed a much lower amount of translocation compared to other variants. The amount of STv8 and STv9 translocated into the cell were probably under the detection limit and were not detected (data not shown).

Example 4

Investigating the Translocation of Cargos Containing Modifications

Model studies were undertaken to investigate the translocation of cargos containing non-natural modifications including D-amino acids, β-alanine, N-methyl-alanine, propargyl-glycine, fluorinated phenylalanine, and cyclic analogues. Sortagged variant 1 (STv1) served as the model compound and changes were made to the peptide attached to the C-terminus of $LF_N$-DTA; DTA (A-chain of diphtheria toxin) served as the cytosolic reporter as it catalyzes the ADP-ribosylation of EF-2 and inhibits protein synthesis. The 30-minute sortagging reactions in the presence of Ni-NTA did not require extensive purification and gave isolated product yields over 50% To investigate delivery, each STv was added to CHO-K1 cells in the presence of 10 nM PA for 30 minutes and the cells were then treated medium supplemented with $^3$H-Leu. By measure of protein synthesis, we determine if the STv's were delivered to the cytosol and compare the efficiency to that of unmodified $LF_N$-DTA and STv1. All linear variants translocated as well as the positive controls $LF_N$-DTA and STv1, indicating non-natural functionalities can be appended to the C-terminus without major disruption to the platform. The cyclic probably due to the ~12 Å lumen diameter of PA due to the ~X Å lumen diameter of PA.

Example 5

Delivery of the Antibody Mimics (Affibody), Protein G B1 and Monobody

Next, the delivery of the antibody mimics (affibody), protein G B1, and monobody was investigated. All three variants are widely used in protein engineering and biotechnology to generate highly specific, potent, and cysteine-free antibody mimics. Highly pure STv's were obtained and their delivery into CHO-K1 cells was measured using the protein synthesis inhibition assay. STv10 and STv12 entered cells at levels comparable to the positive control $LF_N$-DTA, however, STv14 was 10 times less efficient. To investigate whether the high thermal stability of 10FN3 in STv14 (unfolding temperature 88° C.) may have affected the translocation efficiency, an STv14 mutant with a reduced thermal stability was tested. The results showed that this restored translocation to $LF_N$-DTA levels, indicating that high thermal stability of 10FN3 had affected the translocation efficiency.

Example 6

Mirror Image Variants Translocate Through PA

To investigate the transport of mirror image variants, mirror image forms of the affibody and protein G B1 were chemically synthesized and sortagged onto $LF_N$-DTA. It was found that the mirror variants translocated through PA, indicating that the stereochemistry of the cargo does not alter translocation. To confirm that the D-protein remains intact in the cytosol, $LF_N$-D-affibody-alkyne and $LF_N$-D-affibody-biotin were prepared and their translocation properties were studied. The alkyne and biotin groups were installed on the C-terminus of the D-affibody. CHO-K1 cells were treated with each variant in the presence of PA or the translocation mutant PA[F427H]. PA[F427H] is a negative control because complex formation and internalization with PA still occurs, but endosomal escape of the cargo is arrested; this allows for differentiation between cytosolic material and materials in the endosomal and lysosomal compartments. Western blot with anti-LF antibody indicated $LF_N$-D-affibody-alkyne and $LF_N$-D-affibody-biotin were delivered to the cytosol and mirror amounts of material were observed for the PA[F427H] condition. Translocation for LF$_N$-D-affibody-biotin was further confirmed by blotting with streptavidin conjugated to an IR680 dye. To confirm that the alkyne was still present after translocation, the lysate was collected and a Cu(I)-catalyzed azide-alkynyl click reaction was used to label the D-affibody-alkyne with Alexa Fluor® 594 (available commercially from Invitrogen™). By in-gel fluorescence a fluorophore positive band was observed at the correct molecular weight. These results indicate that mirror image proteins are delivered into the cytosol of cells and an alkyne or biotin group attached to the cargo can be used for detection.

Example 7

Determining the Amount of Cargo Delivered to the Cytosol

Figure 12A:
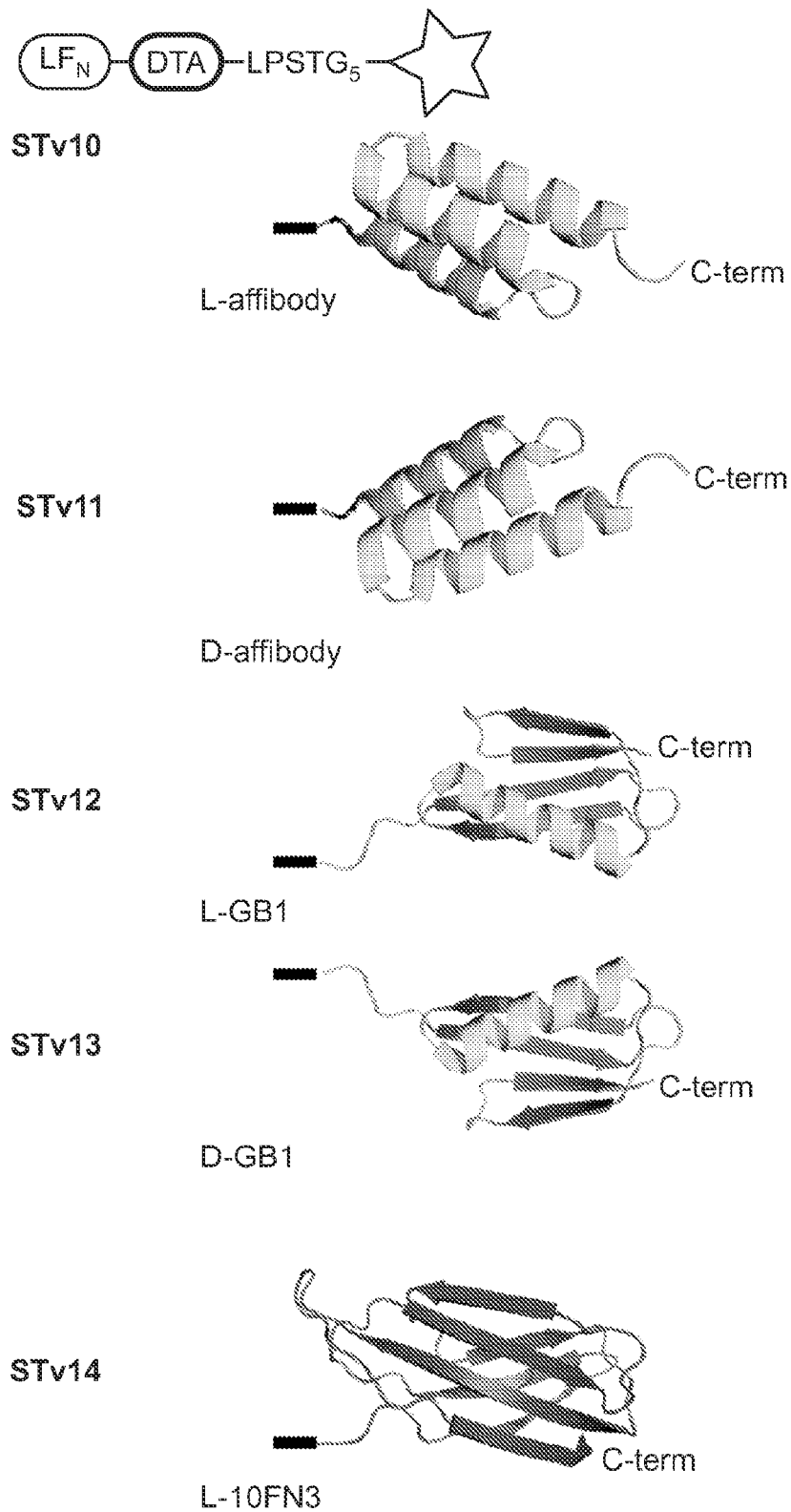
Figure 12B:
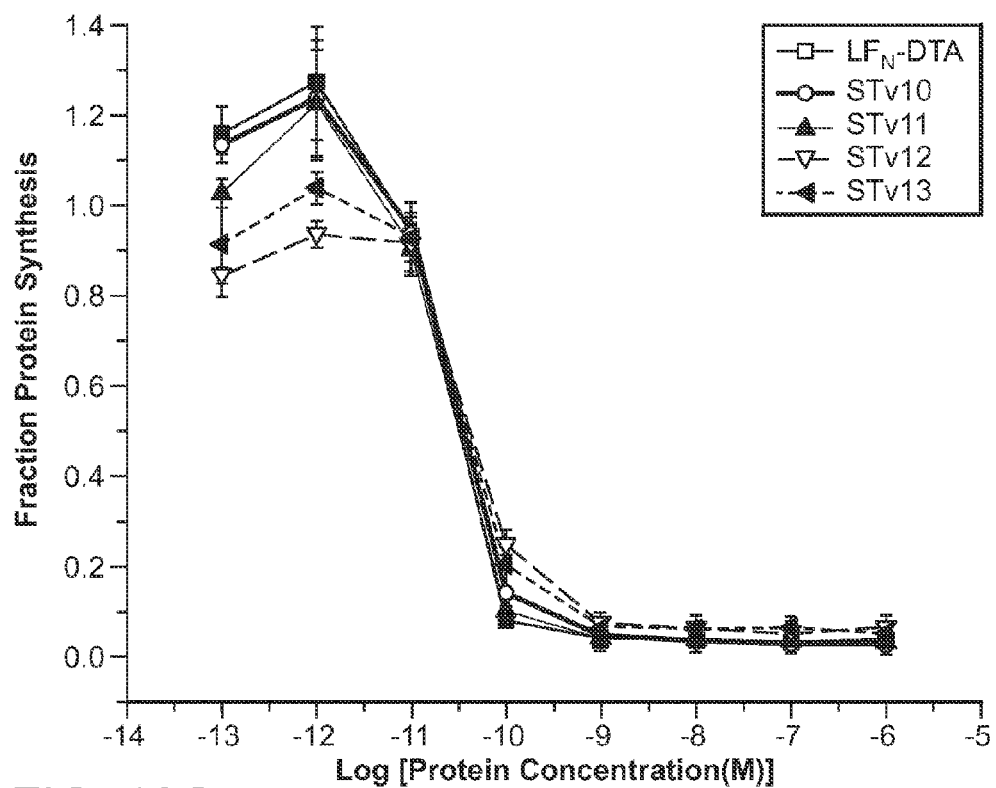
Figure 12C:
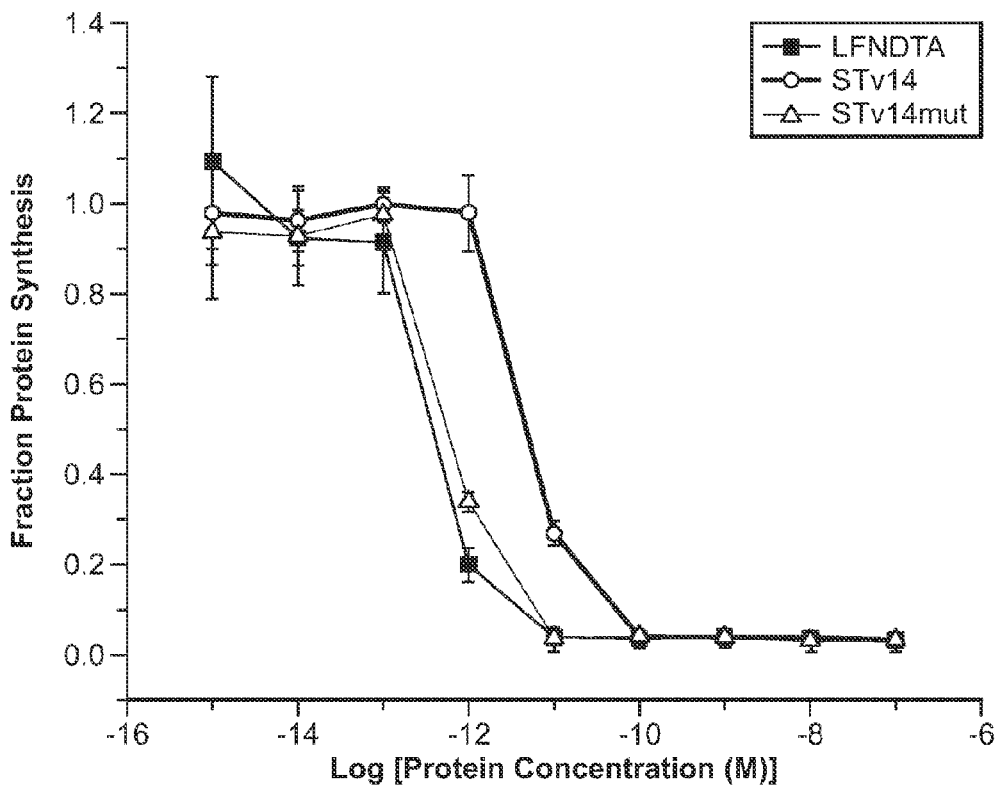

To determine the amount of cargo delivered to the cytosol, the band intensity of anti-LF from a western blot was quantified. In this assay, CHO-K1 cells were treated with each variant and PA for 24 hours. The surface bound STv's were digested with trypsin and washed, leaving the intracellular fraction. The negative control was PA[F427H], which was used to confirm that the majority of material detected was in fact the cytosolic fraction. The results in FIG. 12D confirmed the translocation of STv's into the cytoplasm and indicated varying amounts of cargo material which correlated with the delivery data obtained from protein synthesis inhibition assay. Based on this investigation, the amount delivered was on average 1 fg per cell, which corresponds to 12000 molecules per cell and 30 nM in CHO-K1 cells (1 CHO-K1 cell ~0.5 pL).

Example 8

Disrupting the p53/MDM2 Protein Protein Interaction in the Cytosol of Cancer Cells with a Delivered D-Peptide that Binds MDM2

Figure 13A:
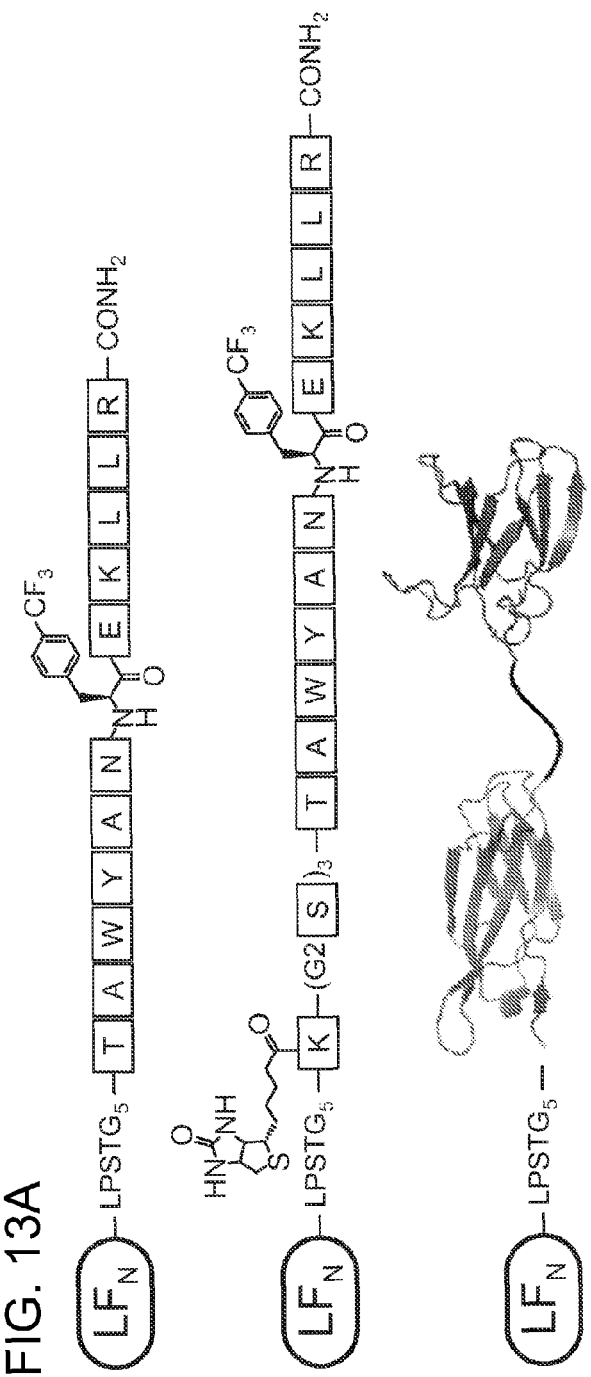
Figure 13B:
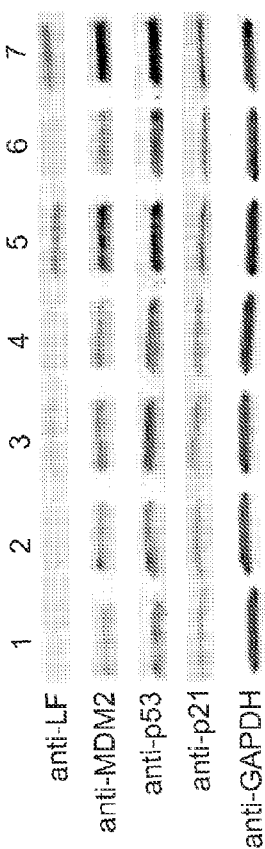
Figure 13C:
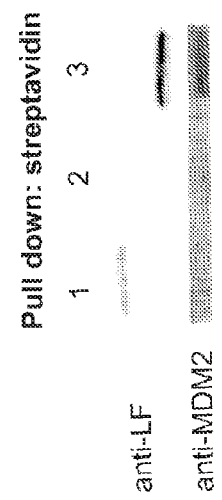
Figure 13D:
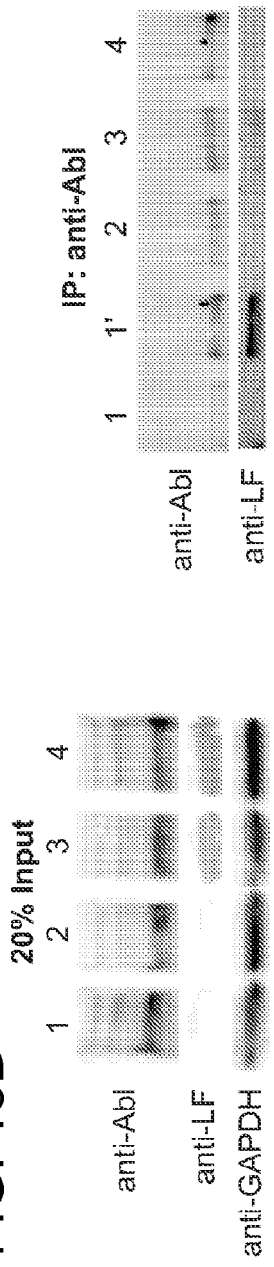
Figure 13E:
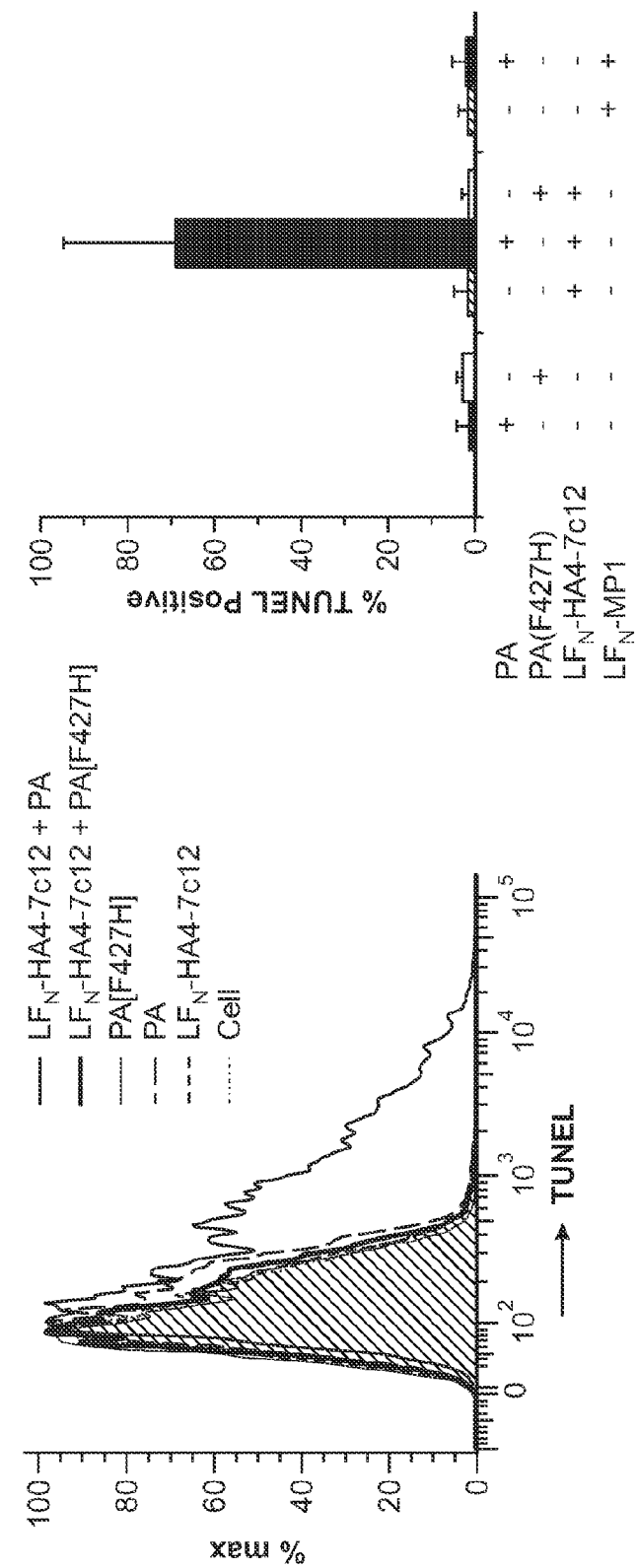
Figure 14A:
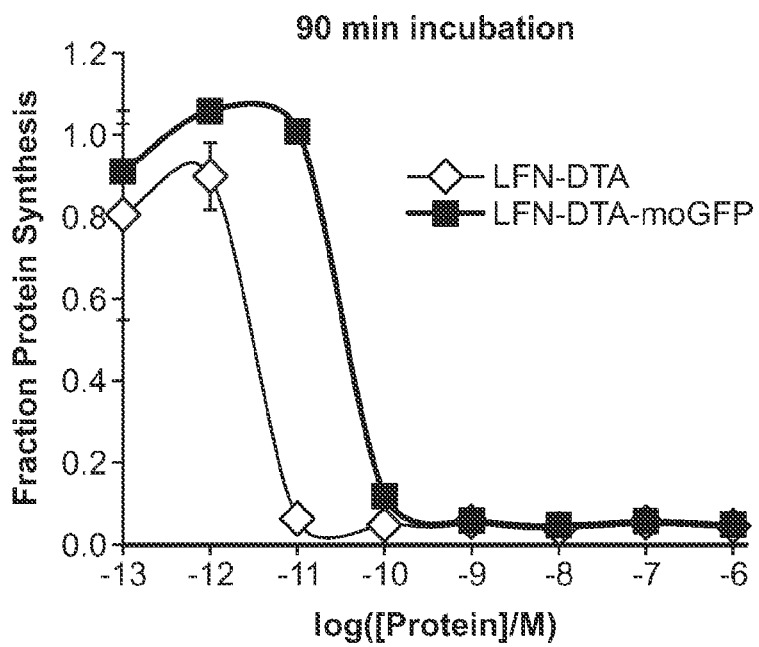
Figure 14B:
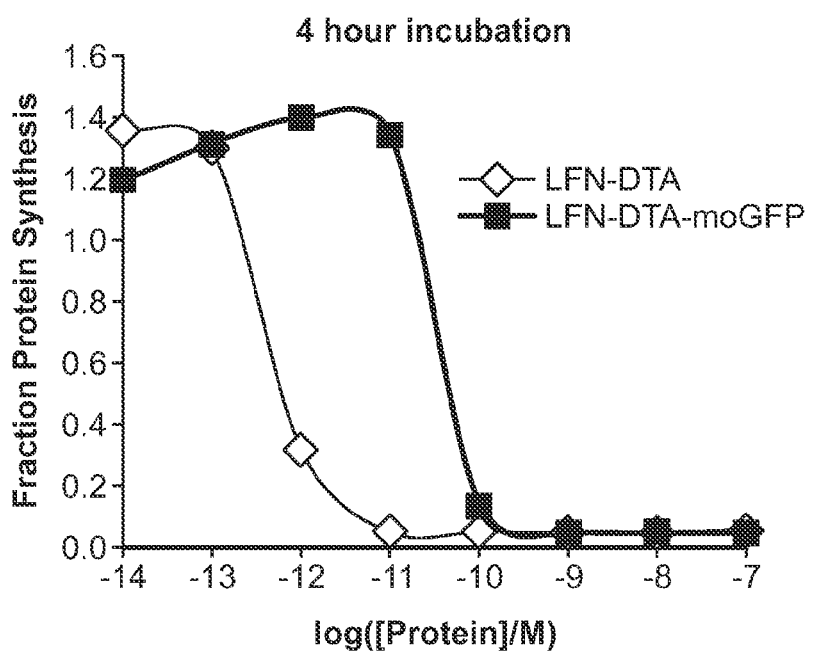

The inhibitor D-peptide ($^D$PMI) is resistant to proteolysis and has a $K_d$ of 0.45 nM towards MDM2. $^D$PMI was sortagged onto LF$_N$ and LF$_N$-DTA. Protein synthesis inhibition indicated that the LF$_N$-DTA conjugate translocated through PA in CHO-K1 and p53 containing human glioblastoma U87 cells (SI). By western blot the amount of cargo delivered to the U87 cell was 350 nM per cell, which corresponds to 450000 molecules. Streptavidin/biotin pull-down was used to confirm the binding of delivered LF$_N$-$^D$PMI to MDM-2 in the cytosol of cells by use of a biotin cargo variant. The LF$_N$-$^D$PMI-biotin was captured with streptavidin agarose beads from cell lysate and the elution was immunoblotted with anti-LF and anti-MDM2 antibody. As shown in FIG. 13B, MDM-2 was pulled down with delivered LF$_N$-$^D$PMI-biotin while no MDM2 was detected in the various control experiments including the PA[F427H] condition.

Example: 9

Investigating the Inhibitory Effects of the LF$_N$-$^D$PMI on p53/MDM2 Interaction in U87 Cells The disruption of p53/MDM2 interaction results in stabilization and accumulation of the p53 protein, and activation and expression of p53 regulated proteins such as MDM2 and p21. The protein levels of p53, MDM2 and p21 in U87 cells after delivery of LF$_N$-$^D$PMI were analyzed by immunoblotting with corresponding antibodies The following primary and secondary antibodies were used for this analysis: goat anti-LF (Santa Cruz bD-17), rabbit anti-MDM2 (Santa Cruz N-20), rabbit anti-p21 (Santa Cruz C-21), mouse anti-p53 (Santa Cruz DO-1), goat anti-mouse IRdye 680RD (Licor), goat anti-rabbit IRdye 800CW (Licor), and donkey anti-goat IRdye 680LT (Licor). Increased levels of p53, MDM2 and p21 compared to the PA[F427H] controls were observed, indicating that the delivered LF$_N$-$^D$PMI perturbed the p53 pathway. Collectively, these results indicate that a mirror image peptide can be delivered to the cytosol of cancer cells and used to disrupt a critical protein-protein interaction.

Example 10

Delivering Antibody Mimics to Perturb Cellular Processes

The tandem 10FN3 monobody that binds the Src homology 2 (SH2) domain of the oncoprotein Bcr-Abl with nanomolar affinity was investigated to determine whether antibody mimics could be delivered to perturb cellular processes. The monobodies HA4 and 7c12 were reported to modestly inhibit kinase activity and induce apoptosis when overexpressed in chronic myeloid leukemia (CML) K562 cells. LF$_N$-HA4-7c12 and LF$_N$-DTA variants were prepared and their entry into the cytosol of K562 cells was studied. The protein synthesis inhibition assay showed that PA translocated the tandem monobody efficiently into K562 cells. Western blot analysis showed that ~1.2 fg or 14000 molecules of LF$_N$-HA4-7c12 reached the cytosol, giving a concentration of ~10 nM, which is in-line with the measured $K_d$ (12 nM) of LF$_N$-HA4-7c12 toward the Abl SH2 domain. We also investigated binding mutant of HA4-7c12 toward SH2 (HA4:Y87A; 7c12:Y62E/F87K in the original sequence) and found that LF$_N$-mHA4-7c12 translocated at wild-type levels.

Example 11

Fusion Monobodies can be Translocated into Cells to Regulate Cytosolic Process

To investigate whether the delivered LF$_N$-HA4-7c12 bound to its target in the cytosol, K562 cell lysates were subjected to immunoprecipitation with anti-Abl antibody. Immunoblot analysis of the lysates with anti-LF antibody revealed a protein band corresponding to the binder for the cells treated LF$_N$-HA4-7c12 and PA, while the band was absent when PA[F427H] or LF$_N$-mHA4-7c12 were used. This result indicates that monobody fusion bound to Bcr-Abl in the cytosol of cells. To test whether binding results in apoptotic cell death, K562 cells were treated with LF$_N$-HA4-7c12 in the presence of PA. After 4 days, high amounts of apoptosis were observed, as measured by Terminal deoxynucleotidyl transferase dUTP nick end labeling (TUNEL). The cells were not affected by any of the components alone. It was found that LF$_N$-mHA4-7c12 when added alone to cells was toxic, so PA[F427H] and LF$_N$-MP1 served as negative controls. This data suggests that fusion monobodies can be translocated into cells to regulate cytosolic process.

Example 12

Fusion Morpholinos can be Translocated into Cells to Regulate Cytosolic Processes Fusion Morpholinos were created based on the following synthetic scheme:

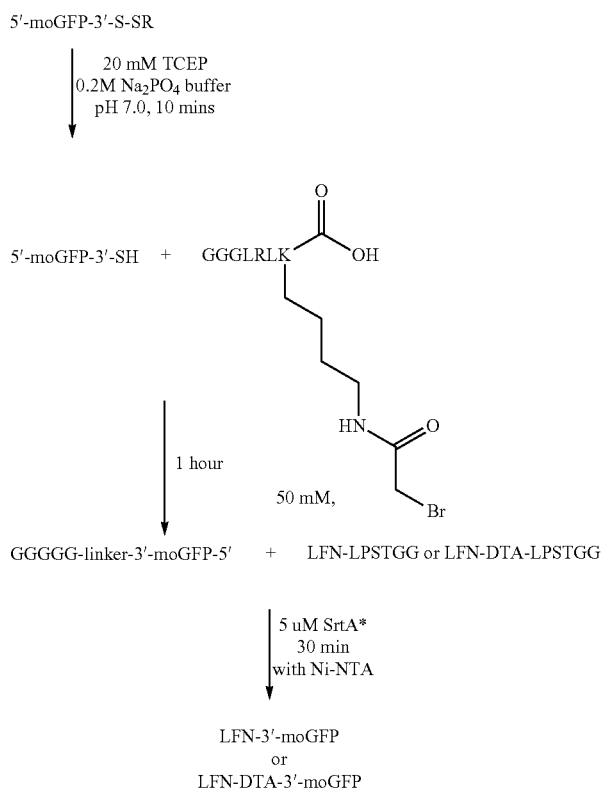

Morpholino oligonucleotides were purchased with 3' disulfide label from Genetools. The disulfide is reduced and then the morpholino is directly ligated to a bromopeptide with N-terminal Gn (n=3-5) in a one-pot reaction. The Gn-morpholino is sortagged to LFN-LPSTGG (SEQ ID NO: 31) or LFN-DTA-LPSTGG (SEQ ID NO: 32) with similar conditions as example 2. The product is isolated with a 20% yield.

The synthesized molecules were analyzed using LC-MS. The fusion morpholino was incubated with CHO-K1 cells for 90 minutes or 4 hours and the translocation is measured using $^{3}$H-Leu incorporation. The results of these assays are shown in FIGS. 14A and 14B. The $LF_N$-DTA-morpholino conjugate translocates about 100-fold less efficiently than $LF_N$-DTA.

Example 13

Synthesis of Multiple Fusion Proteins of the Invention

A

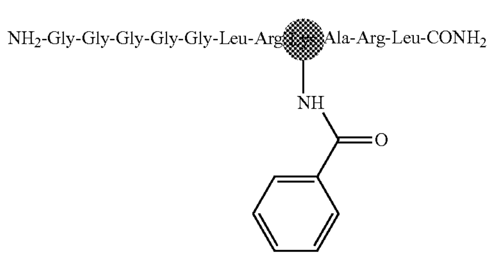

-continued

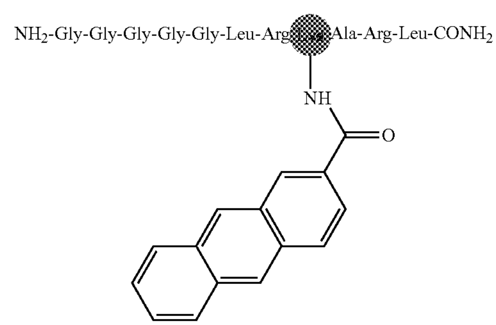

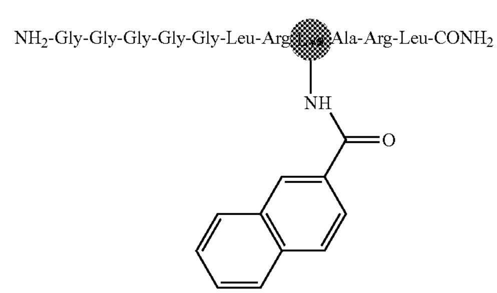

-continued

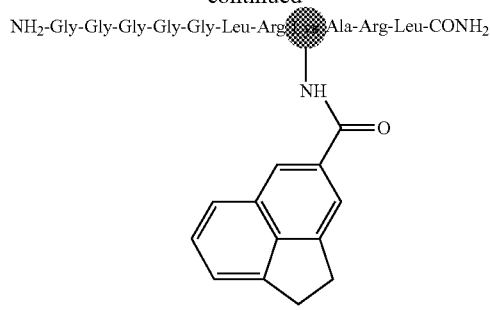

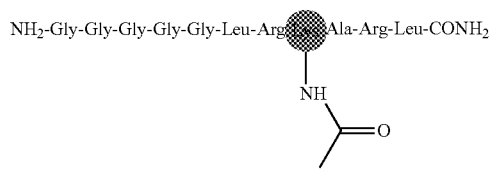

On-Resin Synthesis of Model Peptide-Small Molecule Constructs:

The parent peptide Gly-Gly-Gly-Gly-Gly-Leu-Arg-Lys-Ala-Arg-Leu (SEQ ID NO: 33) used for the model studies was synthesized under fast flow coupling/deprotection conditions with in-situ neutralization Fmoc (fluorenylmethoxycarbonyl chloride) protocol on MBHA resin. Alloc protecting group of the lysine side chain was removed by treatment of the protected resin with tetrakis triphenylphosphine palladium [0] [Pd(PPh$_3$)$_4$] in the presence of phenylsilane [PhSiH$_3$]. The free amino group of the side chain lysine was then coupled to the corresponding small molecule carboxylic acid (acetic acid, benzoic acid, naphtholic acid, anthracene-9-carboxylic acid and 5-acenaphthene carboxylic acid). The purification of the peptides was achieved using RP-HPLC C$_{18}$-bound silica column. The characterizations were performed using high resolution LC-MS.

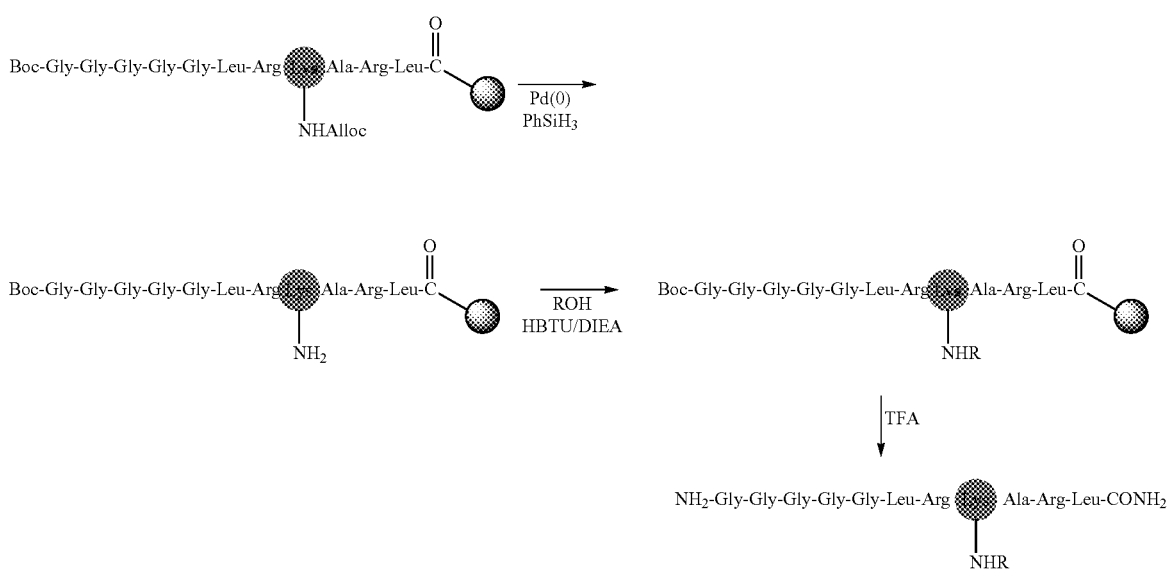

B

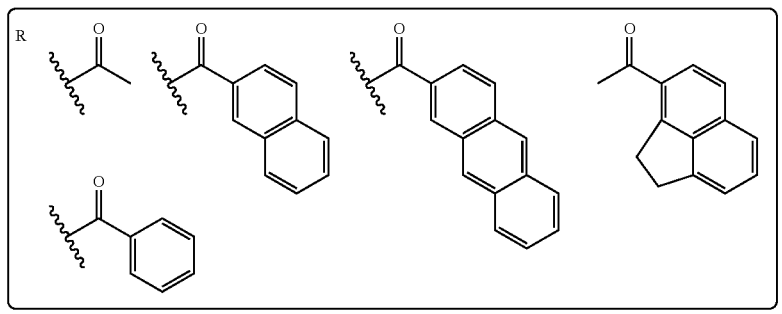

Enzymatic Ligation of Model Peptide-Small Molecules to $LF_N$-DTA:

Model peptide-small molecules (FIG. 13 A) were conjugated to $LF_N$-DTA as described previously in Example 2. Briefly, peptide-small molecule sample [500 μM], $LF_N$-DTA-LPSTGG-His (SEQ ID NO: 34) [50 μM] and SrtA* [5 μM] were mixed in sortase buffer [pH= 7.25] over nickel beads for 30 min at room temperature. Removal of the beads and concentration of the supernatant using 30K filters yielded the pure constructs as shown by LC-MS profiles (Figure D).

C

LFN — DTA — Leu-Pro-Ser-Thr-Gly-Gly

NH₂-Gly-Gly-Gly-Gly-Gly-Leu-Arg — Ala-Arg-Leu-CONH₂
                                |
                               NHR

↓ SrtA*

LFN — DTA — Leu-Pro-Ser-Thr-Gly₅-Leu-Arg — Ala-Arg-Leu-CONH₂
                                          |
                                         NHR

The purified constructs were analyzed by LC-MS.

D

LFN — DTA — Leu-Pro-Ser-Thr-Gly₅-Leu-Arg — Ala-Arg-Leu-CONH₂
                                          |
                                         NH
                                          |
                                         C=O
                                          |
                                         (phenyl)

(LFN-DTA-Benzoicacid)

Model LFN-small molecules translocated through PA pore:

LFN — DTA — Leu-Pro-Ser-Thr-Gly₅-Leu-Arg — Ala-Arg-Leu-CONH₂
                                          |
                                         NH
                                          |
                                         C=O
                                          |
                                         CH₃

(LFN-DTA-Acacid)

LFN — DTA — Leu-Pro-Ser-Thr-Gly₅-Leu-Arg — Ala-Arg-Leu-CONH₂
                                          |
                                         NH
                                          |
                                         C=O
                                          |
                                         (phenyl)

(LFN-DTA-Benzoicacid)

-continued

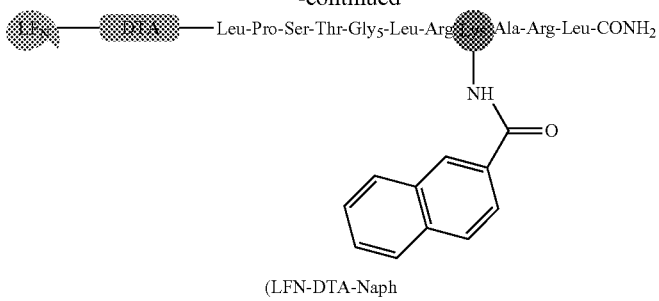

(LFN-DTA-Naph)

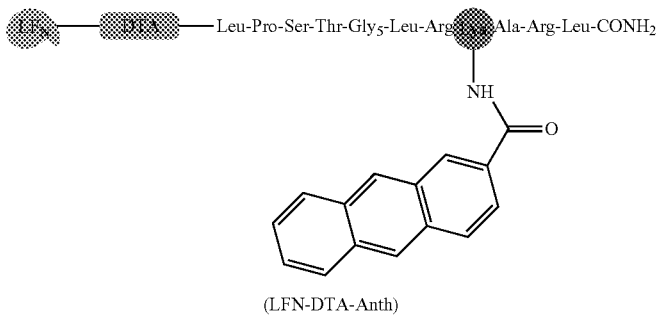

(LFN-DTA-Anth)

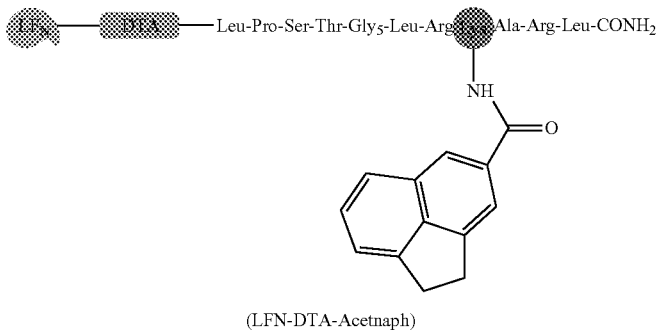

(LFN-DTA-Acetnaph)

Figure 15:
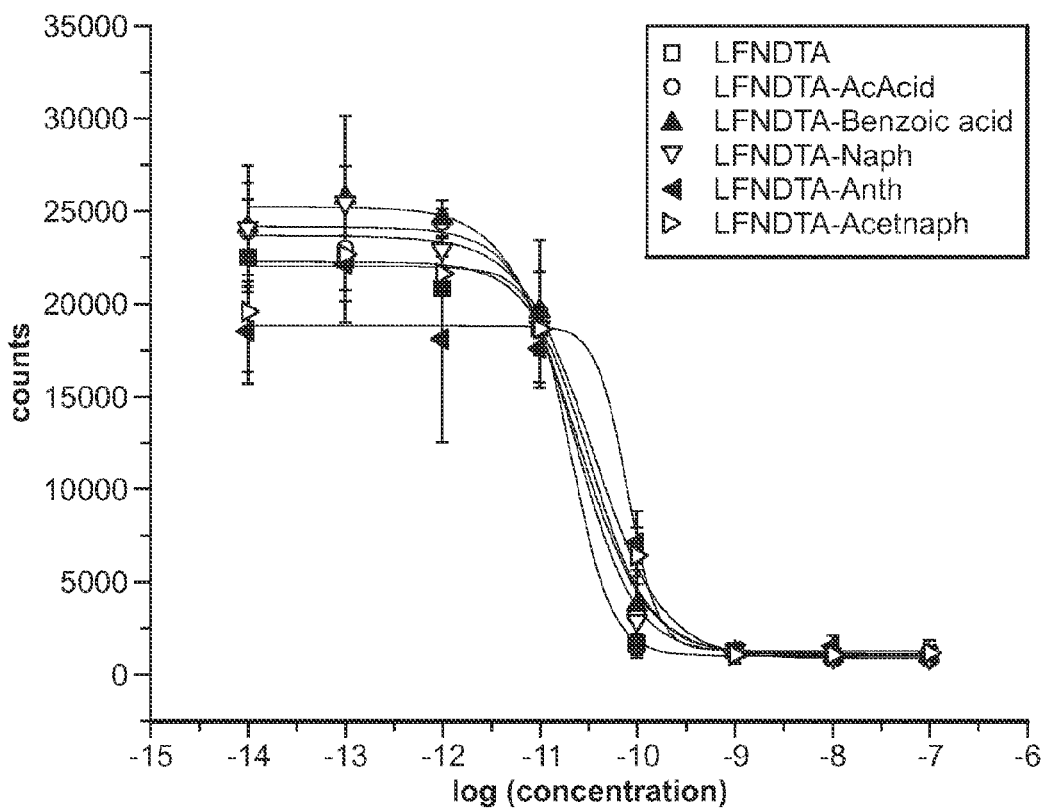
FIG. 15 is a graph depicting the results of translocation of peptide-small molecules fusion molecules through a pore and into the cytosol of a living cell.

The results of the study are shown in FIG. 15. The model peptide-small molecule constructs were successfully translocated through the pore.

Example 14

Fusion Molecules Incorporating Chemotherapeutic Drugs

Fusion molecules incorporating chemotherapeutic drugs were performed and the it was demonstrated that the chemotherapeutic drugs were delivered to the cytosol and were functionally active.

Chemoenzymatic Synthesis of LFN-DTA-Doxorubicin: Figure A:

N-succinimidyl ester of maleimidopropionic acid was obtained by reacting maleimidopropionic acid and N-hydroxy succinimide in the presence of N-N'-dicyclohexylcarboiimide (DCC) in anhydrous dichloromethane ($CH_2Cl_2$) at 0° C. under Argon atmosphere, followed by gradual warming to room temperature over 8 hours. The TLC (5:1, $CH_2Cl_2$/methanol) and LC-MS analysis of the reaction mixture confirmed consumption of the starting materials and formation of the desired product.

Doxorubicin (DOX) hydrochloride and N-succinimidyl ester of maleimidopropionic acid were taken in DMF and reacted for 1 hour in the presence of N,N-diisopropylethylamine DIEA, at which TLC analysis (5:1,CH$_2$Cl$_2$/methanol) indicated completion of the reaction and formation of a major product. The reaction mixture was quenched by diluting with DCM, followed by repetitive aqueous extractions to remove DMF and unreacted Doxorubicin. Combined organic phase was dried over magnesium sulfate (MgSO4), inorganic salts were filtered off and concentrated in vacuo to dryness. The crude product was purified by silica flash chromatography (5:1,CH$_2$Cl$_2$/methanol), giving thiol reactive DOX derivative; maleimido-DOX in 82% yield. The identity of the product was confirmed by $^1$H-NMR and high resolution LC-MS.

Chemoenzymatic Synthesis of LFN-DTA-Doxorubicin

The C-terminus cysteine containing carrier peptide; Gly-Gly-Gly-Gly-Gly-Leu-Arg-Arg-Leu-Arg-Ala-Cys (SEQ ID NO: 35) was synthesized as described above. The sulfur of the cysteine amino acid was selectively reacted with the maleimido moiety on modified DOX by stirring peptide and Maleimido-DOX in DMF for 5 hours at 36° C., followed by 10 hours at room temperature. The reaction mixture was purified by RP-HPLC to give peptide-DOX conjugate in 88% yield.

A

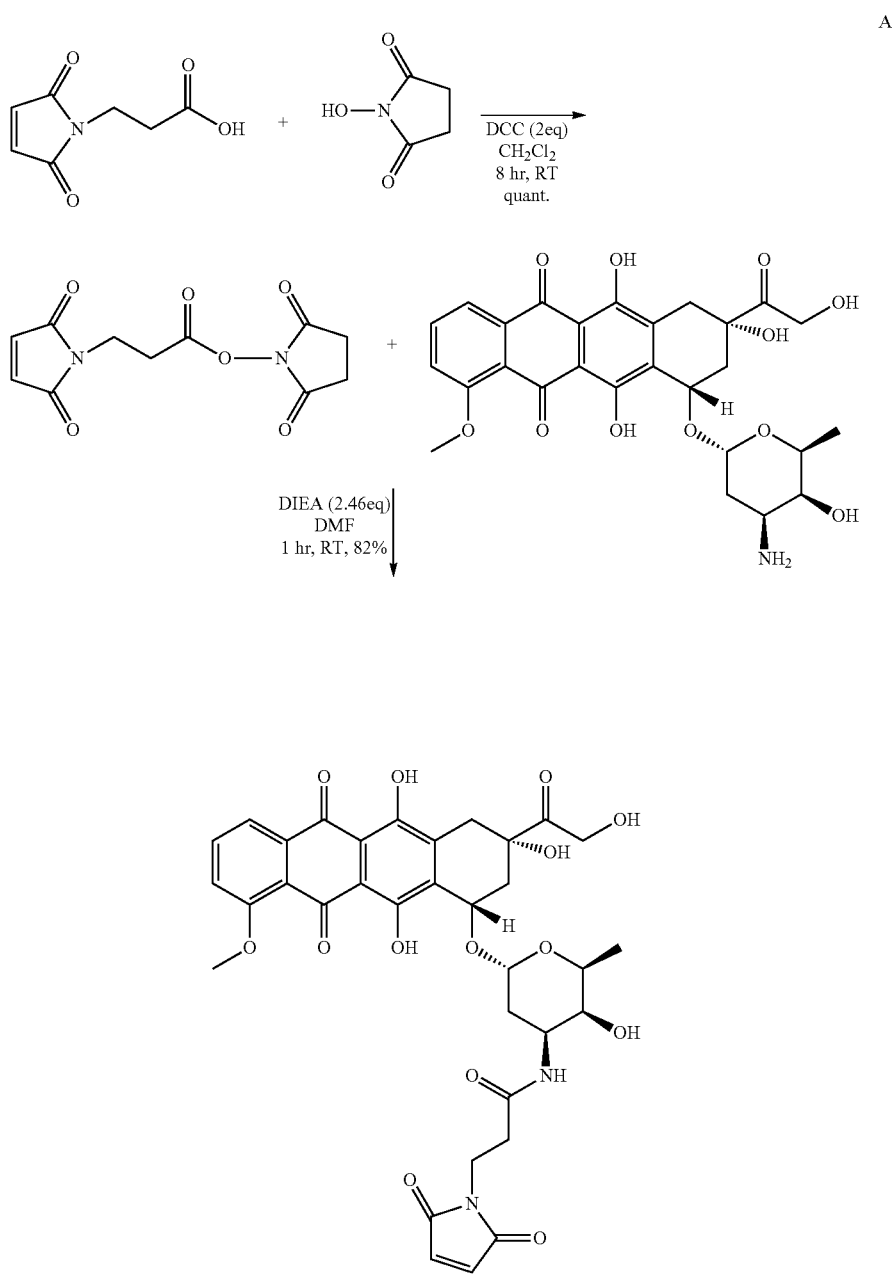

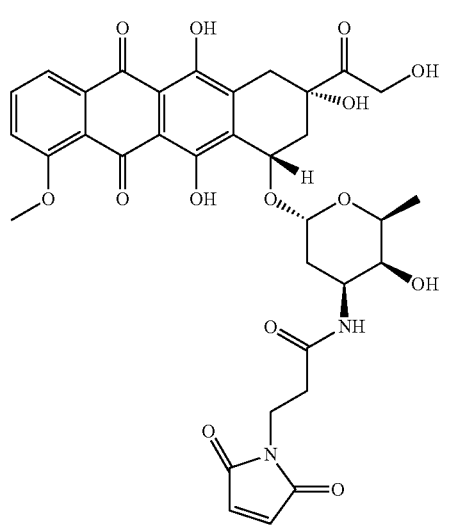
B
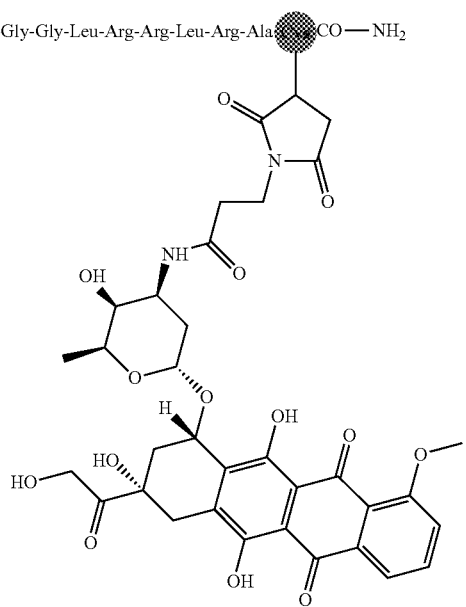
Chemoenzymatic synthesis of LFN-DTA-Doxorubicin: Enzymatic ligation of peptide-DOX to LFN-DTA: as described in Example 13, Figure C.

Description of Example 14
Chemoenzymatic Synthesis of LFN-DTA-Docetaxel
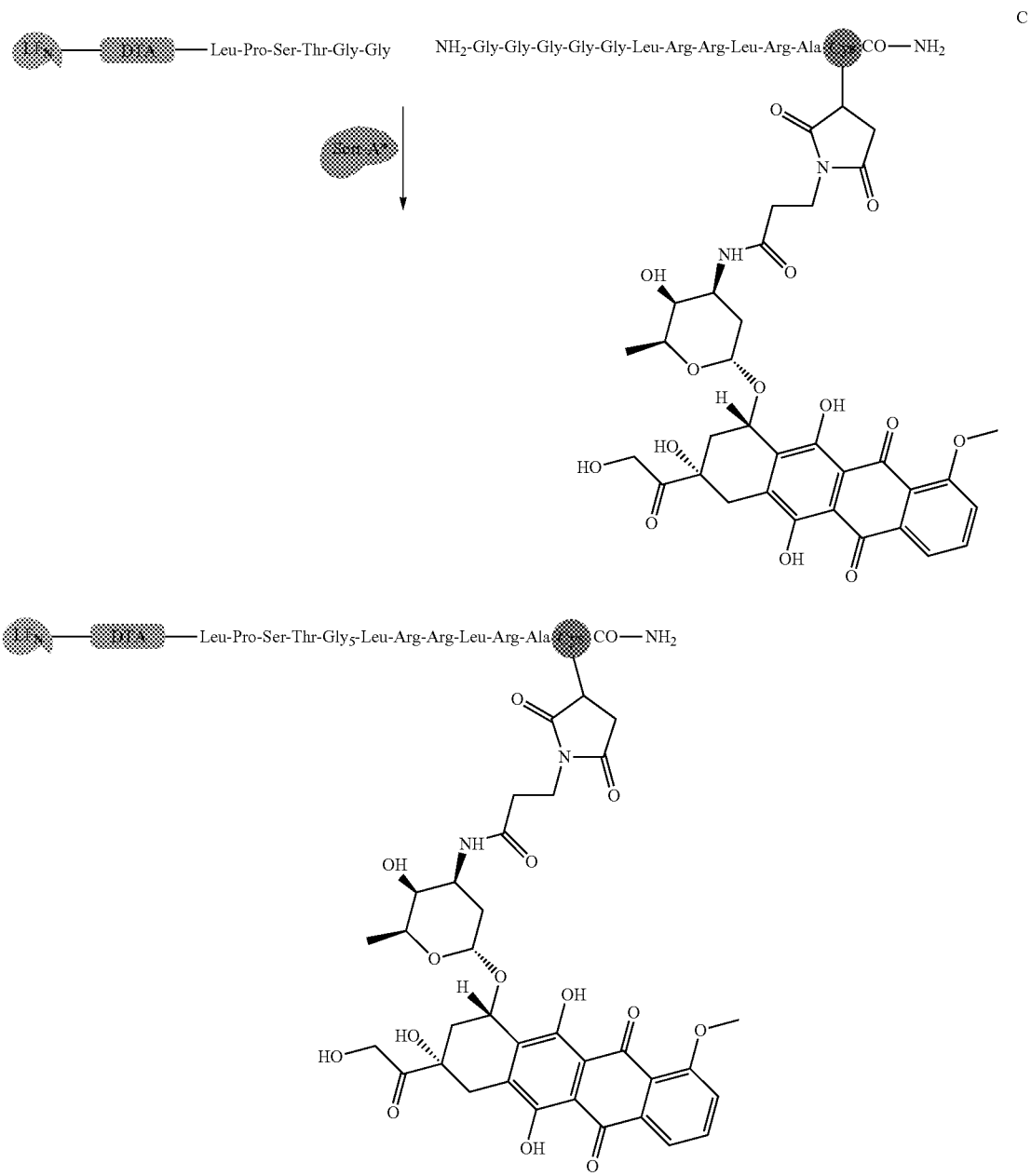

LFN-DTA-Leu-Pro-Ser-Thr-Gly-Gly (50 μM)
$NH_2$-Gly-Gly-Gly-Gly-Leu-Arg-Arg-Leu-Arg-Ala-Cys-CO—$NH_2$ (500 μM)
Deoxyrubicin
Sort-A* (5 μM)
RT, 30 min Chemoenzymatic Synthesis of LFN-DTA-Docetaxel Docetaxel (DOC) and maleimidopropionic acid were taken in anhydrous DCM, followed by addition of Mukaiyama's reagent and excess triethylamine at 0° C. The reaction mixture was slowly warmed up to room temperature and stirred 16 hours, at which TLC analysis (20:1/$CH_2Cl_2$:MeOH) indicated consumption of starting materials and formation of a major product. The reaction was quenched by addition of ethanol and additional stirring for 10 min, followed by concentration to dryness. The crude product was subjected to silica flash chromatography and afforded maleimido-DOC in 75% yield. The identity of the product was confirmed by ¹H-NMR and high resolution LC-MS.

A

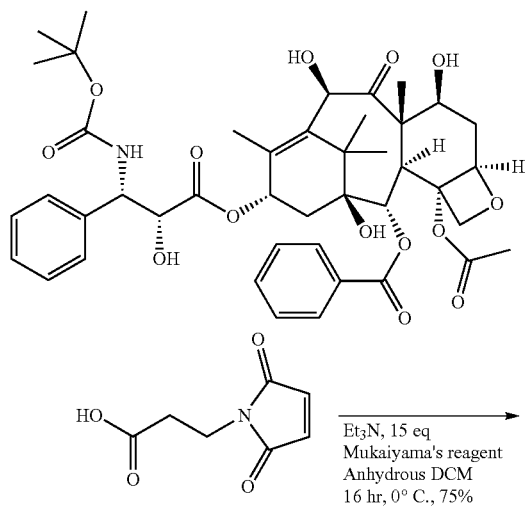

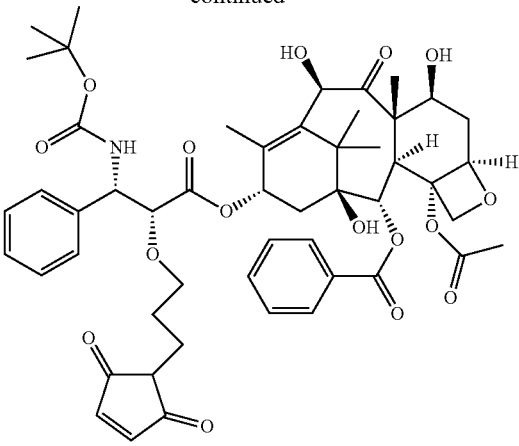

Chemoenzymatic Synthesis of LFN-DTA-Docetaxel

The C-terminus cysteine containing carrier peptide; Gly-Gly-Gly-Gly-Gly-Leu-Arg-Arg-Leu-Arg-Ala-Cys (SEQ ID NO: 35) was synthesized as described above. The sulfur of the cysteine amino acid was selectively reacted with the maleimido moiety on modified DOC by stirring peptide and Maleimido-DOX in DMF for 5 hours at 36° C., followed by 10 hours at room temperature. The reaction mixture was purified by RP-HPLC to give peptide-DOX conjugate in 93% yield.

B

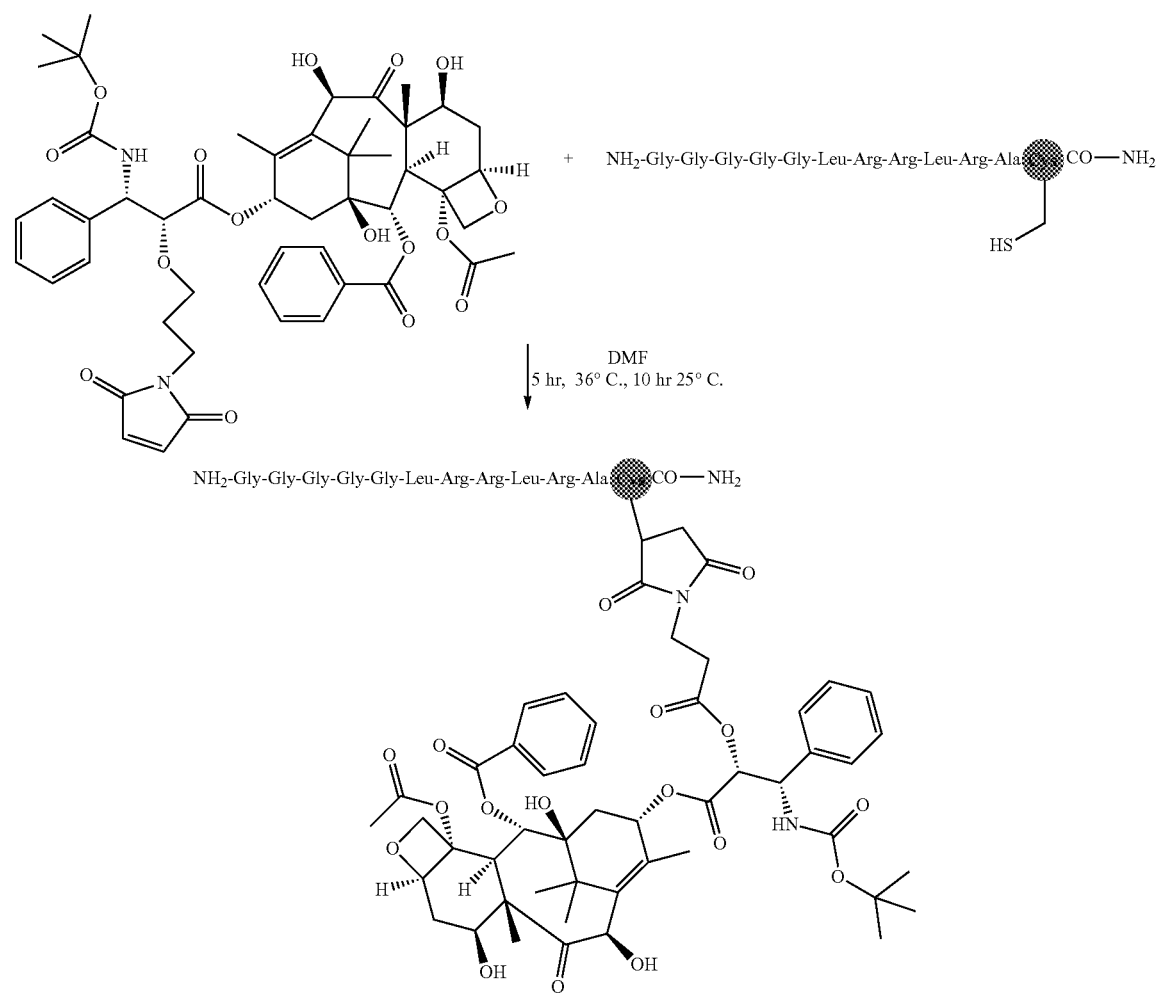

Chemoenzymatic Synthesis of LFN-DTA-Docetaxel

Enzymatic ligation of peptide-DOC to LFN-DTA: as described above in Example 13, Figure C.

C

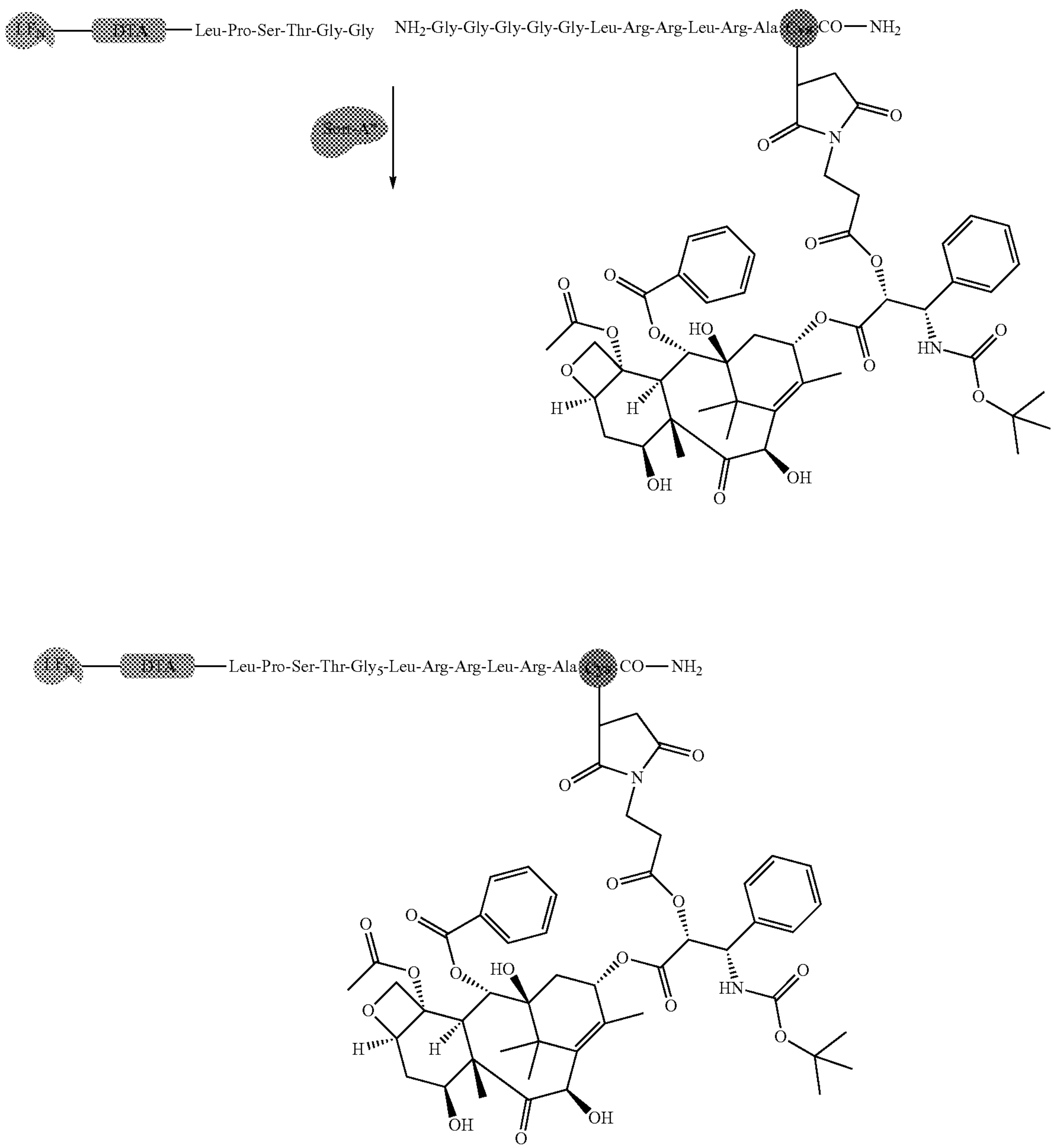

LFN-DTA-Leu-Pro-Ser-Thr-Gly-Gly (50 μM)
$NH_2$-Gly-Gly-Gly-Gly-Gly-Leu-Arg-Arg-Leu-Arg-Ala-Cys-CO—$NH_2$ (500 μM)
Docetaxel
Sort-A* (5 μM)
RT, 30 min LFN-DTA-Doxorubicin and LFN-DTA-Docetaxel were translocated through a PA pore with CHO cells

CHO-K1

Figure 16:
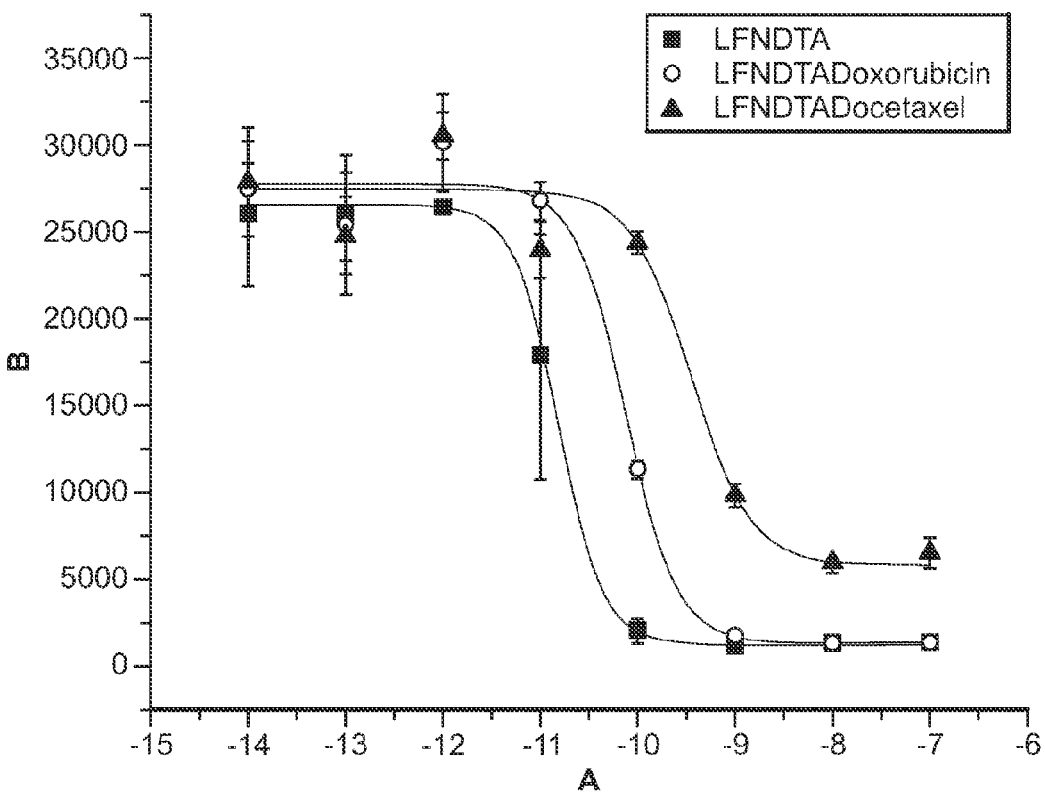
FIG. 16 is a graph depicting the translocation of $LF_N$-DTA-Doxorubicin and $LF_N$-DTA-Docetaxel through a PA pore into the cytosol of CHO cells.

Both LFN-Deoxyrubicn and LFN-Docetaxel were able to translocate through the PA pore. Interestingly, structurally planer Doxorubicin translocated relatively better compared to docetaxel that contains a rigid core (also confirmed by Western blots). This was an important finding with respect to the scope and limitations of molecular architecture that may be delivered inside cytosol using PA pore. Additionally, to the best of our knowledge, this was the first time that a protein containing a sugar moiety has been shown to translocate through PA pore. The results of this study are shown in FIG. 16.

Targeted delivery of LFN-DTA-Doxorubicin and LFN-DTA-Docetaxel to BT474 cells through PA-Her2 pore was demonstrated.

BT474

Figure 17:
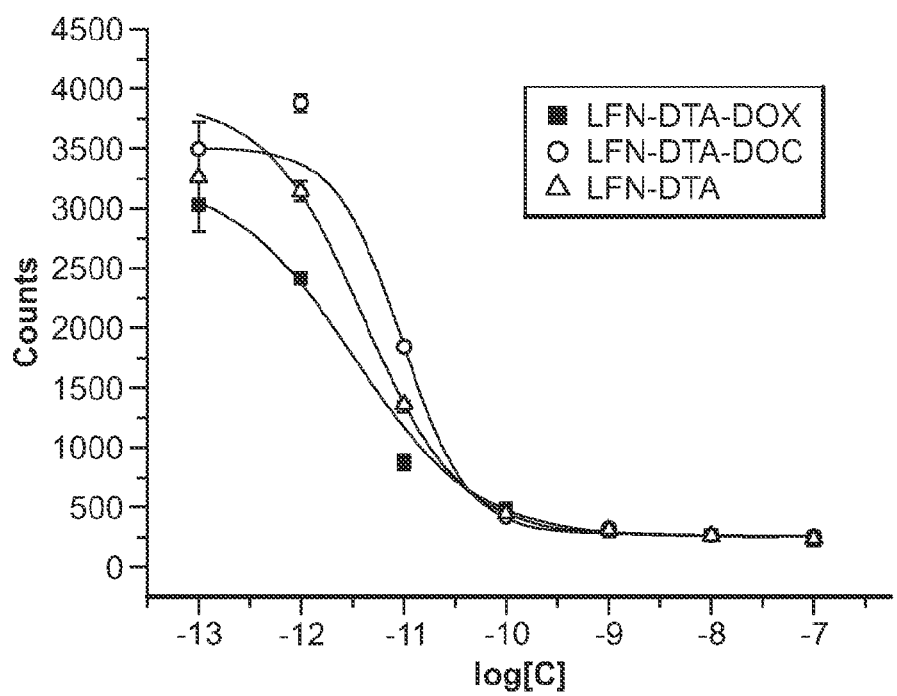
FIG. 17 is a graph demonstrating that modifying the receptor-binding domain of PA to target HER2 receptors can result in the delivery of the cytotoxic drugs, DOX and DOC to HER2 expressing BT474 breast cancer cells.

We demonstrated that by modifying the receptor-binding domain of PA to target HER2 receptors, we can deliver the cytotoxic drugs, DOX and DOC to HER2 expressing BT474 breast cancer cells. The results are shown in FIG. 17.

LFN-Doxorubicin and LFN-Docetaxel for cytotoxicity studies were prepared as described above and had the following structres

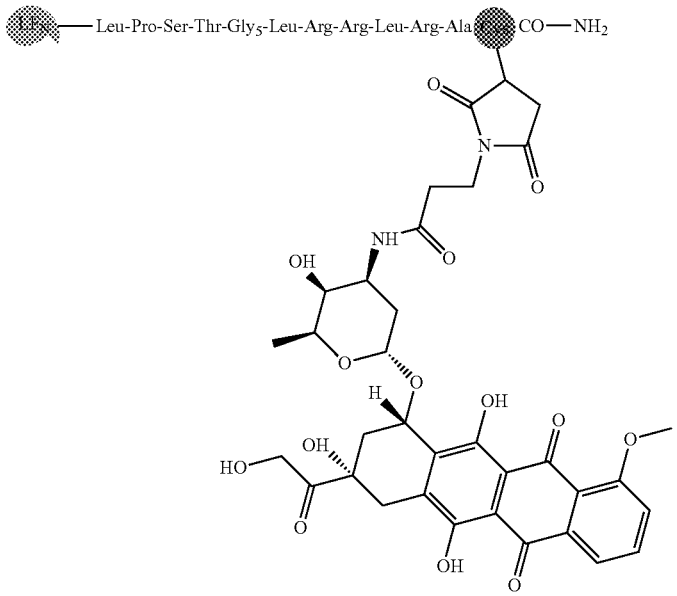

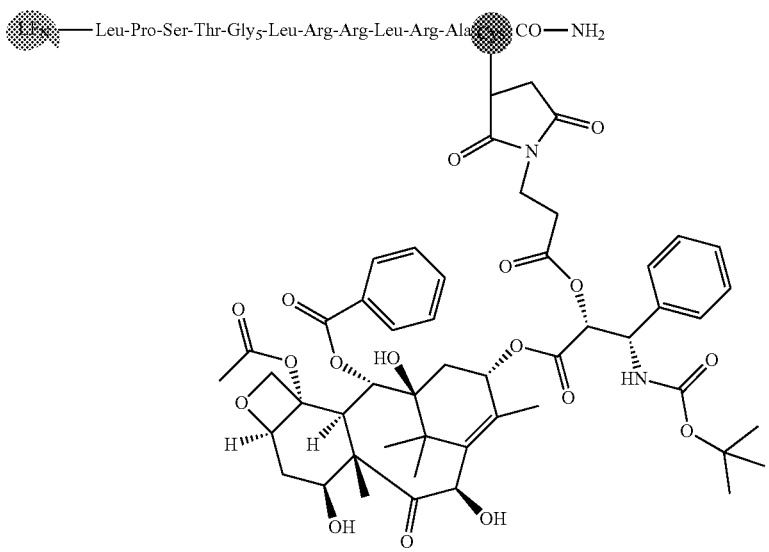

Cell Viability Assay with CHO-K1

Figure 18:
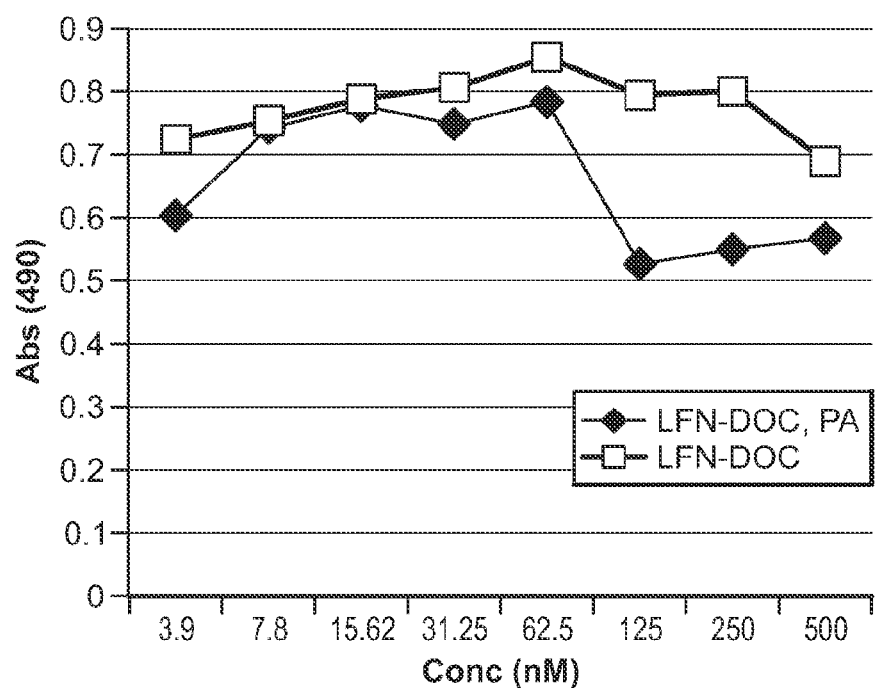
FIG. 18 is a graph depicting a cell viability assay with CHO-K1.

CHO-K1 cells plated on 96-well plates at 2,000 density. The cells were treated with LFN-DOC in the presence of 20 nM PA or LFN-DOC only at a concentration range 3.9-500 nM for 4 hours. After 4 hours, media was removed; cells were washed with PBS and incubated with fresh media for additional 44 hours. 44 hours later, cells were incubated with MTS reagent for an hour and viable cells were quantified by measuring the absorbance at 490 nm. The results showed a decrease in cell viability upon incubation with LFN-DOC, PA, which indicates the delivery of Doc to the cytosol to inhibit cell proliferation. The results are shown in FIG. 18.

More stable linkers for LFN-Docetaxel conjugates were prepared as followed.

51

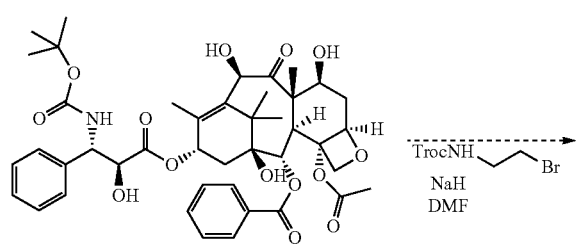

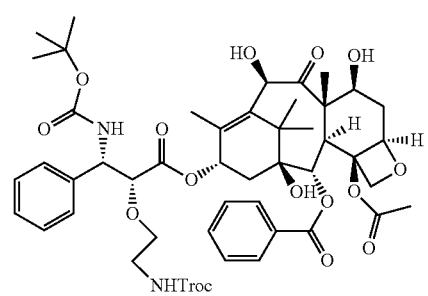

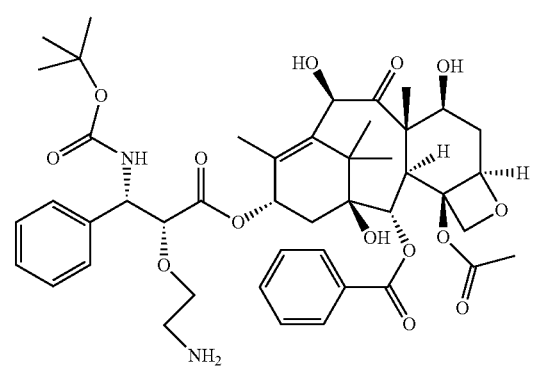

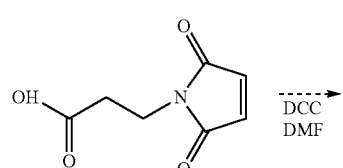

52
-continued

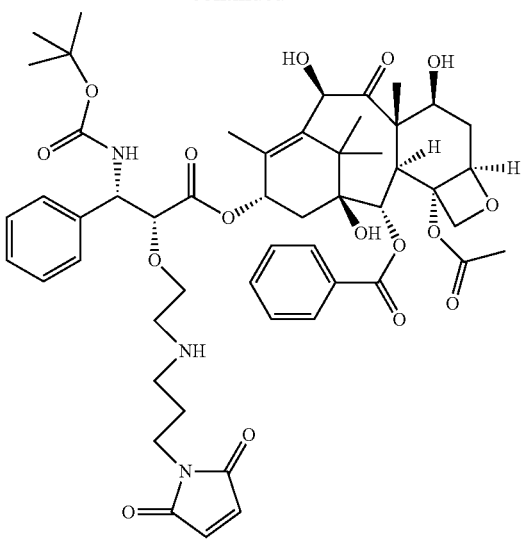

Another stable linker for a LFN-Docetaxel conjugate is the following:

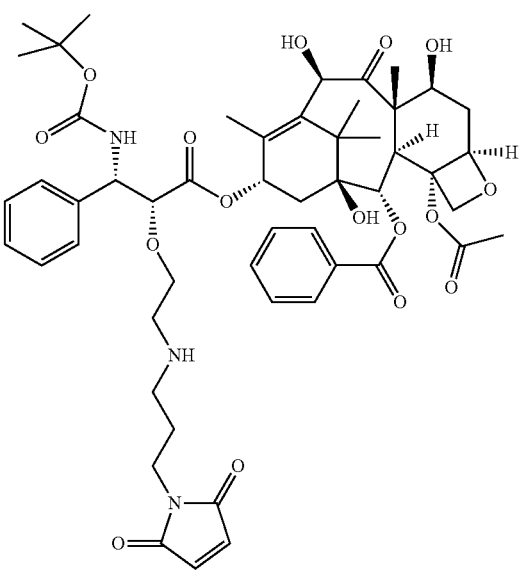

The following PA-small molecule constructs may be prepared using the methods of synthesis of peptide-Doxorubicin and peptide-Docetaxel as described herein.

Preparation of PA-Drug Conjugates:

LPSTGG (SEQ ID NO: 15) tag will be introduced to the C-terminus of PA and expressed recombinantly. Peptide-DOX and peptide-DOC or any peptide-small molecule of interest with N-terminal oligoglycine will then be conjugated to the purified PA-LPSTGG (SEQ ID NO: 15) through SrtA* mediated ligation to obtain PA-drug and PA-small molecule products.

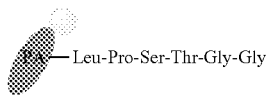
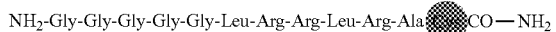
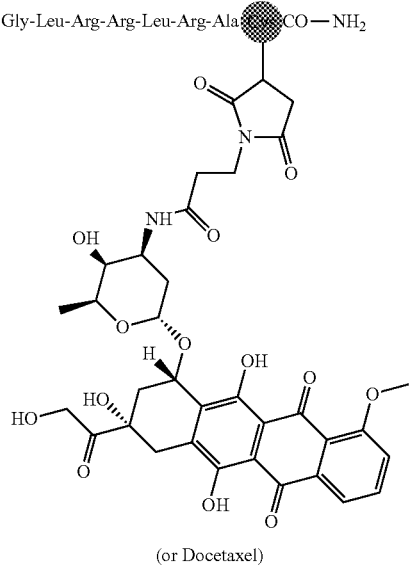

(or Docetaxel)

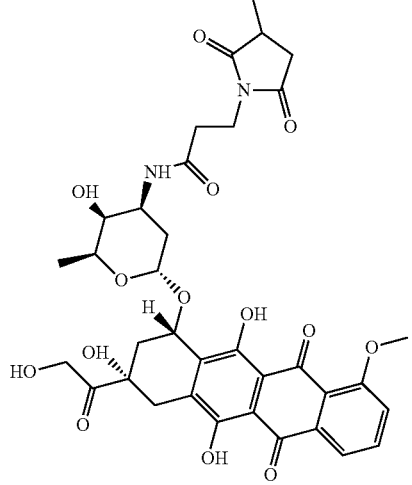

Each of the following Examples 15-18 is also included in the co-pending patent application, filed concurrently herewith and sharing a claim of priority to U.S. provisional application Ser. Nos. 61/649,421 and 61/649,866, both filed May 21, 2012, and incorporated by reference. The data is presented in the co-pending patent application.

Example 15

Flow Based Sortagging can be Performed at Low Nucleophile Concentrations

To demonstrate the feasibility of flow-based sortagging at low nucleophile concentrations a model flow-based platform was designed that employed a protein substrate eGFP-LPSTGG-His$_6$ (SEQ ID NO: 36), glycine nucleophile GGGG-LRL-CONH$_2$ (SEQ ID NO: 37), and SrtA*-His$_6$ (SEQ ID NO: 38), where SrtA* is an optimized variant demonstrating improved reaction kinetics relative to wild-type SrtA. Next, a microreactor was constructed from a short segment of 0.020" HP-PFA tubing, a stainless-steel filter frit, a precolumn filter, and finger tight fittings. The outlet tubing of the microreactor was connected to a vacuum manifold and a slurry of Ni-NTA agarose beads pre-incubated with SrtA* enzyme (in sortase buffer) was drawn into the microreactor body. A syringe containing a mixture of 200 µg of eGFP-LPSTGG-His$_6$ (SEQ ID NO: 36) and 20 µM G$_5$LRL in 800 µL sortase buffer (50 mM Tris, 150 mM NaCl, 10 mM CaCl$_2$, pH 8.2) was flowed through the SrtA* microreactor (hereafter referred to as the load fraction) at 65 µl/min via syringe pump. Subsequently, a syringe containing 1 mL of 20 µM G5LRL in sortase buffer (hereafter referred to as the push fraction) was similarly flowed through the microreactor to yield high purity material in good yield. His6 affinity tags on SrtA* and eGFP-LPSTGG-His$_6$ (SEQ ID NO: 36) ensured that both proteins remained resin bound; only upon effective transpeptidation was the eGFP-LPST-G$_5$LRL ligation product released from the microreactor.

To compare the designed flow reactor to traditional batch chemistry a sortagging reaction was performed with the eGFP construct and a model peptide (50 μM eGFP-LP-STGG-His$_6$, 20 μM G$_5$LRL, 3.5 μM SrtA*, sortase buffer, 20 min). To evaluate whether the desired ligation product (eGFP-LPST-G$_5$LRL) (SEQ ID NO: 39) could be isolated via batch mode affinity purification, the reaction mixture was incubated with of Ni-NTA slurry (freshly buffer exchanged with sortase buffer) for 10 minutes on a nutating mixer. LCMS analysis revealed that batch sortagging reactions provided minimal desired product. Ni-NTA treatment successfully removed unreacted starting material but major dimer formation was observed.

After flow sortagging reactions in the 20 uM nucleophile batch was successful, ligation efficiency was investigated by examining a range of G$_5$LRL (SEQ ID NO: 40) concentrations (2.5-40 μM). SML under continuous flow consistently yielded the desired ligation construct (eGFP-LPSTG$_5$LRL) (SEQ ID NO: 39) with no impurities and at higher yields than comparative batch reactions. While traditional sortagging reactions operate in the 300-500 μM nucleophile regime, high-efficiency ligation was observed at nucleophile concentrations in the 10-20 μM range for the sortase-mediated ligation with continuous flow.

Example 16

Reliable Bioconjugation with Different Protein Substrates

The eGFP flow experiments demonstrated reliable sortagging even at low micromolar nucleophile concentrations. To confirm that these observations were not protein specific, another sortagging substrate was studied: the anthrax toxin lethal factor N-terminal domain (LF$_N$). The construct LF$_N$-LPSTGG-His$_6$ (SEQ ID NO: 41) was expressed and purified via affinity chromatography and used to explore flow ligation between LF$_N$-LPSTGG-His$_6$ (SEQ ID NO: 41) and G$_5$LRL (SEQ ID NO: 40) (20 μM). Flow protocols identical to those used in model eGFP studies were utilized, with LF$_N$-LPSTGG-His$_6$ serving as the protein substrate instead of eGFP-LPSTGG-His$_6$ (SEQ ID NO: 36). High efficiency, high-purity ligation was observed as evidenced by the absence of side product or starting material contamination in the reactor flow-through. The lower limit of necessary nucleophile concentration was probed by screening G$_5$LRL (SEQ ID NO: 40) concentrations (2.5-40 μM). Flow reactions were compared to batch reactions between LF$_N$-LPSTGG-His$_6$ (SEQ ID NO: 41) and G$_5$LRL (SEQ ID NO: 40) (50 μM LF$_N$-LPSTGG-His$_6$ (SEQ ID NO: 41), 20 μM G$_5$LRL (SEQ ID NO: 40), 3.5 μM SrtA*-His, sortase buffer, 20 min). Comparatively, batch mode sortagging revealed minimal product formation and significant amounts of LF$_N$-LPSTGG-His$_6$ (SEQ ID NO: 41) hydrolysis and cyclization. Post Ni-NTA treatment of the batch reaction demonstrated complete removal of unreacted LF$_N$-LPSTGG-His$_6$ (SEQ ID NO: 41) but hydrolysis and cyclization byproducts were not removed because upon T-G bond cleavage they no longer contain a His$_6$ affinity tag.

Example 17

Platform Efficiency with Different Glycine Nucleophiles

Having demonstrated the platforms expanded working range with glycine nucleophile concentrations and demonstrating reliable bioconjugation with different protein substrates, the efficiency of this platform with different glycine nucleophiles was evaluated. Two types of glycine nucleophiles: 1) protein nucleophiles and 2) nucleophiles with poor solubility have rendered sortagging challenging in certain circumstances. Protein substrate LF$_N$-LPSTGG-His$_6$ (SEQ ID NO: 41) was subjected to flow based sortagging with protein nucleophile G$_5$-affibody (MW 6925.6) to yield the desired conjugate LF$_N$-LPSTG$_5$-affibody (SEQ ID NO: 42) in high purity and in good yield. Similarly, protein nucleophile G$_5$-fibronectin3 (SEQ ID NO: 43) (MW 11022.2) was employed to yield the desired construct LF$_N$-LPSTG$_5$-fibronectin3 (SEQ ID NO: 44) in high purity and in good yield. Finally, peptide nucleophile G$_5$-2Dpico (SEQ ID NO: 45) (a relatively insoluble fluorine containing peptide) was successfully conjugated to form the desired LF$_N$-LPSTG$_5$-2Dpico (SEQ ID NO: 46).

Example 18

Insertion of Synthetic Peptides into Protein Loops

The method uses a double ligation and concomitant protein fragment complementation to insert a synthetic peptide into protein loops. It is based on the fragment complementation property of many proteins. A protein is split, normally at the flexible loop regions, into two fragments that can complement and reassemble into stable and functional protein. We incorporate an LPSTGG (SEQ ID NO: 15) tag and a Cysteine at the N-terminal fragment (N) and the C-terminal fragment (C), respectively. We use SrtA to attach (sortagging) a synthetic peptide thioester onto the N fragment, which can then react with the C fragment bearing an N-terminal Cysteine under complementation-assisted NCL. Given the loop regions are tolerant in elongation, the final product would result in a native fold with concomitant insertion of the synthetic peptide in the loop.

Studies were performed using the 10th human fibronectin type III domain (10FN3) for model study. 10FN3 was dissected into two fragments at three different loops, FG loop, CD loop, and BC loop. The resulting fragments A-F, ABC, D-G, AB and C-G were expressed as SUMO fusions while fragment G were synthesized by solid phase peptide synthesis. In the case of 10FN3 dissected at the FG loop, SUMO was the first removed by SUMO protease to generate A-F_LPSTGG (SEQ ID NO: 47) (1), which then reacted with G$_5$-COSR (2) using SrtA. Following the generation of A-F_LPSTG$_5$COSR (SEQ ID NO: 48) (3), fragment G (4) was added to the mixture to undergo NCL. The product containing G$_5$ was inserted in the FG loop of 10FN3 (A-F_G$_5$_G) (5) was subsequently purified by anion-exchange column. In the case of 10FN3 dissected at CD loop or BC loop, we conducted a one-pot double ligation using double-His-tagged N terminal fragments which reacted with G$_5$-COSR and C terminal fragments in the presence of SrtA and Ni-NTA. By simple washing and subsequent SUMO cleavage, we obtained the full-length protein with G$_5$ inserted at CD loop (6) or BC loop (7) from the supernatant without further purification.

Circular dichroism was used to characterize the products from double ligation. All three products have similar CD spectra to that of wild-type 10FN3, implying the products are correctly folded. Thermal denaturation monitored by CD indicated that the products have similar $T_m$ or thermal stability to that of wild-type 10FN3. The binding properties of 10FN3 variants were fine-tuned by inserting different synthetic peptides in the loop regions.

REFERENCES (1) Young, J. A. T.; Collier, R. J. In Annual Review of Biochemistry 2007; Vol. 76, p 243.
(2) Leppla, S. H. Proceedings of the National Academy of Sciences of the United States of America-Biological Sciences 1982, 79, 3162.
(3) Bradley, K. A.; Mogridge, J.; Mourez, M.; Collier, R. J.; Young, J. A. T. Nature 2001, 414, 225.
(4) Scobie, H. M.; Rainey, G. J. A.; Bradley, K. A.; Young, J. A. T. Proc. Natl. Acad. Sci. U.S.A. 2003, 100, 5170.
(5) Klimpel, K. R.; Molloy, S. S.; Thomas, G.; Leppla, S. H. Proc. Natl. Acad. Sci. U.S.A. 1992, 89, 10277.
(6) Molloy, S. S.; Bresnahan, P. A.; Leppla, S. H.; Klimpel, K. R.; Thomas, G. J. Biol. Chem. 1992, 267, 16396.
(7) Milne, J. C.; Furlong, D.; Hanna, P. C.; Wall, J. S.; Collier, R. J. J. Biol. Chem. 1994, 269, 20607.
(8) Kintzer, A. F.; Thoren, K. L.; Sterling, H. J.; Dong, K. C.; Feld, G. K.; Tang, I I; Zhang, T. T.; Williams, E. R.; Berger, J. M.; Krantz, B. A. J. Mol. Biol. 2009, 392, 614.
(9) Duesbery, N. S.; Webb, C. P.; Leppla, S. H.; Gordon, V. M.; Klimpel, K. R.; Copeland, T. D.; Ahn, N. G.; Oskarsson, M. K.; Fukasawa, K.; Paull, K. D.; Vande Woude, G. F. Science 1998, 280, 734.
(10) Vitale, G.; Pellizzari, R.; Recchi, C.; Napolitani, G.; Mock, M.; Montecucco, C. Biochem. Biophys. Res. Commun. 1998, 248, 706.
(11) Feld, G. K.; Thoren, K. L.; Kintzer, A. F.; Sterling, H. J.; Tang, I I; Greenberg, S. G.; Williams, E. R.; Krantz, B. A. Nat. Struct. Mol. Biol. 2010, 17, 1383.
(12) Zhang, S.; Finkelstein, A.; Collier, R. J. Proc. Natl. Acad. Sci. U.S.A. 2004, 101, 16756.
(13) Krantz, B. A.; Melnyk, R. A.; Zhang, S.; Juris, S. J.; Lacy, D. B.; Wu, Z. Y.; Finkelstein, A.; Collier, R. J. Science 2005, 309, 777.
(14) Krantz, B. A.; Finkelstein, A.; Collier, R. J. J. Mol. Biol. 2006, 355, 968.
(15) Basilio, D.; Juris, S. J.; Collier, R. J.; Finkelstein, A. J. Gen. Physiol. 2009, 133, 307.
(16) Finkelstein, A. Philos. Trans. R. Soc. B-Biol. Sci. 2009, 364, 209.
(17) Arora, N.; Leppla, S. H. Infect. Immun. 1994, 62, 4955.
(18) Arora, N.; Klimpel, K. R.; Singh, Y.; Leppla, S. H. J. Biol. Chem. 1992, 267, 15542.
(19) Pentelute, B. L.; Sharma, O.; Collier, R. J. Angewandte Chemie-International Edition 2011, 50, 2294.
(20) Mazmanian, S. K.; Liu, G.; Hung, T. T.; Schneewind, O. Science 1999, 285, 760.
(21) Popp, M. W. L.; Ploegh, H. L. Angewandte Chemie-International Edition 2011, 50, 5024.
(22) Pallen, M. J.; Lam, A. C.; Antonio, M.; Dunbar, K. Trends Microbiol. 2001, 9, 97.
(23) Mao, H. Y.; Hart, S. A.; Schink, A.; Pollok, B. A. Journal of the American Chemical Society 2004, 126, 2670.
(24) Popp, M. W.; Antos, J. M.; Grotenbreg, G. M.; Spooner, E.; Ploegh, H. L. Nature Chemical Biology 2007, 3, 707.
(25) Samantaray, S.; Marathe, U.; Dasgupta, S.; Nandicoori, V. K.; Roy, R. P. Journal of the American Chemical Society 2008, 130, 2132.
(26) Guo, X. Q.; Wang, Q. L.; Swarts, B. M.; Guo, Z. W. Journal of the American Chemical Society 2009, 131, 9878.
(27) Chen, I.; Dorr, B. M.; Liu, D. R. Proc. Natl. Acad. Sci. U.S.A. 2011, 108, 11399.
(28) Nord, K.; Gunneriusson, E.; Ringdahl, J.; Stahl, S.; Uhlen, M.; Nygren, P. A. Nature Biotechnology 1997, 15, 772.
(29) Orlova, A.; Magnusson, M.; Eriksson, T. L. J.; Nilsson, M.; Larsson, B.; Hoiden-Guthenberg, I.; Widstrom, C.; Carlsson, J.; Tolmachev, V.; Stahl, S.; Nilsson, F. Y. Cancer Research 2006, 66, 4339.
(30) Nygren, P. A. Febs Journal 2008, 275, 2668.
(31) Jonsson, A.; Wallberg, H.; Herne, N.; Stahl, S.; Frejd, F. Y. Biotechnology and Applied Biochemistry 2009, 54, 93.
(32) Lundberg, E.; Brismar, H.; Graslund, T. Biotechnology and Applied Biochemistry 2009, 52, 17.
(33) Kmiecik, S.; Kolinski, A. Biophysical Journal 2008, 94, 726.
(34) Koide, A.; Bailey, C. W.; Huang, X. L.; Koide, S. J. Mol. Biol. 1998, 284, 1141.
(35) Lipovsek, D. Protein Engineering Design & Selection 2011, 24, 3.
(36) Mamluk, R.; Carvajal, I. M.; Morse, B. A.; Wong, H.; Abramowitz, J.; Aslanian, S.; Lim, A. C.; Gokemeijer, J.; Storek, M. J.; Lee, J.; Gosselin, M.; Wright, M. C.; Camphausen, R. T.; Wang, J.; Chen, Y.; Miller, K.; Sanders, K.; Short, S.; Sperinde, J.; Prasad, G.; Williams, S.; Kerbel, R.; Ebos, J.; Mutsaers, A.; Mendlein, J. D.; Harris, A. S.; Furfine, E. S. Mabs 2010, 2, 199.
(37) Wojcik, J.; Hantschel, O.; Grebien, F.; Kaupe, I.; Bennett, K. L.; Barkinge, J.; Jones, R. B.; Koide, A.; Superti-Furga, G.; Koide, S. Nat. Struct. Mol. Biol. 2010, 17, 519.
(38) Hackel, B. J.; Neil, J. R.; White, F. M.; Wittrup, K. D. Protein Engineering Design & Selection 2012, 25, 47.
(39) Dintzis, H. M.; Symer, D. E.; Dintzis, R. Z.; Zawadzke, L. E.; Berg, J. M. Proteins-Structure Function and Genetics 1993, 16, 306.
(40) Katayama, H.; Janowiak, B. E.; Brzozowski, M.; Juryck, J.; Falke, S.; Gogol, E. P.; Collier, R. J.; Fisher, M. T. Nat. Struct. Mol. Biol. 2008, 15, 754.
(41) Thoren, K. L.; Worden, E. J.; Yassif, J. M.; Krantz, B. A. Proc. Natl. Acad. Sci. U.S.A. 2009, 106, 21555.
(42) Brockwell, D. J.; Paci, E.; Zinober, R. C.; Beddard, G. S.; Olmsted, P. D.; Smith, D. A.; Perham, R. N.; Radford, S. E. Nat. Struct. Biol. 2003, 10, 731.
(43) Zimm, B. H.; Bragg, J. K. Journal of Chemical Physics 1959, 31, 526.
(44) Abi-Habib, R. J.; Singh, R.; Liu, S. H.; Bugge, T. H.; Leppla, S. H.; Frankel, A. E. Molecular Cancer Therapeutics 2006, 5, 2556.
(45) Liu, S. H.; Netzel-Arnett, S.; Birkedal-Hansen, H.; Leppla, S. H. Cancer Research 2000, 60, 6061.

The entire contents of all of the references (including literature references, issued patents, published patent applications, and co-pending patent applications) cited throughout this application are hereby expressly incorporated by reference.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method of disrupting a molecular interaction in a living cell, comprising
contacting the living cell with a pore forming protein and a fusion molecule comprising a pore specific delivery protein linked to a reagent, wherein the reagent is delivered to the cytosol of the living cell in an effective amount for disrupting a molecular interaction in the living cell.

2. The method of claim 1, wherein the reagent is a labeled compound, a halogenated compound, a morpholino, a therapeutic RNA, a protein mimic, antibody mimic, a minor image biomolecule or a monobody, or an engineered protein scaffold.

3. The method of claim 2, wherein the labeled compound is a peptide labeled with a biotin or a click chemistry reagent.

4. The method of claim 2, wherein the halogenated compound is a fluorinated peptide.

5. The method of claim 2, wherein the protein mimic is an antibody mimic.

6. The method of claim 1, wherein the molecular interaction is a protein-protein binding interaction and the reagent inhibits the protein-protein binding.

7. The method of claim 1, wherein the molecular interaction is a nucleic acid-protein binding interaction and the reagent inhibits the nucleic acid-protein binding.

8. The method of claim 1, wherein the molecular interaction is a nucleic acid function and the reagent inhibits the nucleic acid function.

9. A fusion molecule, comprising a pore specific delivery protein linked to a reagent, wherein the reagent is a labeled compound, a halogenated compound, a morpholino, a therapeutic RNA, a protein mimic, antibody mimic, a minor image biomolecule or a monobody, or an engineered protein scaffold.

10. The fusion protein of claim 9, wherein the labeled compound is a peptide labeled with a biotin or a click chemistry reagent.

11. The fusion protein of claim 9, wherein the halogenated compound is a fluorinated peptide.

12. A kit comprising:
a container housing together or in separate compartments a pore forming protein, a pore specific delivery protein, a peptide thioester and instructions for preparing a fusion protein and delivering the fusion protein to a living cell.

13. The kit of claim 12, further comprising a SrtA enzyme, which is optionally SrtA*.

14. The kit of claim 12, wherein the peptide thioester is $G_n$-Xaa-COSR, wherein n is 1-6 and wherein Xaa is an amino acid (SEQ ID NOs 1-4).

15. The kit of claim 12, wherein the peptide thioester is $G_n$-Xaa-COSR, wherein n is 3-5 and, wherein Xaa is Gly, Phe, Ser or Leu (SEQ ID NOs 5-7).

16. The kit of claim 12, wherein the peptide thioester is GGGGG-Xaa-COSR, wherein Xaa is Gly, Phe, Ser or Leu (SEQ ID NO: 7).

17. The kit of claim 12, wherein the peptide thioester is $G_n$-$X_m$-COSR (SEQ ID NO: 8), wherein n is 1-6, m is 1-6, and wherein X is an amino acid, naturally occurring or non-naturally occurring.

18. The kit of claim 17, wherein X is a D-amino acid.

19. The kit of claim 12, wherein the peptide thioester is $G_n$-Y-COSR (SEQ ID NO: 9-11), wherein n is 1-6 and wherein Y is a non-amino acid chemical entity.

20. The kit of claim 19, wherein in Y is a PEG unit.

21. A method for delivering a reagent to the cytosol of a living cell, comprising
contacting the living cell with a pore forming protein and a fusion molecule comprising a pore specific delivery protein linked to a reagent, wherein the reagent is delivered to the cytosol of the targeted living cell, and wherein the fusion molecule is prepared using a continuous flow enzymatic ligation reaction by flowing a N-terminal pore specific delivery protein and a peptide thioester comprising the reagent over a stationary phase containing a cysteine transpeptidase enzyme, wherein a N-terminal protein -COSR product is formed, and flowing a C-terminal protein over the stationary phase, wherein the C-terminal protein domain has a cysteine at the N-termini, to produce a modified protein having a chemical entity linking the N-terminal pore specific delivery protein and the C-terminal protein domain and wherein the linked molecule is the fusion molecule.

22. The method of claim 21, wherein the cysteine transpeptidase enzyme is a sortase.

* * * * *

UNITED STATES PATENT AND TRADEMARK OFFICE
CERTIFICATE OF CORRECTION

PATENT NO. : 9,498,538 B2  
APPLICATION NO. : 14/402856  
DATED : November 22, 2016  
INVENTOR(S) : Xiaoli Liao et al.

Page 1 of 1

It is certified that error appears in the above-identified patent and that said Letters Patent is hereby corrected as shown below:

In the Claims  
At Column 79, Claim 2, Line 41, please delete "minor" and replace with "mirror"  
At Column 79, Claim 9, Line 62, please delete "minor" and replace with "mirror"

Signed and Sealed this  
Twenty-fifth Day of April, 2017

Michelle K. Lee  
*Director of the United States Patent and Trademark Office*